(12) United States Patent
Shelton, IV et al.

(10) Patent No.: US 11,602,366 B2
(45) Date of Patent: Mar. 14, 2023

(54) SURGICAL SUTURING INSTRUMENT CONFIGURED TO MANIPULATE TISSUE USING MECHANICAL AND ELECTRICAL POWER

(71) Applicant: Cilag GmbH International, Zug (CH)

(72) Inventors: Frederick E. Shelton, IV, Hillsboro, OH (US); David C. Yates, Morrow, OH (US); Darcy W. Greep, Herriman, UT (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 885 days.

(21) Appl. No.: 16/112,129

(22) Filed: Aug. 24, 2018

(65) Prior Publication Data
US 2019/0125431 A1 May 2, 2019

Related U.S. Application Data

(60) Provisional application No. 62/665,128, filed on May 1, 2018, provisional application No. 62/665,192, filed
(Continued)

(51) Int. Cl.
*A61B 18/14* (2006.01)
*A61B 18/12* (2006.01)
(Continued)

(52) U.S. Cl.
CPC .......... *A61B 17/2909* (2013.01); *A61B 17/00* (2013.01); *A61B 17/105* (2013.01);
(Continued)

(58) Field of Classification Search
CPC . A61B 17/2909; A61B 34/76; A61B 17/3421; A61B 17/0469; A61B 17/0482;
(Continued)

(56) References Cited

U.S. PATENT DOCUMENTS

| 1,853,416 A | 4/1932 | Hall |
| 2,222,125 A | 11/1940 | Stehlik |

(Continued)

FOREIGN PATENT DOCUMENTS

| AU | 2015201140 A1 | 3/2015 |
| CA | 2795323 A1 | 5/2014 |

(Continued)

OTHER PUBLICATIONS

US 10,504,709, 8/2018, Karancsi et al. (withdrawn).
(Continued)

*Primary Examiner* — Tigist S Demie

(57) ABSTRACT

A surgical instrument comprising a jaw assembly is disclosed. The surgical instrument further comprises a motor-driven drive system configured to open the jaw assembly. The surgical instrument also comprises a control system configured to control the drive system and, also, control a power supply system configured to supply electrical power to electrodes defined in the outer surface, or outer surfaces, of the jaw assembly. In use, the surgical instrument can be used to apply mechanical energy and electrical energy to the tissue of a patient at the same time, or at different times. In certain embodiments, the user controls when the mechanical and electrical energies are applied. In some embodiments, the control system controls when the mechanical and electrical energies are applied.

20 Claims, 43 Drawing Sheets

Related U.S. Application Data on May 1, 2018, provisional application No. 62/665,139, filed on May 1, 2018, provisional application No. 62/665,177, filed on May 1, 2018, provisional application No. 62/665,129, filed on May 1, 2018, provisional application No. 62/665,134, filed on May 1, 2018, provisional application No. 62/578,855, filed on Oct. 30, 2017, provisional application No. 62/578,844, filed on Oct. 30, 2017, provisional application No. 62/578,804, filed on Oct. 30, 2017, provisional application No. 62/578,817, filed on Oct. 30, 2017, provisional application No. 62/578,835, filed on Oct. 30, 2017, provisional application No. 62/578,793, filed on Oct. 30, 2017.

(51) Int. Cl.

| | |
|---|---|
| *A61B 17/04* | (2006.01) |
| *A61B 17/06* | (2006.01) |
| *A61B 17/3201* | (2006.01) |
| *A61B 34/30* | (2016.01) |
| *A61B 17/29* | (2006.01) |
| *A61B 17/00* | (2006.01) |
| *A61B 17/128* | (2006.01) |
| *A61B 17/28* | (2006.01) |
| *A61B 17/10* | (2006.01) |
| *B33Y 80/00* | (2015.01) |
| *A61B 90/00* | (2016.01) |
| *A61B 17/32* | (2006.01) |
| *A61B 18/00* | (2006.01) |
| *F16D 27/00* | (2006.01) |
| *F16D 27/108* | (2006.01) |
| *F16D 27/12* | (2006.01) |
| *G09G 3/34* | (2006.01) |
| *G09G 3/36* | (2006.01) |
| *G09G 3/38* | (2006.01) |
| *A61B 90/98* | (2016.01) |
| *A61B 17/062* | (2006.01) |
| *A61B 17/068* | (2006.01) |
| *A61B 17/285* | (2006.01) |
| *A61B 17/295* | (2006.01) |
| *A61B 17/34* | (2006.01) |
| *G06F 3/147* | (2006.01) |
| *A61B 34/00* | (2016.01) |

(52) U.S. Cl.
CPC ........ *A61B 17/1285* (2013.01); *A61B 17/282* (2013.01); *A61B 17/2841* (2013.01); *A61B 17/29* (2013.01); *A61B 17/0469* (2013.01); *A61B 17/0482* (2013.01); *A61B 17/0483* (2013.01); *A61B 17/0491* (2013.01); *A61B 17/062* (2013.01); *A61B 17/06004* (2013.01); *A61B 17/068* (2013.01); *A61B 17/0625* (2013.01); *A61B 17/06066* (2013.01); *A61B 17/06114* (2013.01); *A61B 17/06133* (2013.01); *A61B 17/128* (2013.01); *A61B 17/285* (2013.01); *A61B 17/2833* (2013.01); *A61B 17/295* (2013.01); *A61B 17/3201* (2013.01); *A61B 17/3421* (2013.01); *A61B 17/3468* (2013.01); *A61B 18/1206* (2013.01); *A61B 18/1445* (2013.01); *A61B 34/30* (2016.02); *A61B 34/76* (2016.02); *A61B 90/03* (2016.02); *A61B 90/98* (2016.02); *A61B 2017/0003* (2013.01); *A61B 2017/00017* (2013.01); *A61B 2017/00026* (2013.01); *A61B 2017/00039* (2013.01); *A61B 2017/0046* (2013.01); *A61B 2017/00057* (2013.01); *A61B 2017/00061* (2013.01); *A61B 2017/00075* (2013.01); *A61B 2017/00115* (2013.01); *A61B 2017/00119* (2013.01); *A61B 2017/00128* (2013.01); *A61B 2017/00212* (2013.01); *A61B 2017/00221* (2013.01); *A61B 2017/00327* (2013.01); *A61B 2017/00367* (2013.01); *A61B 2017/00393* (2013.01); *A61B 2017/00398* (2013.01); *A61B 2017/00407* (2013.01); *A61B 2017/00424* (2013.01); *A61B 2017/00438* (2013.01); *A61B 2017/00464* (2013.01); *A61B 2017/00473* (2013.01); *A61B 2017/00477* (2013.01); *A61B 2017/00526* (2013.01); *A61B 2017/00734* (2013.01); *A61B 2017/06052* (2013.01); *A61B 2017/06076* (2013.01); *A61B 2017/2825* (2013.01); *A61B 2017/2845* (2013.01); *A61B 2017/2902* (2013.01); *A61B 2017/2903* (2013.01); *A61B 2017/2911* (2013.01); *A61B 2017/2923* (2013.01); *A61B 2017/2925* (2013.01); *A61B 2017/2926* (2013.01); *A61B 2017/2927* (2013.01); *A61B 2017/2929* (2013.01); *A61B 2017/2931* (2013.01); *A61B 2017/2943* (2013.01); *A61B 2017/2945* (2013.01); *A61B 2017/320044* (2013.01); *A61B 2018/0063* (2013.01); *A61B 2018/0072* (2013.01); *A61B 2018/00077* (2013.01); *A61B 2018/00083* (2013.01); *A61B 2018/00136* (2013.01); *A61B 2018/00178* (2013.01); *A61B 2018/00208* (2013.01); *A61B 2018/00404* (2013.01); *A61B 2018/00577* (2013.01); *A61B 2018/00595* (2013.01); *A61B 2018/00601* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01); *A61B 2018/1253* (2013.01); *A61B 2018/1266* (2013.01); *A61B 2018/146* (2013.01); *A61B 2018/1452* (2013.01); *A61B 2018/1457* (2013.01); *A61B 2090/035* (2016.02); *A61B 2090/0811* (2016.02); *B33Y 80/00* (2014.12); *F16D 27/004* (2013.01); *F16D 27/108* (2013.01); *F16D 27/12* (2013.01); *G06F 3/147* (2013.01); *G09G 3/344* (2013.01); *G09G 3/3648* (2013.01); *G09G 3/38* (2013.01); *G09G 2380/08* (2013.01)

(58) Field of Classification Search
CPC .......... A61B 17/0491; A61B 17/06066; A61B 17/06114; A61B 18/1206; A61B 34/30; A61B 17/06133; A61B 17/00; A61B 17/128; A61B 17/1285; A61B 90/98; A61B 17/062; A61B 17/0625; A61B 17/068; A61B 17/282; A61B 17/2841; A61B 17/285; A61B 17/29; A61B 17/295; A61B 90/03; A61B 17/105; A61B 17/3468; A61B 17/0483; A61B 17/06004; A61B 18/1445; A61B 2018/00178; A61B 2017/00424; A61B 2017/2943; A61B 2090/035; A61B 2018/00404; A61B 2018/00678; A61B 2017/00327; A61B 2018/00136; A61B 2017/2931; A61B 2017/00393; A61B 2018/00642; A61B 2017/2825; A61B 2017/320044; A61B 2017/0046; A61B 2018/00672; A61B
2017/00473; A61B 2017/2929; A61B
2017/2926; A61B 2017/00039; A61B
2017/00057; A61B 2017/00061; A61B
2017/00075; A61B 2017/00398; A61B
2017/06076; A61B 2018/00077; A61B
2018/00208; A61B 2018/00601; A61B
2018/00696; A61B 2018/00708; A61B
2018/00827; A61B 2018/00875; A61B
2018/00892; A61B 2018/1266; A61B
2018/1457; A61B 17/3201; A61B
2017/00407; A61B 2017/00477; A61B
2017/00115; A61B 2017/00734; A61B
2017/00026; A61B 2018/00083; A61B
2018/00702; A61B 2018/0072; A61B
2018/00767; A61B 2017/1452; A61B
2017/00017; A61B 2017/00212; A61B
2017/00367; A61B 2017/0003; A61B
2018/0063; A61B 2090/0811; A61B
2017/00128; A61B 2017/00221; A61B
2017/2845; A61B 2017/00526; A61B
2017/00438; A61B 2017/2903; A61B
2017/2911; A61B 2017/00119; A61B
2017/06052; A61B 2018/146; A61B
17/2833; A61B 2017/2902; A61B
2017/2923; A61B 2017/00464; A61B
2017/2925; A61B 2017/2927; A61B
2018/126; A61B 2018/00577; A61B
2018/1253; A61B 2017/2945; A61B
2018/00595; G06F 3/147; B33Y 80/00;
F16D 27/108; F16D 27/12; F16D 27/004;
F16D 11/16; F16D 27/09; G09G 3/344;
G09G 3/3648; G09G 3/38; G09G
2380/08

USPC .......................................................... 606/41
See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |

(56) References Cited

U.S. PATENT DOCUMENTS

| | | |
|---|---|---|
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Wlliamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 * | 8/2004 | Truckai .............. A61B 18/1445 606/52 |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |

(56) References Cited

U.S. PATENT DOCUMENTS

| | | |
|---|---|---|
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,255,045 B2 | 8/2012 | Gharib et al. |

(56) References Cited

U.S. PATENT DOCUMENTS

| | | |
|---|---|---|
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |

(56) References Cited

U.S. PATENT DOCUMENTS

| | | |
|---|---|---|
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |

(56) References Cited

U.S. PATENT DOCUMENTS

| | | |
|---|---|---|
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |

(56) References Cited

U.S. PATENT DOCUMENTS

| | | | |
|---|---|---|---|
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |

(56) References Cited

U.S. PATENT DOCUMENTS

| | | |
|---|---|---|
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Wiliams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |

(56) References Cited

U.S. PATENT DOCUMENTS

| | | |
|---|---|---|
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |

(56) References Cited

U.S. PATENT DOCUMENTS

| | | |
|---|---|---|
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |

(56) References Cited

U.S. PATENT DOCUMENTS

| | | |
|---|---|---|
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| D914,878 S | 3/2021 | Shelton, IV et al. |
| 10,932,784 B2 | 3/2021 | Mozdzierz et al. |
| 10,950,982 B2 | 3/2021 | Regnier et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 11,071,595 B2 | 7/2021 | Johnson et al. |
| 11,141,213 B2 | 10/2021 | Yates et al. |
| 11,185,325 B2 | 11/2021 | Shelton, IV et al. |
| D950,728 S | 5/2022 | Bakos et al. |
| D952,144 S | 5/2022 | Boudreaux |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0169584 A1 | 11/2002 | Fu et al. |
| 2003/0009111 A1 | 1/2003 | Cory et al. |
| 2003/0018329 A1 | 1/2003 | Hooven |
| 2003/0046109 A1 | 3/2003 | Uchikubo |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0023477 A1* | 2/2007 | Whitman ............... A61B 34/71 227/175.1 |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0058593 A1 | 3/2008 | Gu et al. |
| 2008/0059658 A1 | 3/2008 | Williams |

(56) References Cited

U.S. PATENT DOCUMENTS

| | | |
|---|---|---|
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0235052 A1 | 9/2008 | Node-Langlois et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1* | 4/2009 | Zemlok .............. A61B 90/98 227/175.2 |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1* | 10/2011 | Faller ............... A61B 18/1445 606/52 |
| 2011/0264000 A1 | 10/2011 | Paul et al. |
| 2011/0264078 A1 | 10/2011 | Lipow et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116391 A1* | 5/2012 | Houser ............... A61B 34/76 606/41 |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Nlklewskl et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |

(56) References Cited

U.S. PATENT DOCUMENTS

| | | |
|---|---|---|
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0117256 A1 | 5/2014 | Mueller et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0057675 A1 | 2/2015 | Akeel et al. |
| 2015/0066000 A1 | 3/2015 | An et al. |
| 2015/0066001 A1 * | 3/2015 | Jeong .................. A61B 17/29 606/1 |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038224 A1 * | 2/2016 | Couture .................. A61B 17/26 606/51 |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0184054 A1 | 6/2016 | Lowe |
| 2016/0192960 A1 | 7/2016 | Bueno et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270861 A1 | 9/2016 | Guru et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |

(56) References Cited

U.S. PATENT DOCUMENTS

| | | |
|---|---|---|
| 2016/0302210 A1 | 10/2016 | Thornton et al. |
| 2016/0310055 A1 | 10/2016 | Zand et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0156076 A1 | 6/2017 | Eom et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0173262 A1 | 6/2017 | Veltz |
| 2017/0177807 A1 | 6/2017 | Fabian |
| 2017/0196583 A1* | 7/2017 | Sugiyama ...... A61B 17/320068 |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153436 A1 | 6/2018 | Olson |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0193579 A1 | 7/2018 | Hanrahan et al. |
| 2018/0206884 A1 | 7/2018 | Beaupre |

(56) References Cited

U.S. PATENT DOCUMENTS

| | | |
|---|---|---|
| 2018/0206905 A1* | 7/2018 | Batchelor .......... A61B 18/1206 |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0315492 A1 | 11/2018 | Bishop et al. |
| 2018/0317826 A1 | 11/2018 | Muhsin et al. |
| 2018/0317916 A1 | 11/2018 | Wixey |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0360454 A1 | 12/2018 | Shelton, IV et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |

(56) References Cited

U.S. PATENT DOCUMENTS

| | | |
|---|---|---|
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207911 A1 | 7/2019 | Wiener et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |

(56) References Cited

U.S. PATENT DOCUMENTS

| | | |
|---|---|---|
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |
| 2022/0175374 A1 | 6/2022 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2509523 A | 7/2014 |
| JP | S5373315 A | 6/1978 |
| JP | 2001029353 A | 2/2001 |
| JP | 2007123394 A | 5/2007 |
| JP | 2010057642 A | 3/2010 |
| JP | 2017513561 A | 6/2017 |
| KR | 20140104587 A | 8/2014 |

(56) References Cited

FOREIGN PATENT DOCUMENTS

| | | |
|---|---|---|
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.
Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.
Yuyi Mao et al., "A Survey on Mobile Edge Computing: The Communication Perspective," IEEE Communications Surveys & Tutorials, pp. 2322-2358, Jun. 13, 2017.
Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey," Artificial Intelligence in Medicine, vol. 39, No. 1, pp. 1-24 (2006).
Zoccali, Bruno, "A Method for Approximating Component Temperatures at Altitude Conditions Based on CFD Analysis at Sea Level Conditions," (white paper), www.tdmginc.com, Dec. 6, 2018 (9 pages).
Slocinski et al., "Distance measure for impedance spectra for quantified evaluations," Lecture Notes on Impedance Spectroscopy, vol. 3, Taylor and Francis Group (Jul. 2012)—Book Not Attached.
Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

(56) References Cited

OTHER PUBLICATIONS

Dottorato, "Analysis and Design of the Rectangular Microstrip Patch Antennas forTM0n0 operating mode," Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012. YouTube, 5 screenshots, Retrieved from internet: <https://www.youtube.com/watch?v=UIdQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An Intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

"ATM-MPLS Network Interworking Version 2.0, af-aic-0178.001" ATM Standard, The ATM Forum Technical Committe, published Aug. 2003.

Lalys, et al., "Automatic knowledge-based recognition of low-level tasks in ophthalmological procedures", Int J CARS, vol. 8, No. 1, pp. 1-49, Apr. 19, 2012.

\* cited by examiner

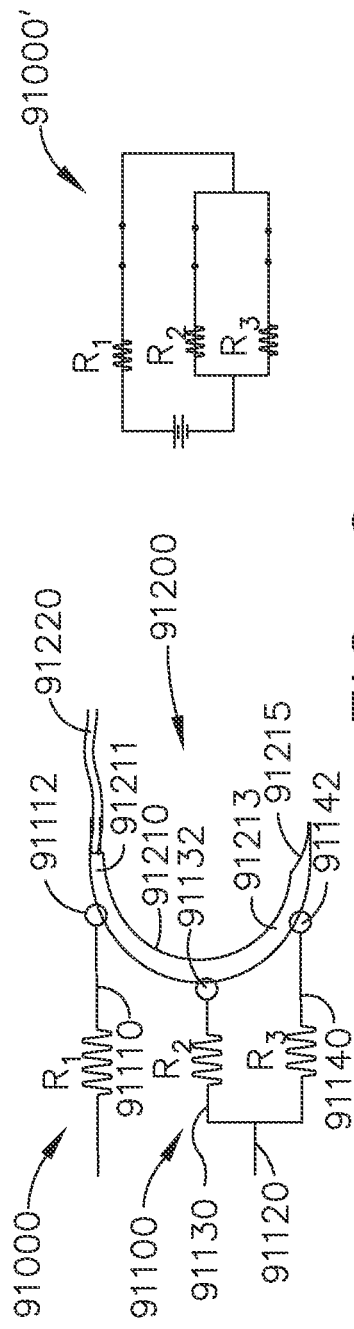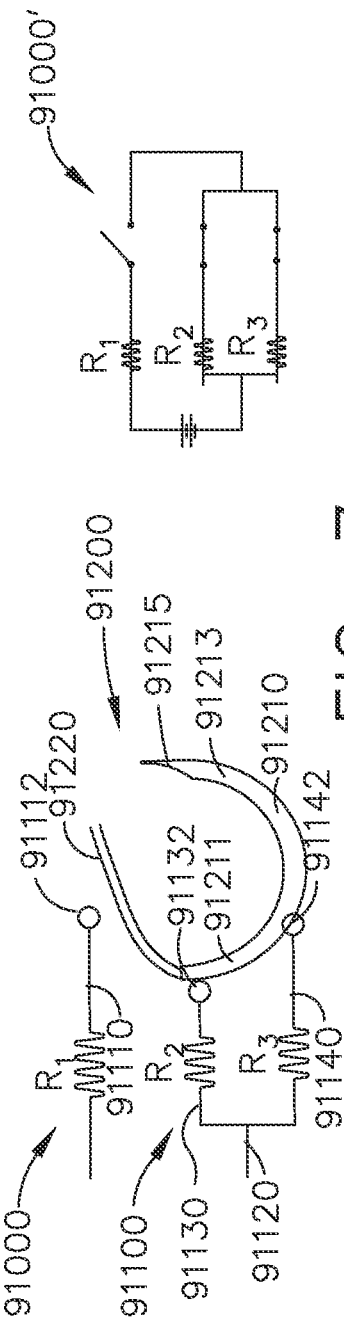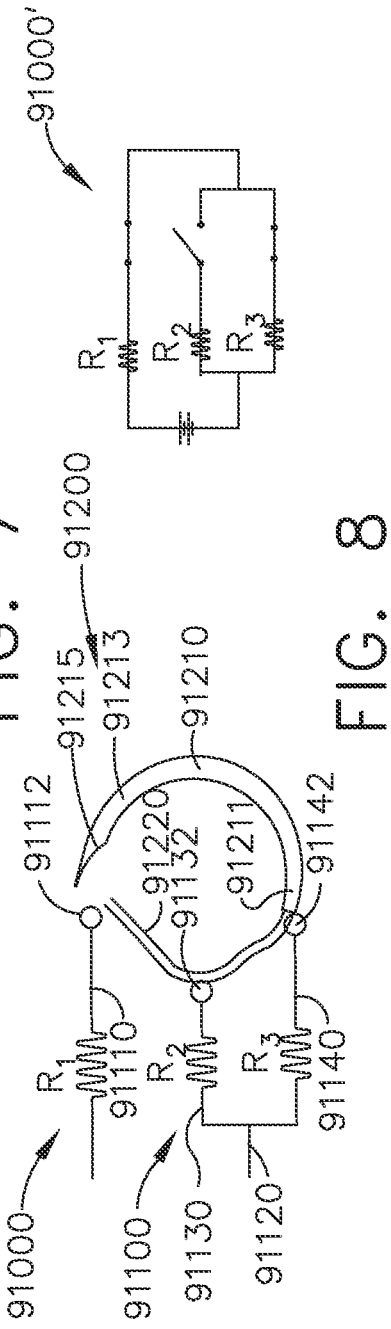

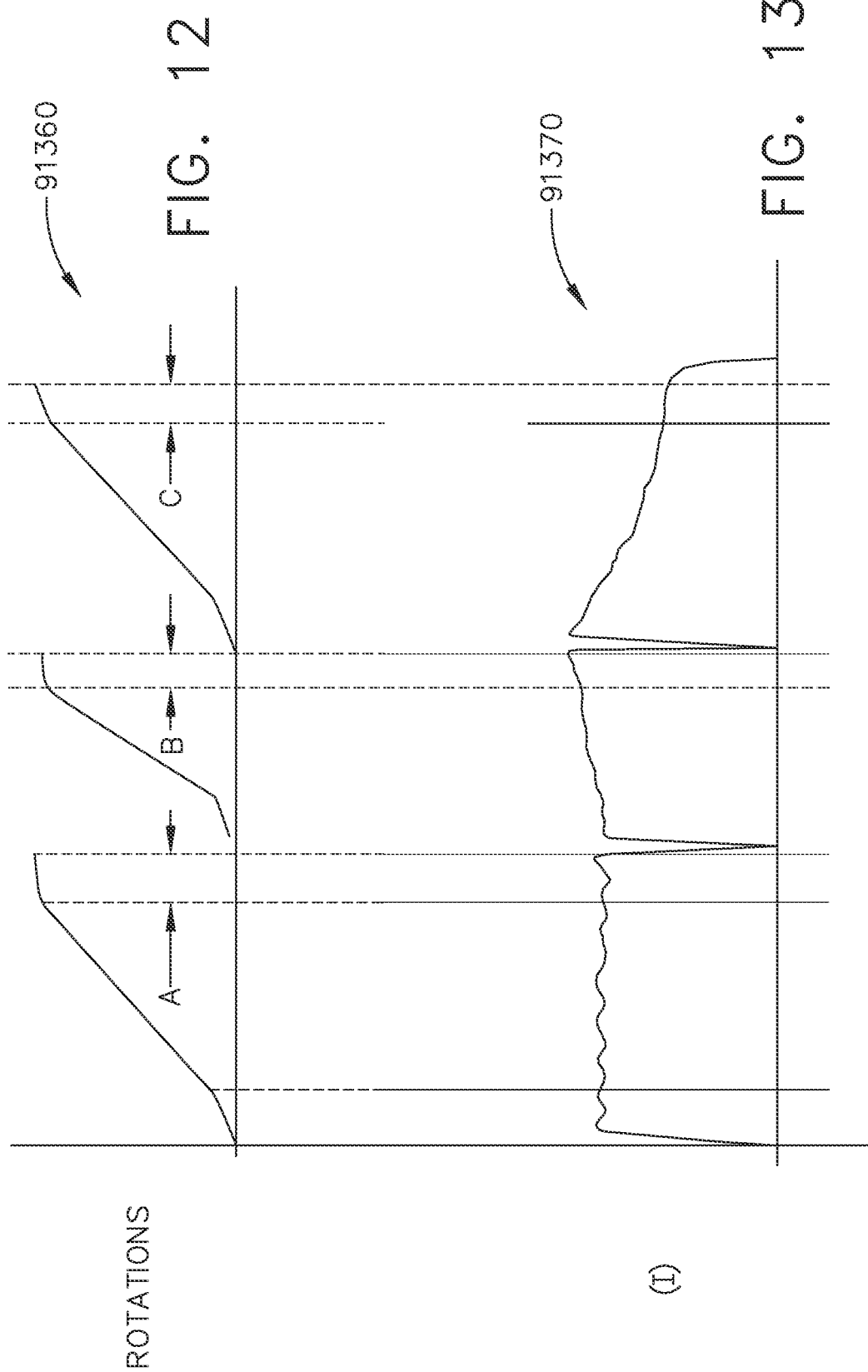

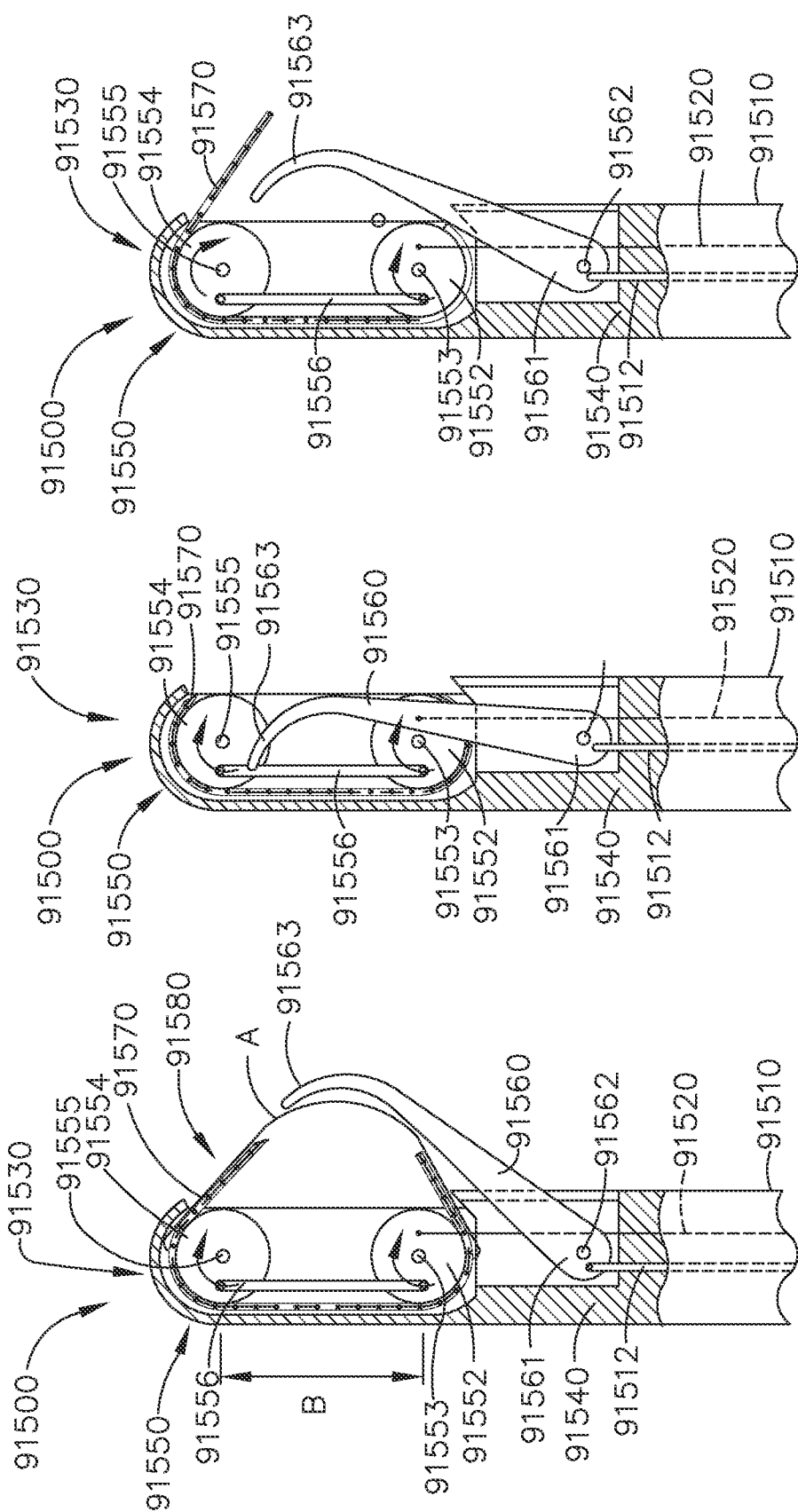

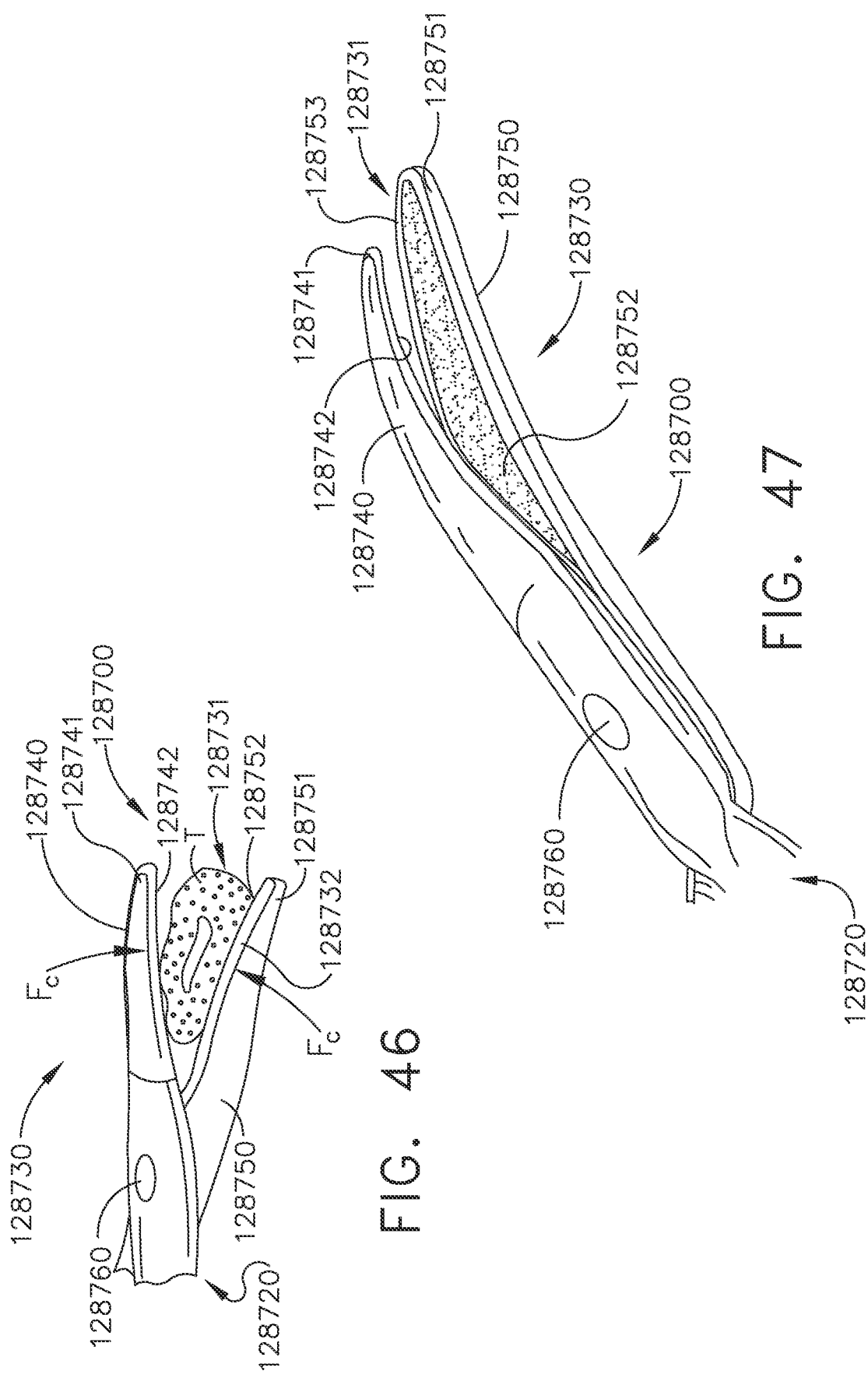

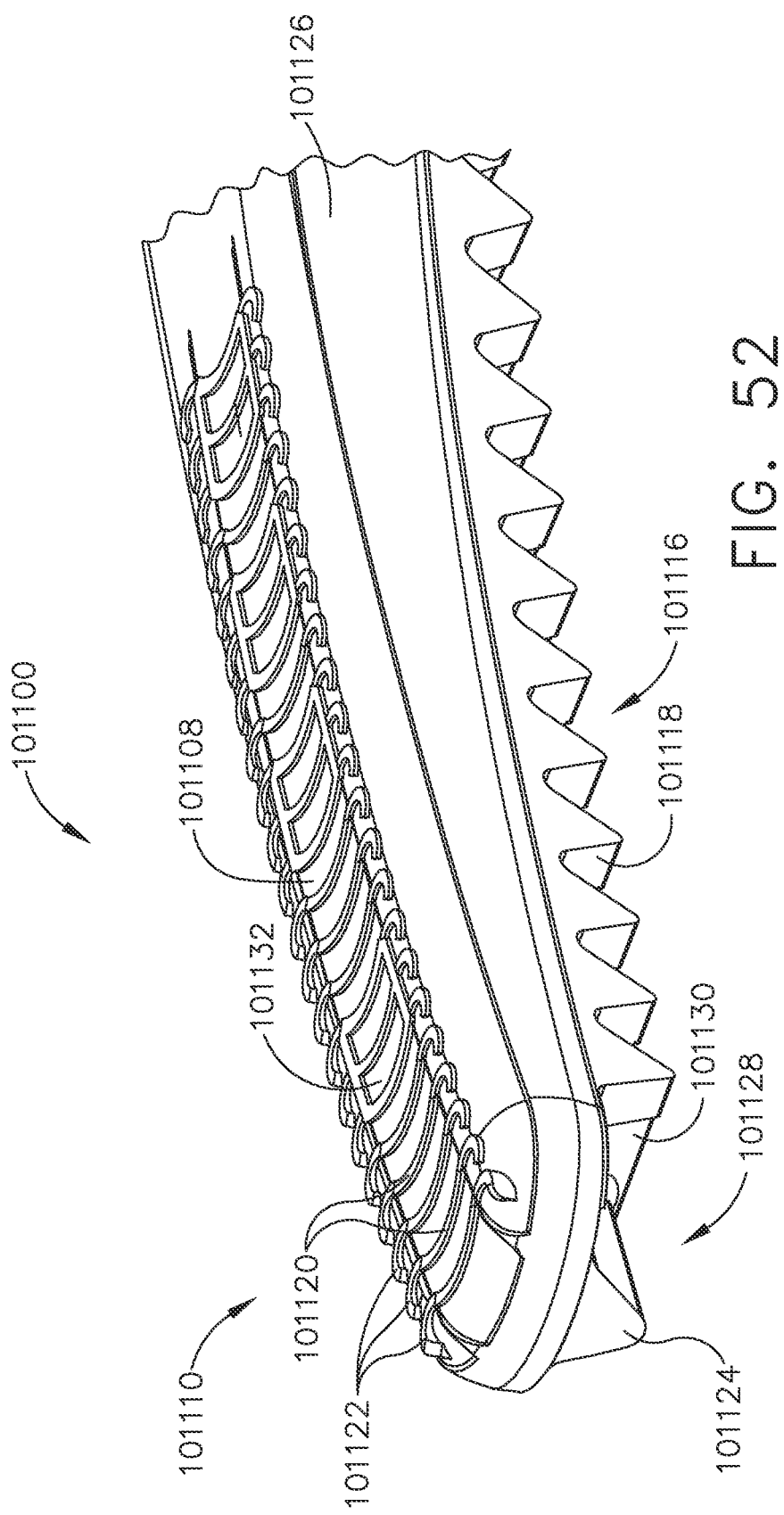

SURGICAL SUTURING INSTRUMENT CONFIGURED TO MANIPULATE TISSUE USING MECHANICAL AND ELECTRICAL POWER

CROSS-REFERENCE TO RELATED APPLICATIONS

This non-provisional application claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety. This non-provisional application claims the benefit under 35 U.S.C. § 119(e) of U.S. Provisional Patent Application Ser. No. 62/665,129, entitled SURGICAL SUTURING SYSTEMS, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, of U.S. Provisional Patent Application Ser. No. 62/665,128, entitled MODULAR SURGICAL INSTRUMENTS, filed May 1, 2018, of U.S. Provisional Patent Application Ser. No. 62/665,192, entitled SURGICAL DISSECTORS, filed May 1, 2018, and of U.S. Provisional Patent Application Ser. No. 62/665,134, entitled SURGICAL CLIP APPLIER, filed May 1, 2018, the disclosures of which are incorporated by reference herein in their entirety.

BACKGROUND

The present disclosure relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 6 is a schematic of a needle sensing system and a circuit diagram of a needle sensing circuit of the needle sensing system, wherein a needle of the needle sensing system is in a home position;

FIG. 7 is a schematic of the needle sensing system of FIG. 6 and a circuit diagram of the needle sensing circuit of FIG. 6, wherein the needle is in a first partially fired position;

FIG. 8 is a schematic of the needle sensing system of FIG. 6 and a circuit diagram of the needle sensing circuit of FIG. 6, wherein the needle is in a second partially fired position;

FIG. 12 is a graph of a second aspect of the adaptive needle driving system of FIG. 11;

FIG. 13 is a graph of a third aspect of the adaptive needle driving system of FIG. 11;

FIG. 14 is a plan view of a collapsible suturing device comprising a shaft and a needle driving system, wherein the needle driving system comprises a movable needle guide, and wherein the movable needle guide is in an expanded position;

FIG. 15 is a plan view of the suturing device of FIG. 14, wherein the movable needle guide is in a collapsed position;

FIG. 16 is a plan view of the suturing device of FIG. 14, wherein the movable needle guide is in a partially expanded position;

FIG. 46 is a partial perspective view of bipolar forceps being used to cut tissue;

FIG. 47 is a perspective view of the bipolar forceps of FIG. 46;

FIG. 52 is a partial perspective view of the jaw depicted in FIG. 51;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
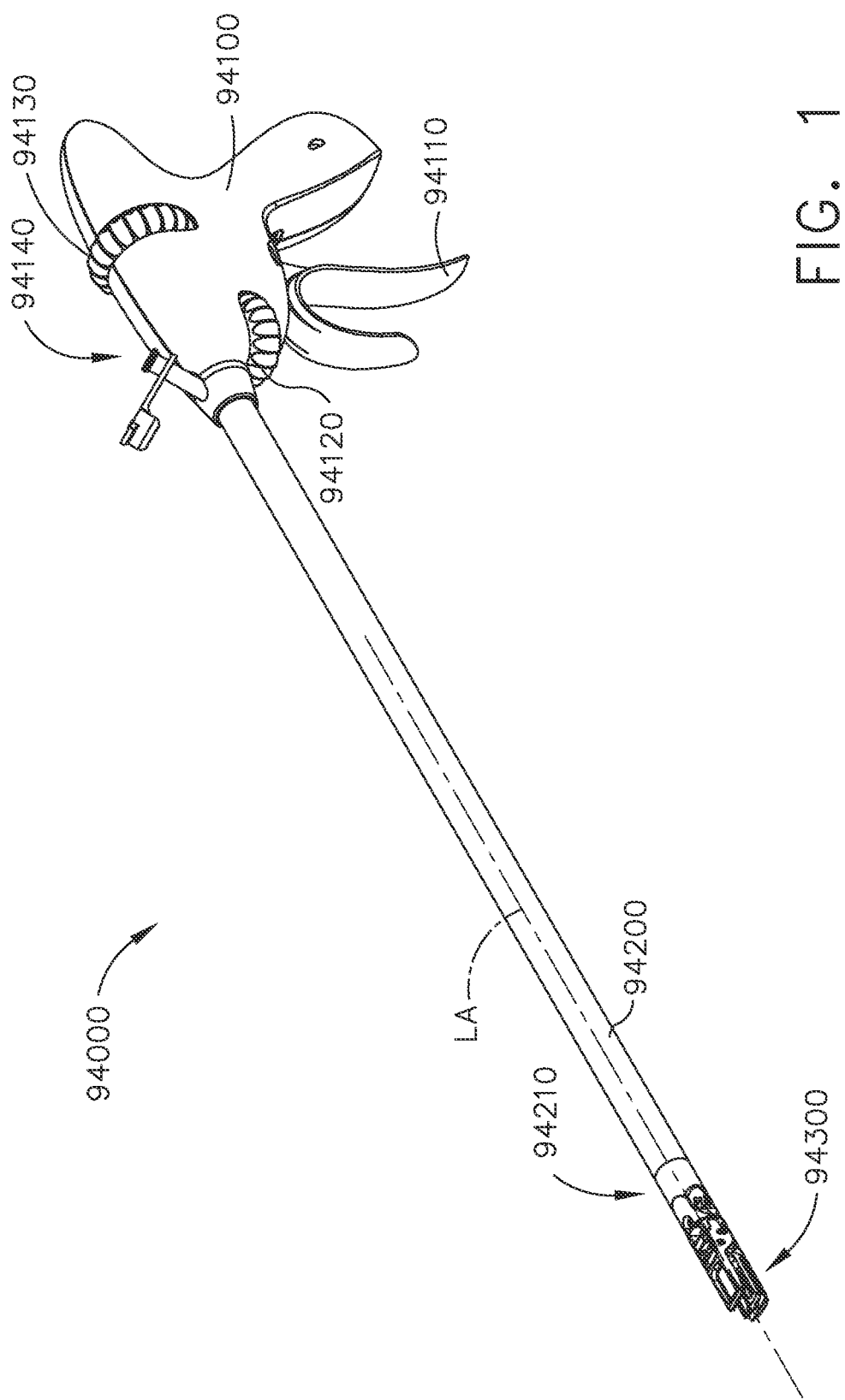
FIG. 1 is a perspective view of a surgical suturing instrument comprising a handle, a shaft, and an end effector.
Figure 2:
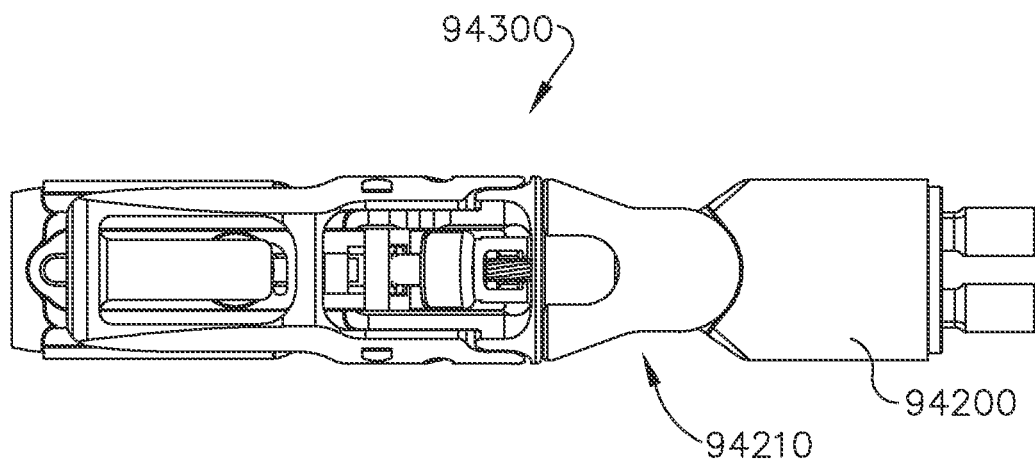
FIG. 2 is a partial plan view of the surgical suturing instrument of FIG. 1.
Figure 3:
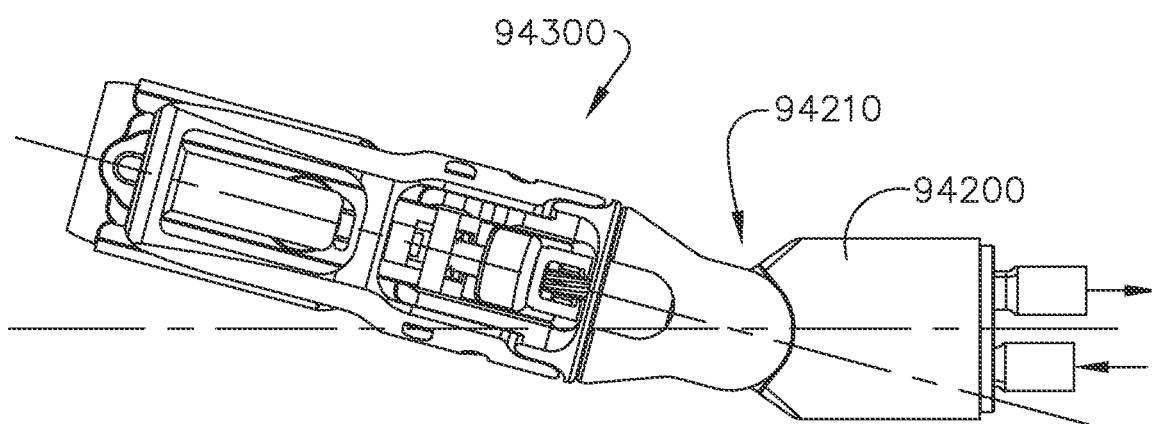
FIG. 3 is a partial plan view of the surgical suturing instrument of FIG. 1, wherein the end effector is in an articulated state.
Figure 4:
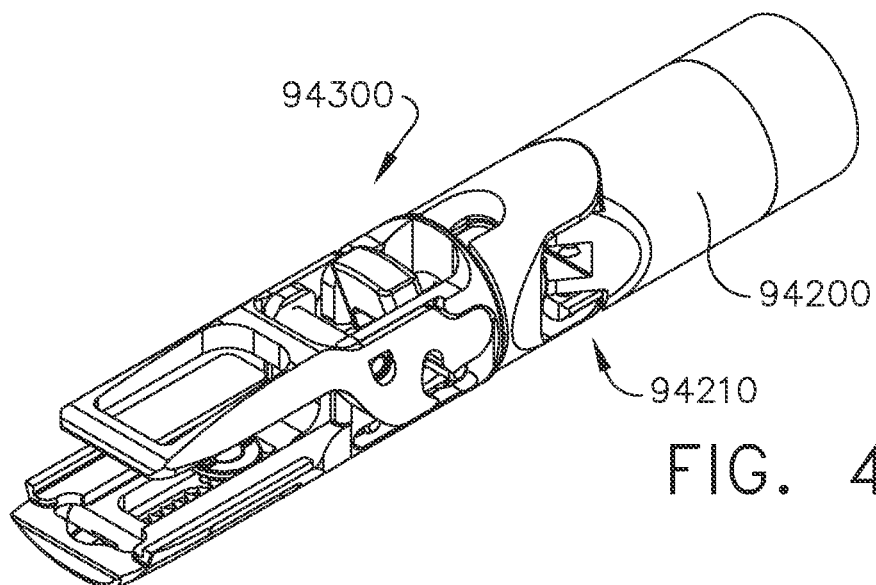
FIG. 4 is a partial perspective view of the surgical suturing instrument of FIG. 1.
Figure 5:
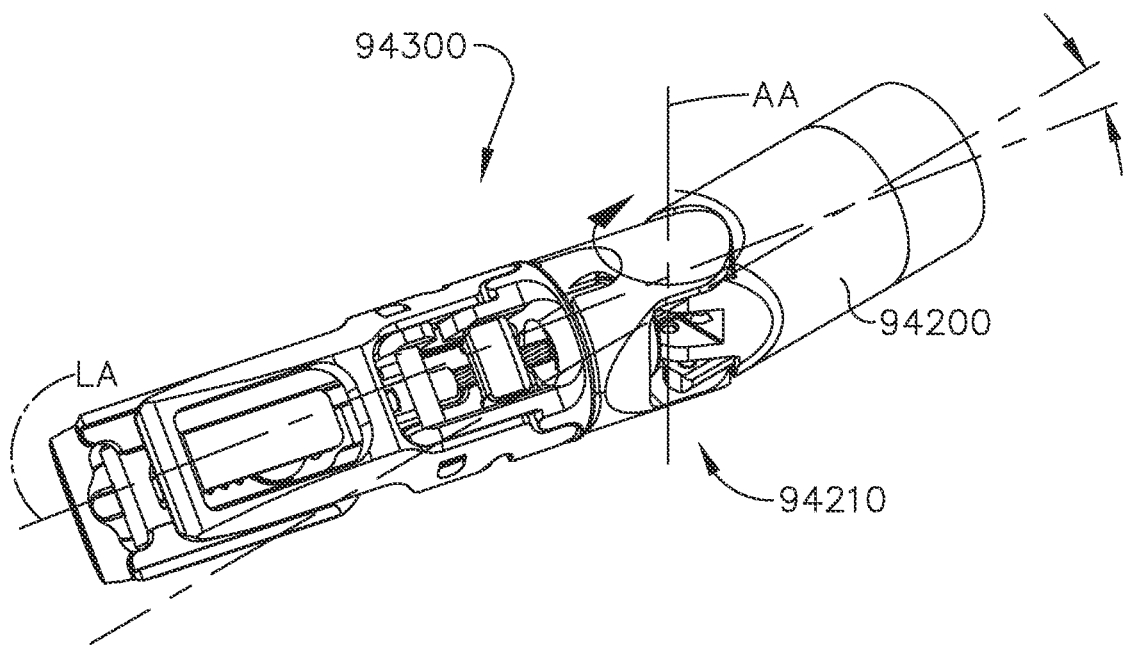
FIG. 5 is a partial perspective view of the surgical suturing instrument of FIG. 1, wherein the end effector is in an articulated and rotated state.

Applicant of the present application owns the following U.S. Patent Applications that were filed on Aug. 24, 2018, and which are each herein incorporated by reference in their respective entireties:

U.S. patent application Ser. No. 16/112,155, entitled SURGICAL SUTURING INSTRUMENT COMPRISING A CAPTURE WIDTH WHICH IS LARGER THAN TROCAR DIAMETER, now U.S. Pat. No. 11,564,703;

U.S. patent application Ser. No. 16/112,168, entitled SURGICAL SUTURING INSTRUMENT COMPRISING A NON-CIRCULAR NEEDLE, now U.S. Patent Application Publication No. 2019/0125336;

U.S. patent application Ser. No. 16/112,180, entitled ELECTRICAL POWER OUTPUT CONTROL BASED ON MECHANICAL FORCES, now U.S. Patent Application Publication No. 2019/0125432;

U.S. patent application Ser. No. 16/112,193, entitled REACTIVE ALGORITHM FOR SURGICAL SYSTEM, now U.S. Pat. No. 10,932,806;

U.S. patent application Ser. No. 16/112,099, entitled SURGICAL INSTRUMENT COMPRISING AN ADAPTIVE ELECTRICAL SYSTEM, now U.S. Patent Application Publication No. 2019/0125378;

U.S. patent application Ser. No. 16/112,112, entitled CONTROL SYSTEM ARRANGEMENTS FOR A MODULAR SURGICAL INSTRUMENT, now U.S. Patent Application Publication No. 2019/0125320;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE, now U.S. Patent Application Publication No. 2019/0125338;

U.S. patent application Ser. No. 16/112,097, entitled SURGICAL INSTRUMENT SYSTEMS COMPRISING BATTERY ARRANGEMENTS, now U.S. Patent Application Publication No. 2019/0125377;

U.S. patent application Ser. No. 16/112,109, entitled SURGICAL INSTRUMENT SYSTEMS COMPRISING HANDLE ARRANGEMENTS, now U.S. Patent Application Publication No. 2019/0125388;

U.S. patent application Ser. No. 16/112,114, entitled SURGICAL INSTRUMENT SYSTEMS COMPRISING FEEDBACK MECHANISMS, U.S. Pat. No. 10,980,560;

U.S. patent application Ser. No. 16/112,117, entitled SURGICAL INSTRUMENT SYSTEMS COMPRISING LOCKOUT MECHANISMS, now U.S. Patent Application Publication No. 2019/0125476;

U.S. patent application Ser. No. 16/112,095, entitled SURGICAL INSTRUMENTS COMPRISING A LOCKABLE END EFFECTOR SOCKET, now U.S. Pat. No. 11,291,465;

U.S. patent application Ser. No. 16/112,121, entitled SURGICAL INSTRUMENTS COMPRISING A SHIFTING MECHANISM, now U.S. Pat. No. 11,026,712;

U.S. patent application Ser. No. 16/112,151, entitled SURGICAL INSTRUMENTS COMPRISING A SYSTEM FOR ARTICULATION AND ROTATION COMPENSATION, now U.S. Pat. No. 10,772,651;

U.S. patent application Ser. No. 16/112,154, entitled SURGICAL INSTRUMENTS COMPRISING A BIASED SHIFTING MECHANISM, now U.S. Pat. No. 11,207,090;

U.S. patent application Ser. No. 16/112,226, entitled SURGICAL INSTRUMENTS COMPRISING AN ARTICULATION DRIVE THAT PROVIDES FOR HIGH ARTICULATION ANGLES, now U.S. Pat. No. 11,129,636;

U.S. patent application Ser. No. 16/112,062, entitled SURGICAL DISSECTORS AND MANUFACTURING TECHNIQUES, now U.S. Pat. No. 10,959,744;

U.S. patent application Ser. No. 16/112,098, entitled SURGICAL DISSECTORS CONFIGURED TO APPLY MECHANICAL AND ELECTRICAL ENERGY, now U.S. Patent Application Publication No. 2019/0125430;

U.S. patent application Ser. No. 16/112,237, entitled SURGICAL CLIP APPLIER CONFIGURED TO STORE CLIPS IN A STORED STATE, now U.S. Pat. No. 11,026,713;

U.S. patent application Ser. No. 16/112,245, entitled SURGICAL CLIP APPLIER COMPRISING AN EMPTY CLIP CARTRIDGE LOCKOUT, now U.S. Pat. No. 11,051,836;

U.S. patent application Ser. No. 16/112,249, entitled SURGICAL CLIP APPLIER COMPRISING AN AUTOMATIC CLIP FEEDING SYSTEM, now U.S. Pat. No. 11,109,878;

U.S. patent application Ser. No. 16/112,253, entitled SURGICAL CLIP APPLIER COMPRISING ADAPTIVE FIRING CONTROL, now U.S. Pat. No. 11,103,268; and U.S. patent application Ser. No. 16/112,257, entitled SURGICAL CLIP APPLIER COMPRISING ADAPTIVE CONTROL IN RESPONSE TO A STRAIN GAUGE CIRCUIT, now U.S. Pat. No. 11,071,560.

Applicant of the present application owns the following U.S. Patent Applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

The embodiments disclosed herein are configured for use with surgical suturing instruments and systems such as those disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein. The embodiments discussed herein are also usable with the instruments, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein. The embodiments discussed herein are also usable with the instruments, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated by reference in their entireties herein. Generally, these surgical suturing instruments comprise, among other things, a shaft, an end effector attached to the shaft, and drive systems positioned within the shaft to transfer motion from a source motion to the end effector. The motion source can comprise a manually driven actuator, an electric motor, and/or a robotic surgical system. The end effector comprises a body portion, a needle track defined within the body portion, and a needle driver configured to drive a needle through a rotational firing stroke. The needle is configured to be guided through its rotational firing stroke within the body portion by the needle track. In various instances, the needle driver is similar to that of a ratchet system. In at least one instance, the needle driver is configured to drive the needle through a first half of the rotational firing stroke which places the needle in a hand-off position—a position where a tissue-puncturing end of the needle has passed through the target tissue and reentered the body portion of the end effector. At such point, the needle driver can be returned to its original position to pick up the tissue-puncturing end of the needle and drive the needle through a second half of its rotational firing stroke. Once the needle driver pulls the needle through the second half of its rotational firing stroke, the needle driver is then returned to its original unfired position to grab the needle for another rotational firing stroke. The drive systems can be driven by one or more motors and/or manual drive actuation systems. The needle comprises suturing material, such as thread, for example, attached thereto. The suturing material is configured to be pulled through tissue as the needle is advanced through its rotational firing stroke to seal the tissue and/or attached the tissue to another structure, for example.

FIGS. 1-5 depict a surgical suturing instrument 94000 configured to suture the tissue of a patient. The surgical suturing instrument 94000 comprises a handle 94100, a shaft 94200 extending distally from the handle 94100, and an end effector 94300 attached to the shaft 94200 by way of an articulation joint 94210. The handle 94100 comprises a firing trigger 94110 configured to actuate a firing drive of the surgical suturing instrument 94000, a first rotational actuator 94120 configured to articulate the end effector 94300 about an articulation axis AA defined by the articulation joint 94210, and a second rotational actuator 94130 configured to rotate the end effector 94300 about a longitudinal axis LA defined by the end effector 94300. The surgical suturing instrument 94000 further comprises a flush port 94140. Examples of surgical suturing devices, systems, and methods are disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein.

FIGS. 6-8 depict a needle sensing system 91000 configured to be used with a surgical suturing instrument system. The needle sensing system 91000 comprises a resistive sensing circuit configured to allow a control program of a control interface to determine the position of a needle during its firing stroke by monitoring the resistance of the resistive sensing circuit. The needle sensing system 91000 comprises a needle sensing circuit 91100 and a needle 91200. The needle sensing circuit 91100 comprises a supply portion, or leg, 91110 terminating at a first terminal 91112 and comprising a first resistance R1. The needle sensing circuit 91100 further comprises a return portion 91120 comprising a first return leg 91130 terminating at a first return terminal 91132 and a second return leg 91140 terminating a second return terminal 91142. The first return leg 91130 and the second return leg 91140 are wired in parallel with respect to each other. The first return leg 91130 comprises a second resistance R2 and the second return leg 91140 comprises a third resistance R3. Discussed in greater detail below, the needle 91210 is configured to act as a switch for the needle sensing circuit 91100 by contacting the terminals 91112, 91132, and 91142 during its firing stroke as the needle 91200 moves in a rotational direction to suture tissue. The resistance of such a circuit can be monitored by a processor to determine the location of the needle 91200 during its firing stroke.

The needle 91200 comprises a tip 91213, a butt end 91211, and an arcuate shaft 91212 extending between the tip 91213 and the butt end 91211. The needle 91200 further comprises suturing material 91220 attached to the butt end 91211 of the needle 91200. The tip 91213 comprises a bevel, or point, 91215 configured to pierce tissue during a firing stroke of the needle 91200. As the needle 91200 moves through its firing stroke, it is configured to move into and out of contact with the terminals 91112, 91132, and 91142. In its starting, or home, position (FIG. 6), the needle 91200 is in contact with all three terminals 91112, 91132, and 91142. The total resistance of the circuit 91100 in this configuration can be detected by the control system of the suturing instrument to identify that the needle 91200 is in its starting position. The total resistance of the circuit 91100 in this configuration is shown in the circuit diagram 91000' of FIG. 6 and can be referred to as the starting position resistance. Once the needle 91200 is advanced out of its starting position and the butt end 91211 of the needle 91200 moves out of contact with the terminal 91112, the needle 91200 has been partially fired and is now only in contact with two terminals 91132, 91142 (FIG. 7). The total resistance of the circuit 91100 in this configuration can be detected by the control system to identify that the needle 91200 is in a first partially-fired position. The total resistance of the circuit 91100 in this configuration is shown in the circuit diagram 91000' of FIG. 7 and can be referred to as the first partially-fired position resistance. Once the needle 91200 is advanced out of contact with the second terminal 91132 and back into contact with the first terminal 91112, the circuit 91100 now comprises a third total resistance that is different from the starting position resistance and the first-partially fired position resistance. This can be referred to as the second partially-fired position resistance (FIG. 8). Because the second partially-fired position resistance is different than the starting position resistance and the first partially-fired position resistance, the second partially-fired position resistance can be detected to determine that the needle 91200 has moved into the second partially-fired position.

The system 91100 permits the needle location to be detected directly. Monitoring the needle location over a period of time can provide means for determining the rate of advancement of the needle and/or changes in rate of advancement of the needle during its firing stroke. In various instances, if the needle is sensed to be moving at a rate slower than preferred, for example, the instrument can automatically adjust a power control program of the motor which is advancing the needle through its firing stroke to speed up the needle. Similarly, if the needle is sensed to be moving at a rate faster than preferred, for example, the instrument can automatically adjust the power control program of the motor which is advancing the needle through its firing stroke to slow down the needle. This arrangement allows the control program to adapt the rate and/or sequence at which the needle is fired during a procedure and/or during each firing stroke of the needle to better accommodate variable conditions such as, for example, variable tissue thicknesses during suturing.

Figure 9:
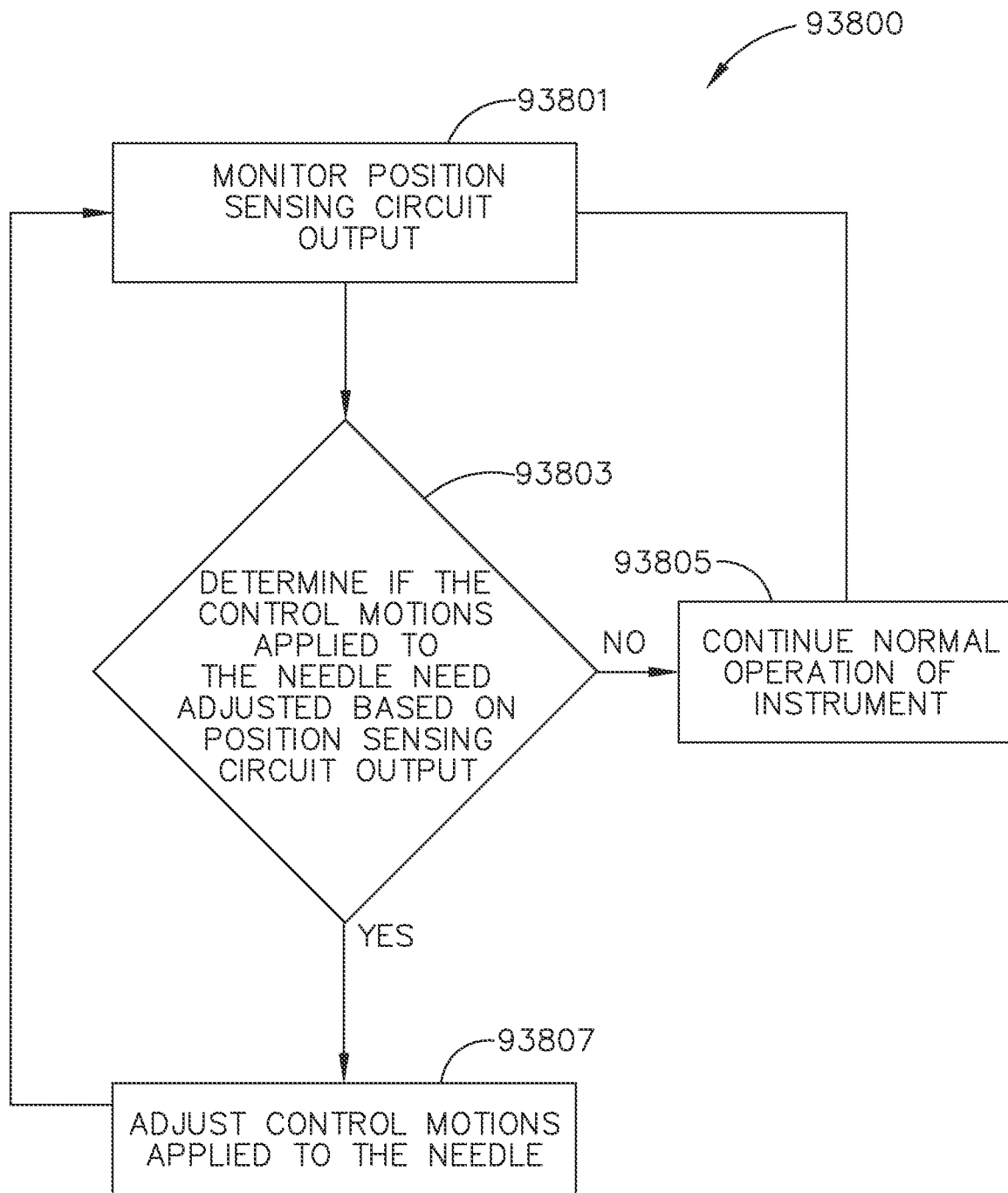
FIG. 9 is a logic diagram of a process depicting a control program for controlling a surgical suturing instrument.

FIG. 9 illustrates a logic flow diagram of a process 93800 depicting a control program for controlling a surgical suturing instrument. The process 93800 comprises monitoring 93801 a position sensing circuit output. For example, the output resistance of the system 91110 can be monitored throughout the operation of a surgical suturing instrument. The process 93800 further includes determining 93803 if the control motions applied to the needle need to be adjusted based on the position sensing circuit output. A processor, for example, can monitor the position sensing circuit output over a period of time and calculate the speed of the needle during its firing stroke. If the speed is too fast or too slow for the present tissue thickness, for example, the control program can adjust 93807 the control motions applied to the needle to change the speed of the needle firing stroke. If the speed of the needle is consistent with a predetermined speed profile for the present tissue thickness, the control program can continue 93805 normal operation of the instrument. Other position sensing systems disclosed herein can be used with this process.

Figure 10:
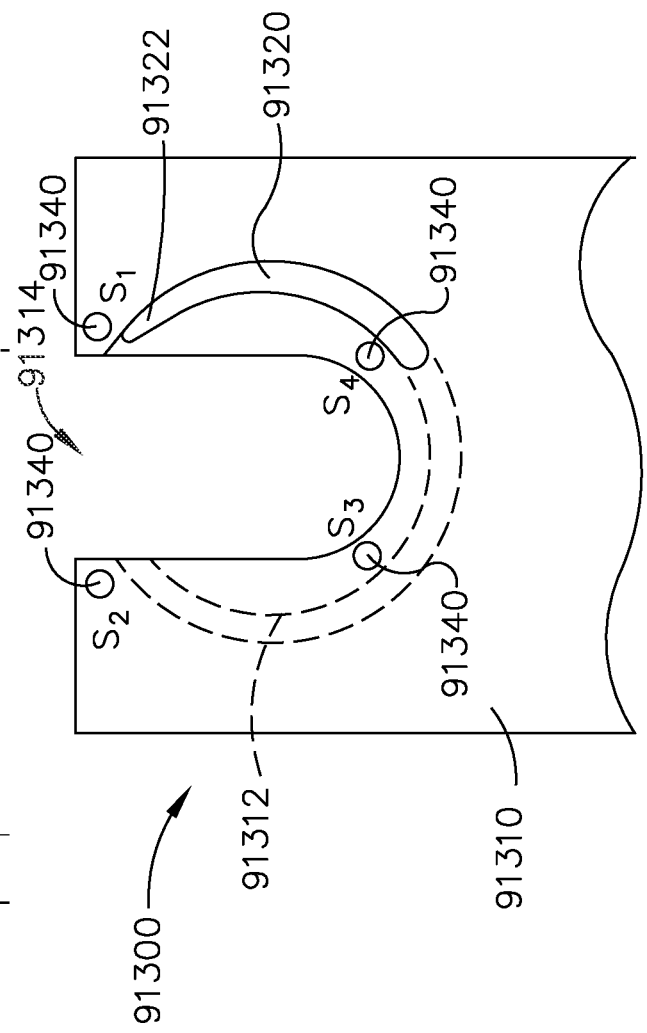
FIG. 10 is a plan view of a suturing device cartridge comprising an adaptive needle driving system.

FIG. 10 depicts a needle sensing system 91300 configured to allow a control system of a suturing instrument to monitor the motions of the needle within the end effector against the anticipated, or expected, motions of the needle. In various instances, backlash in a motor-driven needle drive system, for example, could cause the drive system to produce a shorter needle stroke than expected for a given amount of motor rotations. The needle sensing system 91300 comprises an end effector 91310, a needle track 91312 defined within the end effector 91310, and a needle 91320. Similar to the above, the needle 91320 is configured to be actuated by a needle driver to move the needle 91320 through a circular firing stroke. The needle 91320 is guided by the needle track 91312 as the needle 91320 is actuated by the needle driver. The needle sensing system 91300 comprises a plurality of sensors 91340 designated as S1, S2, S3, and S4 which, as discussed below, are configured to track the motion of the needle 91320. The sensors 91340 may be any suitable position-detecting sensor such that, as the needle 91320 engages, or trips, a sensor 91340, that sensor sends a voltage signal to the control system that the sensor 91340 has detected that the needle 91320 indicating the position of the needle 91320. The needle 91320 comprises a tip 91322 that is configured to initially trip the sensors 91340 as the tip 91322 approaches and contacts, or otherwise trips, the sensors 91340. The end effector 91310 further comprises a tissue opening 91314 defined therein. In use, the end effector 91310 is pressed against the patient tissue such that the tissue enters the opening 91314. At such point, the tip 91322 can pierce tissue in the opening 91314 and then re-enter the needle track 91312 on the other side of the end effector 91310. The needle 91320 is dimensioned to have a larger length than the distance of the opening 91314 so that the needle 91320 can be guided by the needle track 91312 back into the needle track 91312 before a butt end of the needle exits the end effector 91310 into the opening 91314.

Figure 11:
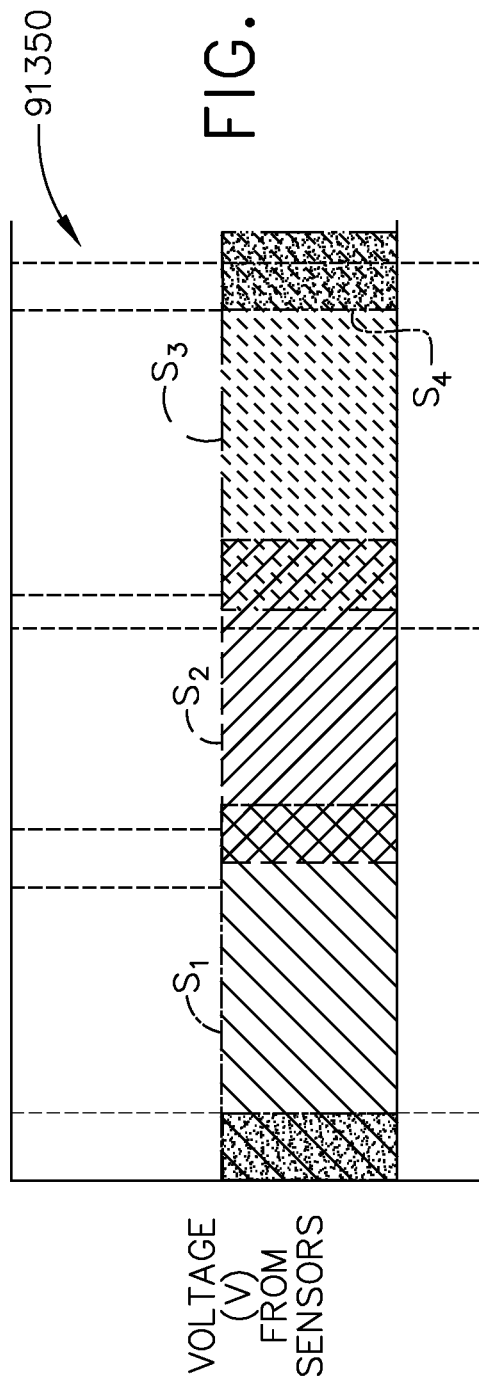
FIG. 11 is a graph of a first aspect of an adaptive needle driving system.

FIG. 11 is a graph 91350 depicting a portion of a needle firing stroke using the needle sensing system 91300 of FIG. 10. As can be seen in the graph 91350 illustrated in FIG. 11, there is an overlap of detection for each neighboring sensor. During a needle firing stroke, each sensor is configured to detect the tip 91322 of the needle 91320 before the previous sensor no longer detects the needle 91320. In another embodiment, more than two sensors are configured to sense the needle during the needle firing stroke.

The sensors 91340 can be used in combination with a control program to ensure that a motor driving the needle 91320 through its firing stroke is driving the needle 91320 the expected amount. For example, a certain amount of rotation from the needle drive motor should produce a corresponding travel length of the needle 91320. Monitoring the position of the needle 91320 in the end effector 91310 along with rotational motion of the motor can provide a way to make sure that the motor is producing the anticipated drive motions of the needle. An example of a needle stroke where the rotational motion of the motor and the actual length of needle travel are monitored is depicted in the graph 91360 illustrated in FIG. 12. If the motion of the needle is not as anticipated, the control system can adjust the power delivered to the motor to account for these differences and assure that the needle is being driven all the way around its firing path during a firing stroke. For example, if the motor takes more rotations than expected to cause the needle to travel a certain distance, the control system can increase the number of rotations for the needle to complete the firing stroke. Such instances could be due to backlash in the drive system, for example.

If the actual motions sensed by a needle position sensing system are not as expected, the control program can place the system in a limp mode, for example, to prevent premature failure of components.

The needle sensing system 91300 can also monitor the current drawn by the needle drive motor while monitoring the input from the sensors 91340. In such an embodiment, a control program can the reverse actuation of the needle 91320 in the event that a substantial increase in current is detected in the motor and the subsequent sensor 91340 has not been tripped—possibly indicating that the needle is jammed. In the same and/or another embodiment, an encoder can be used to measure the number of rotations being provided by the motor. A control program can compare the number of rotations being provided by the motor to the input from the sensors 91340. In an instance where the sensors 91340 are not being tripped as expected by a given amount of rotation from the motor, the control program can interrogate the motor current to assess why the needle is not traveling the expected distance. If the motor current is substantially high, this could indicate a jam, as discussed above. If the motor current is substantially low, this could indicate that the needle and the needle driver are no longer coupled, for example, and that the needle driver is freely moving without driving the needle. In an alternative embodiment, motor torque can be sensed instead of motor current. An example of current monitoring can be seen in the graph 91370 illustrated in FIG. 13.

FIGS. 14-16 depict a surgical suturing instrument 91500 comprising a shaft 91510, an end effector 91530, and a needle drive system 91550. The surgical suturing instrument 91500 is designed to provide a suturing bite width that is larger than the diameter of the shaft 91510 by using an expandable/collapsible needle guide element. Various suturing devices are limited to a bite width that is constrained by the diameter of their shafts. The surgical suturing instrument 91500 comprises a movable needle guide 91560 rotatably mounted to a body 91540 of the end effector 91530 configured to permit the use of a needle 91570, which also comprises a length that exceeds the width of the shaft diameter. To actuate the movable needle guide 91560, a linear actuator 91512 connected to a proximal end 91562 of the movable needle guide 91560 is configured to be pushed and pulled to pivot the movable needle guide 91560 about its pivot point 91562. FIG. 14 illustrates the movable needle guide 91560 in an expanded configuration where the surgical suturing instrument 91500 is ready to be fired. To pivot the movable needle guide 91560 into its closed configuration (FIG. 15), the linear actuator 91512 is pulled proximally. When the movable needle guide 91560 is in its closed configuration, the surgical suturing instrument 91500 is in a configuration sufficient to be passed through a trocar.

The needle drive system 91550 comprises a linear actuator 91520, a proximal needle feed wheel 91552 configured to be rotated about its pivot 91552 by way of the linear actuator 91520 and rotatably mounted within the body 91540 of the end effector 91530, and a distal needle feed wheel 91554 configured to be rotated about its pivot 91555 by a connecting link 91556 by way of the proximal needle feed wheel 91552 and rotatably mounted within the body 91540 of the end effector 91530. The feed wheels 91552, 91554 are configured to be rotated together to move the flexible needle 91570 through the body 91540 of the end effector 91530 and out of the body 91540 of the end effector 91530 against the movable needle guide 91560. The movable needle guide 91560 comprises a curved tip 91563 configured to guide the flexible needle 91570 back into the body 91540 of the end effector 91530 so that the distal needle feed wheel 91554 can begin guiding the flexible needle 91570 back toward the proximal needle feed wheel 91552. The feed wheels 91552, 91554 are connected by a coupler bar such that they rotate at the same time.

In various instances, the needle 91570 may need to be repaired or replaced. To remove the needle 91570 from the end effector 91530, the movable needle guide 91560 may be pivoted outwardly to provide access to the needle 91570 (FIG. 16).

The needle 91570 comprises an arc length A. The distance between the pivots 91553, 91555 of the feed wheels 91552, 91554 is labeled length B. The arc length A of the needle 91570 must be greater than the length B in order to be able to guide the flexible needle 91570 back into the end effector body 91540 with the proximal needle feed wheel 91553. Such an arrangement allows a capture, or bite, width 91580 of the surgical suturing instrument 91500 to be larger than the diameter of the shaft 91510. In certain instances, a portion of the end effector containing the needle drive system 91550 can be articulated relative to the end effector body 91540 so that the capture width, or opening, 91580 can hinge outwardly and face tissue distally with respect to the instrument 91500. This arrangement can prevent a user from having to preform the suturing procedure with respect to the side of the instrument 91500. Such a feature may utilize a hinge mechanism with snap features to rigidly hold the end effector body 91540 in a firing position as opposed to a position suitable for insertion through a trocar.

As outlined above, a portion of the end effector 91530 is movable to increase or decrease the width of the end effector 91530. Decreasing the width of the end effector 91530 allows the end effector 91530 to be inserted through a narrow trocar passageway. Increasing the width of the end effector 91530 after it has been passed through the trocar allows the end effector 91530 to make larger suture loops in the patient tissue, for example. In various instances, the end effector 91530 and/or the needle 91570 can be flexible so that they can be compressed as they are inserted through the trocar and then re-expand once they have passed through the trocar. Such an arrangement, as described above, allows a larger end effector to be used.

Figure 17:
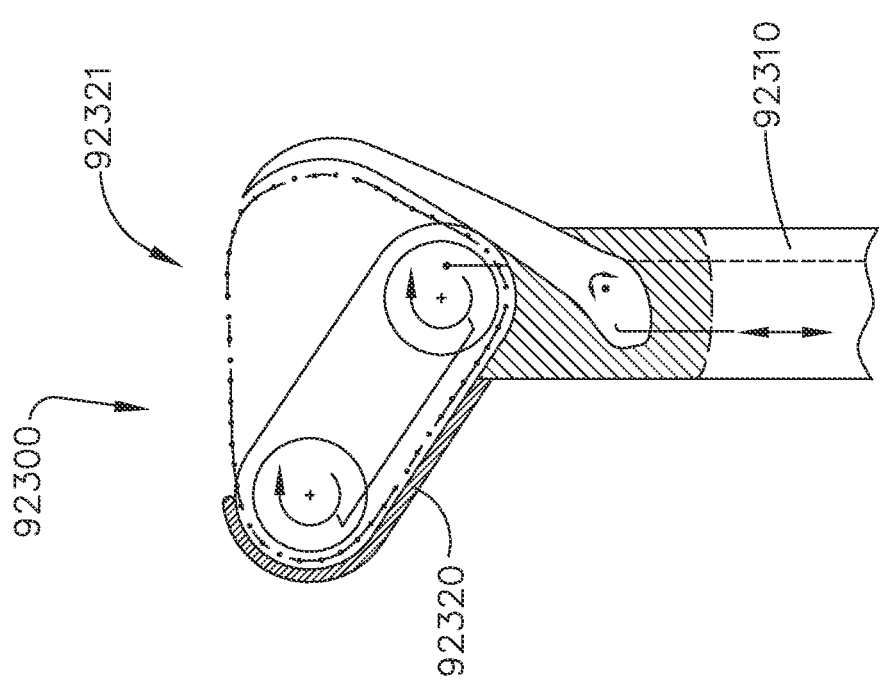
FIG. 17 is a plan view of a collapsible suturing device comprising a shaft and an end effector configured to be articulated relative to the shaft, wherein the end effector comprises a needle driving system comprising a movable needle guide.

FIG. 17 depicts a collapsible suturing device 92300 comprising a shaft 92310 and an end effector 92320 configured to be articulated relative to the shaft 92310. The device 92300 comprises a tissue bite region having a larger width than its shaft diameter. The end effector 92320 is hingedly coupled to the shaft 92310. The collapsible suturing device 92300 comprises a separate actuation member to rotate the end effector 92320 relative to the shaft 92310. In other embodiments, the end effector 92320 can be spring biased into a straight configuration where a user may apply torque to a distal end of the end effector 92320 by pressing the end effector 92320 against tissue to rotate the end effector 92320 relative to the shaft 92310. In either event, such an arrangement provides the device 92300 with a distal-facing tissue bite region 92321 which can permit a user to more accurately and/or easily target tissue to be sutured.

The tissue bite region 92321 is larger than the diameter of the shaft 92310. During use, a user would insert the collapsible suturing device 92300 into a trocar while the device 92300 is in its straight configuration. After the device 92300 is inserted through the trocar, the user may actively rotate the end effector 92320 with an actuator to orient the end effector 92320 properly to prepare to suture the tissue. Once the end effector 92320 is oriented to face the tissue to be sutured, a movable needle guide may be actuated outwardly to prepare to advance the needle through a needle firing stroke. In this configuration, the end effector 92320 can then be pressed against the tissue to be sutured and the needle can be advanced through a needle firing stroke. Once suturing is complete, the needle guide can be collapsed and the end effector 92320 can be rotated back into its straight configuration to be removed from the patient through the trocar. The needle may be taken out of the end effector 92320 before or after the end effector 92320 has passed back out of the patient through the trocar.

Figure 18:
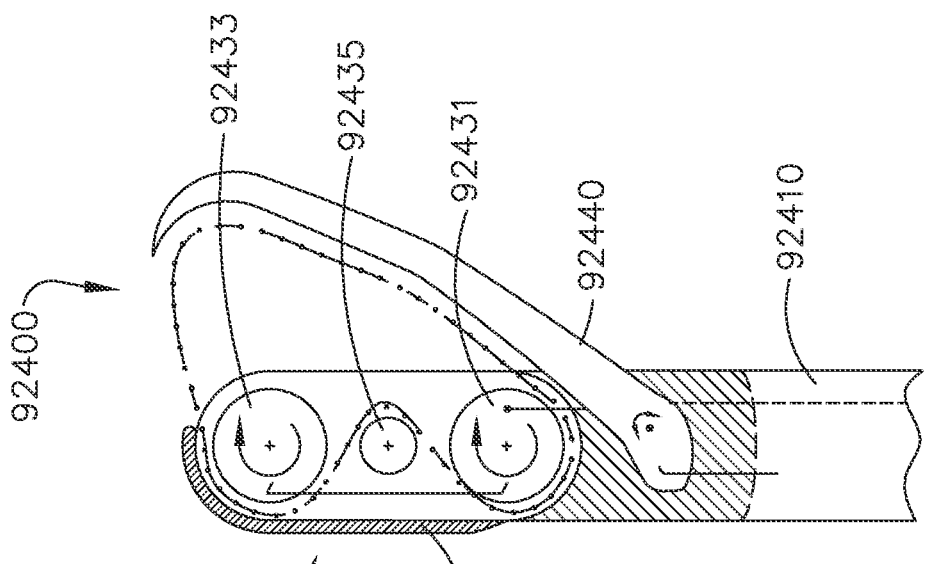
FIG. 18 is a plan view of a collapsible suturing device comprising a needle driving system comprising a movable needle guide and an intermediate feed wheel.

FIG. 18 depicts a collapsible suturing device 92400 comprising a shaft 92410 and an end effector 92420 attached to the distal end of the shaft 92410. The device 92400 comprises a tissue bite region having a larger width than its shaft diameter. The end effector 92420 further comprises a needle driving system 92430 configured to drive a flexible needle through a needle firing stroke against a movable needle guide 92440. The needle driving system 92430 comprises a proximal feed wheel 92431, a distal feed wheel 92433, and an intermediate feed wheel 92435 configured to feed the flexible needle through the end effector 92420. The intermediate feed wheel 92435 permits the use of a longer flexible needle than arrangements without an intermediate feed wheel. Embodiments are envisioned where the intermediate feed wheel is actively connected the needle driving system. In other instances, the intermediate feed wheel is an idler component and rotates freely. In at least one embodiment, the needle comprises a width that is larger than the width of the shaft with which is used.

Figure 19:
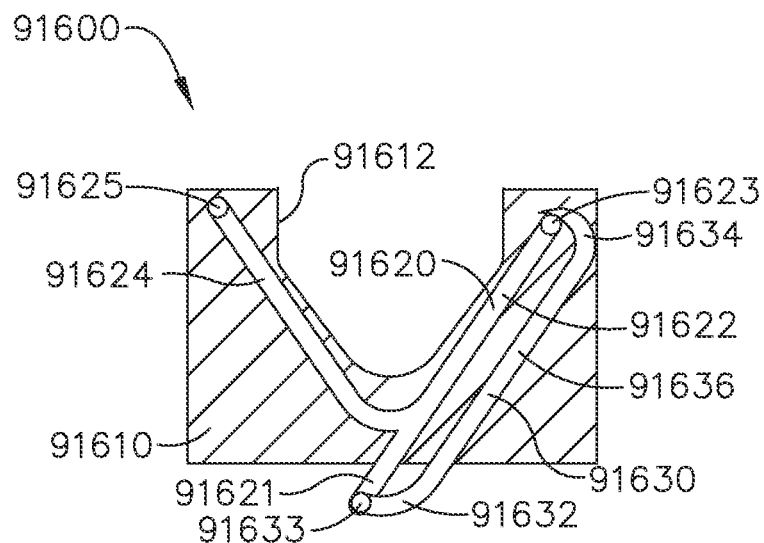
FIG. 19 is a cross-sectional view of an end effector of a suturing device comprising a body portion, a needle track defined within the body portion, and a suturing needle, wherein the suturing needle is in a parked position.
Figure 20:
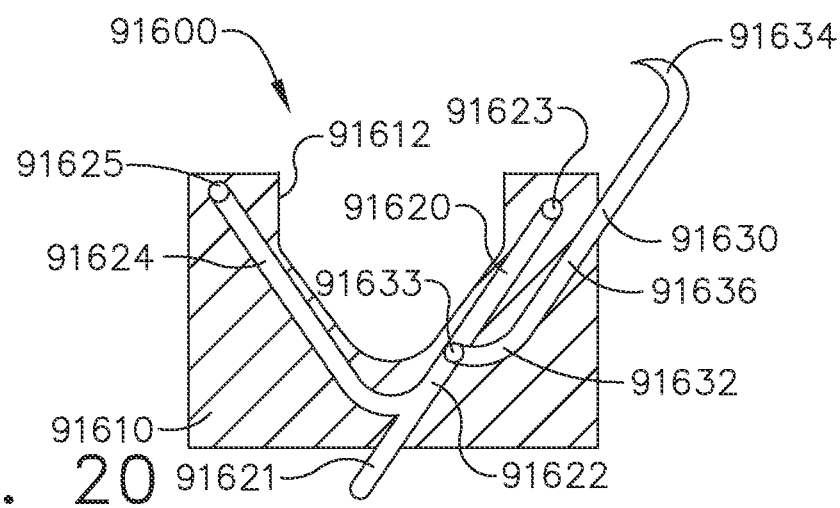
FIG. 20 is a cross-sectional view of the end effector of FIG. 19, wherein the suturing needle is in a ready-to-fire position.
Figure 21:
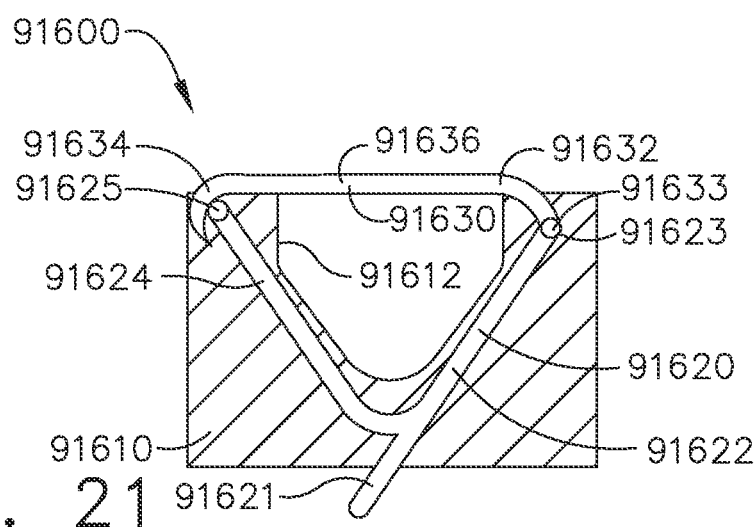
FIG. 21 is a cross-sectional view of the end effector of FIG. 19, wherein the suturing needle is in a partially-fired position.

FIGS. 19-21 depict a surgical suturing end effector 91600 configured to provide a suturing device with a variable needle stroke. In various instances, the needle stroke of the end effector 91600 can be different every time the end effector 91600 is fired. The end effector 91600 also can provide a suturing bite width that is wider than the diameter of its shaft. The surgical suturing end effector 91600 comprises a body portion 91610 having a tissue-engaging opening 91612, a needle track 91620 defined within the body portion 91610, and a needle 91630 configured to be guided through a firing stroke by the needle track 91620. FIG. 19 illustrates the needle 91630 in its parked position where the end effector 91600 can be passed through a trocar. Once the end effector 91600 is passed through a trocar, the needle 91630 is advanced linearly from a park track portion 91621 of the needle track 91620—by way of its proximal end 91633—to a ready-to-fire position (FIG. 20). As can be seen in FIG. 20, the needle 91630 extends outwardly beyond the body 91610 of the end effector 91600 when the needle 91630 is in its ready-to-fire position. Such an arrangement allows for an instrument to have a tissue bite width that is larger than the diameter of the instrument's shaft. The needle 91630 comprises a canoe-like shape but can comprise any suitable shape to achieve this.

When a clinician wants to complete a suture stroke, discussed in greater detail below, the needle 91630 is moved to the position shown in FIG. 21 referred to as the hand-off position. To get to this position, the proximal end 91633 of the needle 91630 is rotated and advanced linearly within a first track portion 91622 of the track 91620 until the proximal end 91633 of the needle 91630 reaches a distal end 91623 of the first track portion 91622 and a tip portion 91634 of the needle 91630 engages a distal end 91625 of a second track portion 91624 of the track 91620. This engagement allows a needle driver that rotates and linearly advances the needle 91630 within the track 91620 to move along the track 91620 to the distal end 91625 of the second track portion 91624 to grab the tip portion 91634 and pull the needle 91630 through the end effector 91600 by pulling the needle 91630 proximally and rotating the needle 91630 to prepare for a second firing stroke of the needle 91630. At a certain point after the needle 91630 attains the hand-off position (FIG. 21), the needle driver can re-connect, or re-engage, with the proximal end 91633 of the needle 91630 to begin a second firing stroke to return the needle 91630 to its ready-to-fire position illustrated in FIG. 20. The firing stroke of the needle 91630, having a canoe-like shape, can resemble a box-shaped, or diamond-shaped, path.

Figure 22:
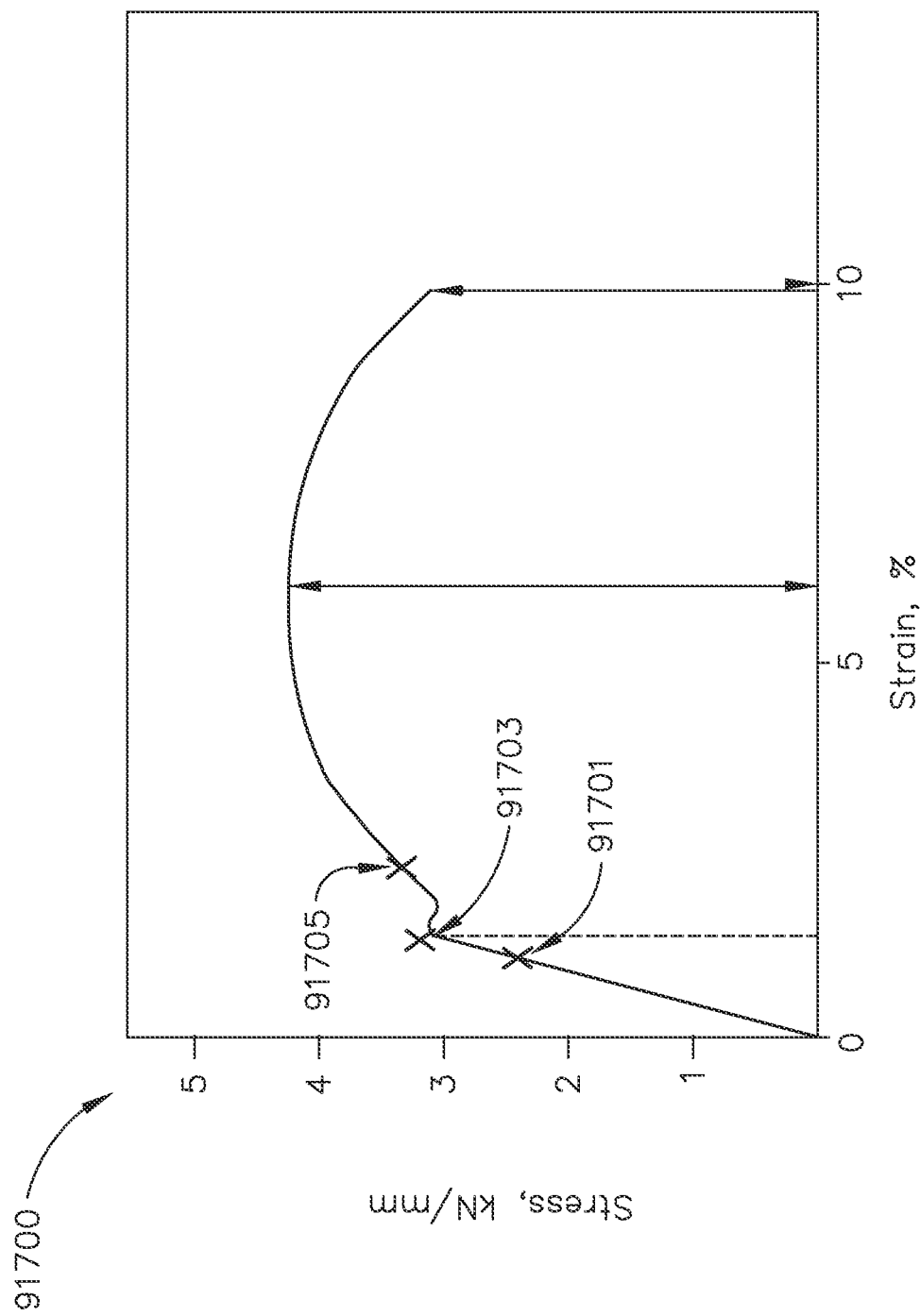
FIG. 22 is a diagram illustrating a relationship between stress and strain of a component of an end effector and corresponding identifiable events during the use of the end effector.

FIG. 22 is a stress-strain diagram 91700 of the loads experienced by a needle during a firing stroke. A control system of a surgical suturing instrument can monitor input from a strain gauge and adjust the operation of the surgical suturing instrument based on the monitored strain and/or display the strain to a user during use. The surgical suturing instrument can alert a user when the needle has reached 75% 91701 of its yield strength during a suturing procedure. The surgical instrument can provide the clinician with an option to adjust the advancement speed of the needle to help prevent further spikes of the strain and/or stress within the needle. If the needle reaches 100% 91703 of its yield strength, overstress may be reported to the user and the control system will report the overstress to the system disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein. If the needle reaches 125% 91705 of its yield strength, the user is alerted of this threshold and the control program automatically slows the speed and may disable the instrument from actuating the needle any further, and/or request action to be taken before any further use of the surgical suturing instrument.

Figure 23:
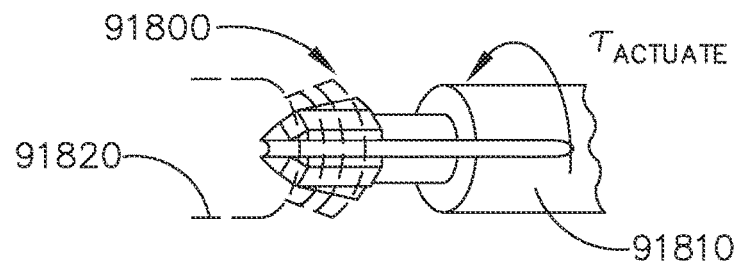
FIG. 23 is a partial perspective view of a surgical instrument system comprising an actuation interface and a modular shaft to be actuated with the actuation interface, wherein the surgical instrument system is shown in a partially attached configuration.
Figure 24:
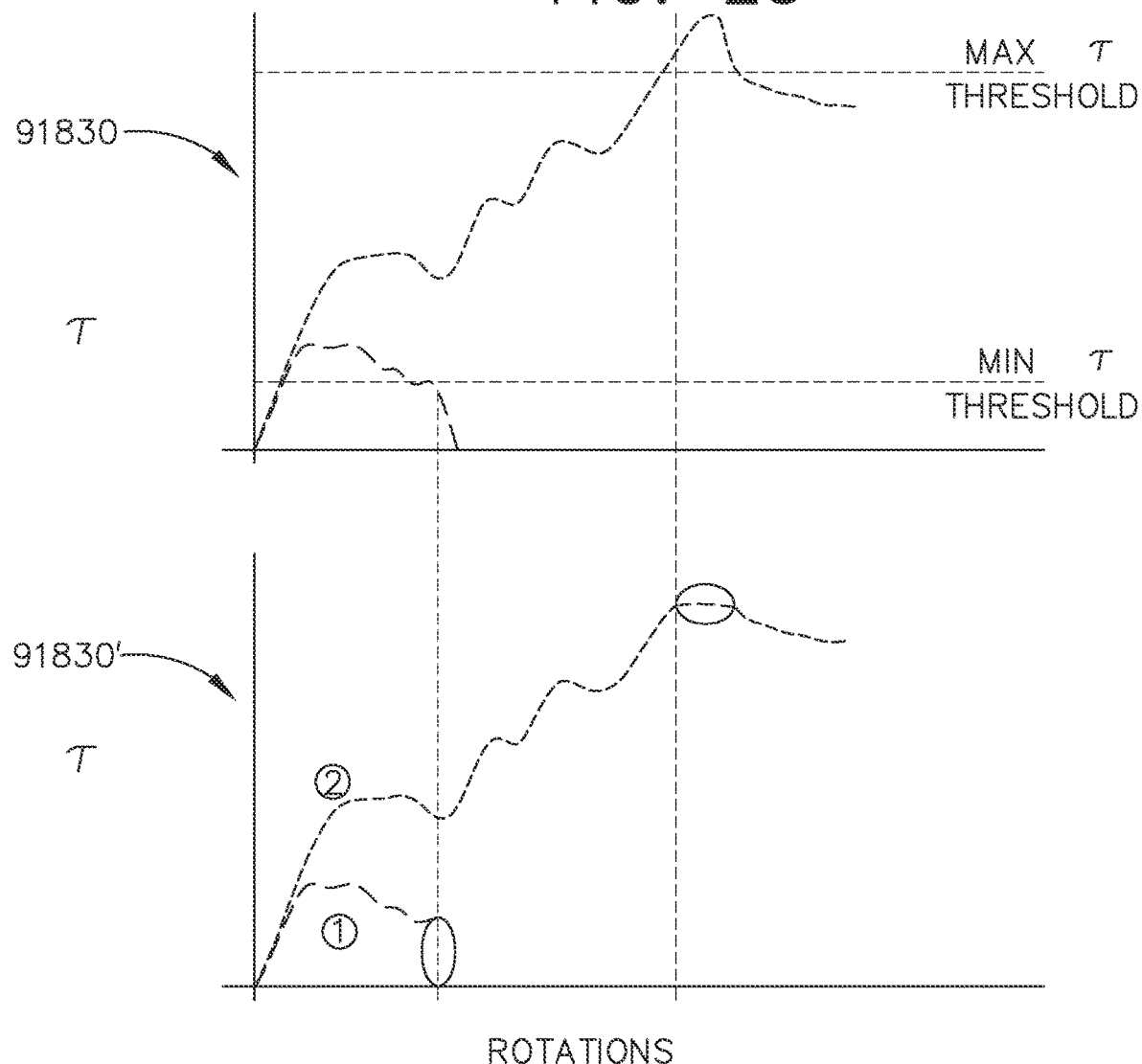
FIG. 24 is a graph illustrating a sensed torque of the surgical instrument system of FIG. 23 and a sensed current of a motor of the surgical instrument system of FIG. 23.

FIGS. 23 and 24 depict a method for detecting the proper and/or improper attachment of a modular shaft to a surgical instrument handle and/or surgical robot, for example. FIG. 23 depicts an attachment assembly 91800 attachable to an attachment interface 91810—which can be a surgical instrument handle and/or robotic attachment, or control, interface. Monitoring the torque of a drive system coupled at the attachment interface 91810 can provide a way to determine if the attachment interface 91810 and the modular attachment 91820 have been successfully attached or not.

Referring to the graph 91830, the solid plot line represents a scenario where an attempt at attaching the modular attachment 91820 to the attachment interface 91810 was made, and the modular attachment 91820 and the attachment 91830 slipped out of engagement thereby causing a reduction in torque of the actuation drive system below a minimum torque threshold representing an unsuccessful attachment and engagement of drive systems. The torque of a failed attempt is noticeably different than the torque of a successful attempt which is also illustrated in the graph 91830. In another embodiment, the current of the motor that drives the drive system can be directly monitored. Referring now to the graph 91830', the surgical instrument is equipped with a control system that shuts off the motor in this scenario (1) when the torque sensed drops below the minimum threshold torque. The control system can also alert a user that the motor has been stopped because attachment was not successful. Referring again to the graph 91830, a second scenario is illustrated by a dashed plot line where attachment is made, however, the torque sensed increases above a maximum torque threshold. This could indicate a jam between the attachment interface 91810 and the modular attachment 91820. Referring again to the graph 91830', the surgical instrument is equipped with a control system that limits the torque delivered by the drive system when the torque sensed increases above the maximum threshold torque, as illustrated in the dashed plot line representing the second scenario (2). Such a limiting of torque delivery can prevent the breaking of components in the modular attachment 91820 and/or the attachment interface 91810.

In various embodiments, strain gauges can be fitted to frame elements of the modular attachments to monitor force applied to tissue with the frame elements themselves. For example, a strain gauge can be fitted to an outer shaft element to monitor the force experienced by the shaft as the modular attachment is pushed against tissue and/or as the modular attachment pulls tissue. This information can be communicated to the user of the instrument so that the user is aware of the pressure being applied to the tissue by the grounded elements of the modular attachment due to manipulation and movement of the modular attachment within the surgical site.

Figure 25:
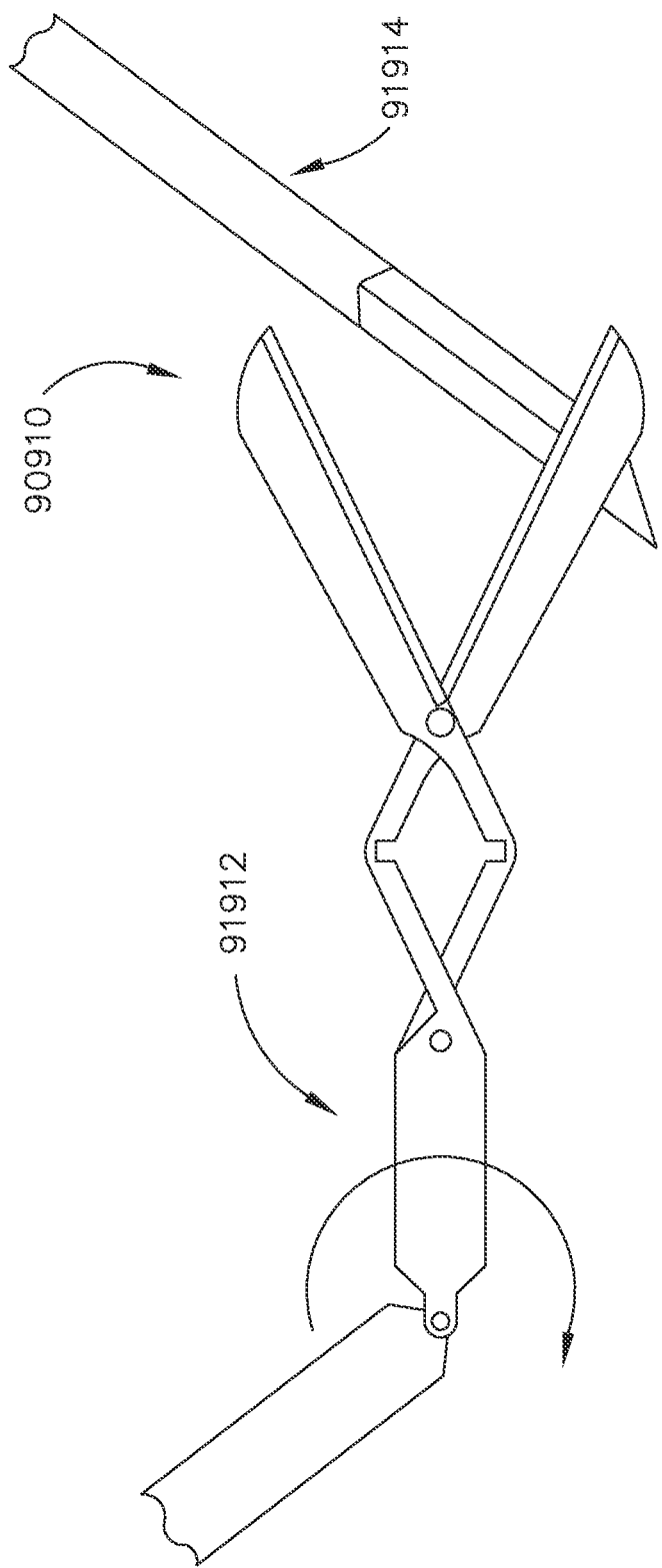
FIG. 25 is a partial perspective view of a surgical grasper and a mono-polar bridge instrument.
Figure 26:
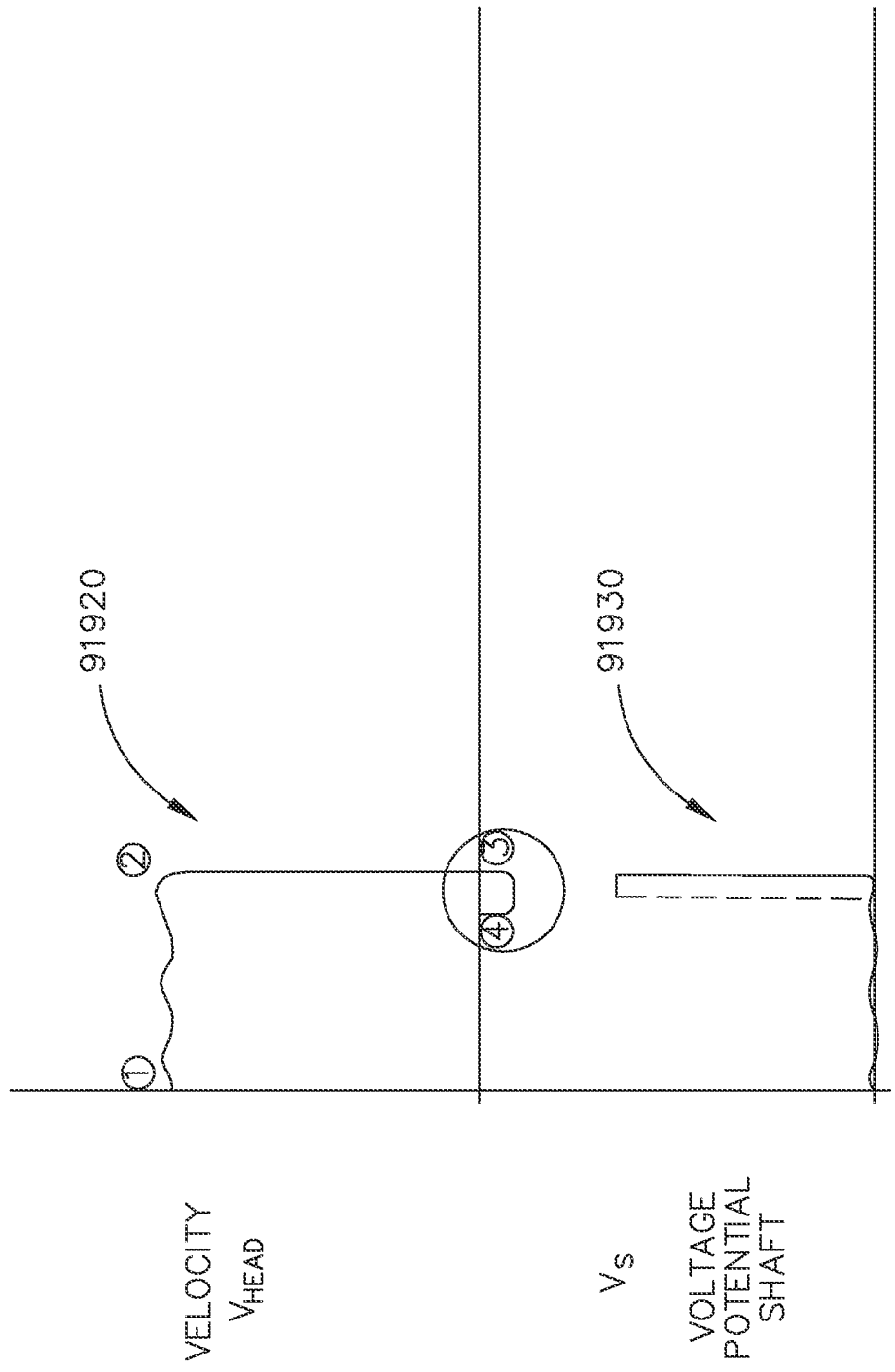
FIG. 26 is a graph illustrating a reactive algorithm of the surgical grasper of FIG. 25.

FIGS. 25 and 26 depict a surgical instrument system 91910 that is configured to monitor unexpected electrical potential applied to a surgical instrument during an operation that involves using a mono-polar bridge instrument. FIG. 25 depicts a system 91910 comprising a grasper 91912 and a mono-polar bridge instrument 91914 being used in the same surgical site. In one scenario, now referring to the graph 91930 in FIG. 26, the voltage potential of the grasper 91912 can be monitored throughout the use of the system 91910 during an operation. Stage (1) of the graph 91920 represents the beginning of articulation of the grasper 91912 using motorized articulation. Stage (2) represents a spike in detected voltage potential of the grasper 91912. Such a spike in voltage potential can be conducted to the grasper 91912 by way of the mono-polar bridge instrument 91914. At this stage, the system 91910 can automatically reverse the motor direction Stage (3) of articulation to move the grasper 91912 away from the mono-polar bridge instrument 91914 until the unexpected voltage spike subsides Stage (4). The control program of the system 91910 can then instruct the articulation motor to automatically reverse the articulation a predetermined amount passed the point when the system 91910 no longer detects the voltage spike to ensure that this voltage spike will not occur again due to minor inadvertent movement of either the grasper 91912 and/or the mono-polar bridge instrument 91914.

The surgical instrument can also alert the user when an unexpected voltage potential is detected and await further action by a user of the instrument. If the user is using the instrument that experiences the voltage spike as a mono-polar bridge instrument then the user could inform the instrument of this to continue actuation of the instrument. The instrument can also include an electrical circuit, or ground path, to interrupt the flow of electricity beyond a dedicated position when the instrument experiences an unexpected voltage potential. In at least one instance, the ground path can extend within a flex circuit extending throughout the shaft.

Figure 27:
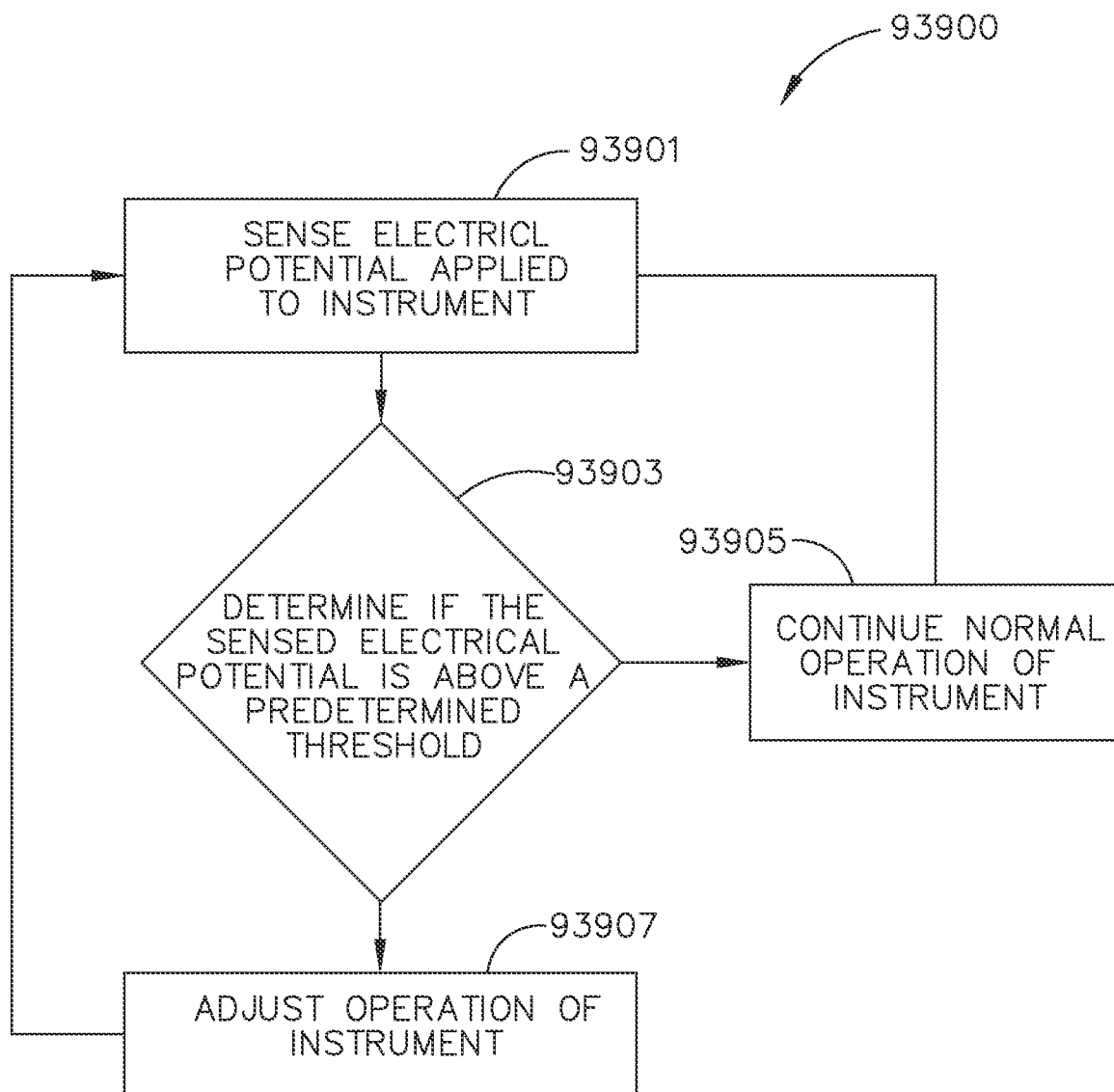
FIG. 27 is a logic diagram of a process depicting a control program for controlling a surgical instrument.

FIG. 27 illustrates a logic diagram of a process 93900 depicting a control program for controlling a surgical instrument. The process 93900 comprises sensing 93901 an electrical potential applied to the instrument. For example, the voltage of an electrical circuit which includes the instrument can be monitored. The process 93900 further includes determining 93903 if the sensed electrical potential is above a predetermined threshold based on the sensed electrical potential. A processor, for example, can monitor the voltage and, if a voltage spike occurs, the processor can change the operation of the surgical instrument. For instance, the process can adjust 93907 the control motions of the instrument such as reversing a previous motion, for example. If the sensed electrical potential is below the predetermined threshold, the control program can continue 93905 the normal operation of the instrument.

In various embodiments, surgical suturing instruments can include means for detecting the tension of the suture during the suturing procedure. This can be achieved by monitoring the force required to advance a needle through its firing stroke. Monitoring the force required to pull the suturing material through tissue can indicate stitch tightness and/or suture tension. Pulling the suturing material too tight during, for example, tying a knot can cause the suturing material to break. The instrument can use the detected forces to communicate stitch tightness to the user during a suturing procedure and let the user know that the stitch is approaching its failure tightness or, on the other hand, is not tight enough to create a sufficient stitch. The communicated stitch tightness can be shown to a user during a suturing procedure in an effort to improve the stitch tightness throughout the procedure.

In various embodiments, a surgical suturing instrument comprises a method for detecting load within the end effector, or head, of the instrument, and a control program to monitor this information and automatically modify, and/or adjust, the operation of the instrument. In one instance, a needle holder and/or a needle drive can comprise a strain gauge mounted thereon to monitor the force and stress being experienced by the needle during its firing stroke. A processor of the instrument can monitor the strain sensed by the strain gauge by monitoring the voltage reading that the strain gauge provides and, if the force detected is above a predetermined threshold, the processor can slow the needle and/or alert a user of the instrument that the needle is experiencing a force greater than a certain threshold. Other parameters, such as needle velocity and/or acceleration, for example, can be monitored and used to modify the operation of the surgical instrument.

Figure 28:
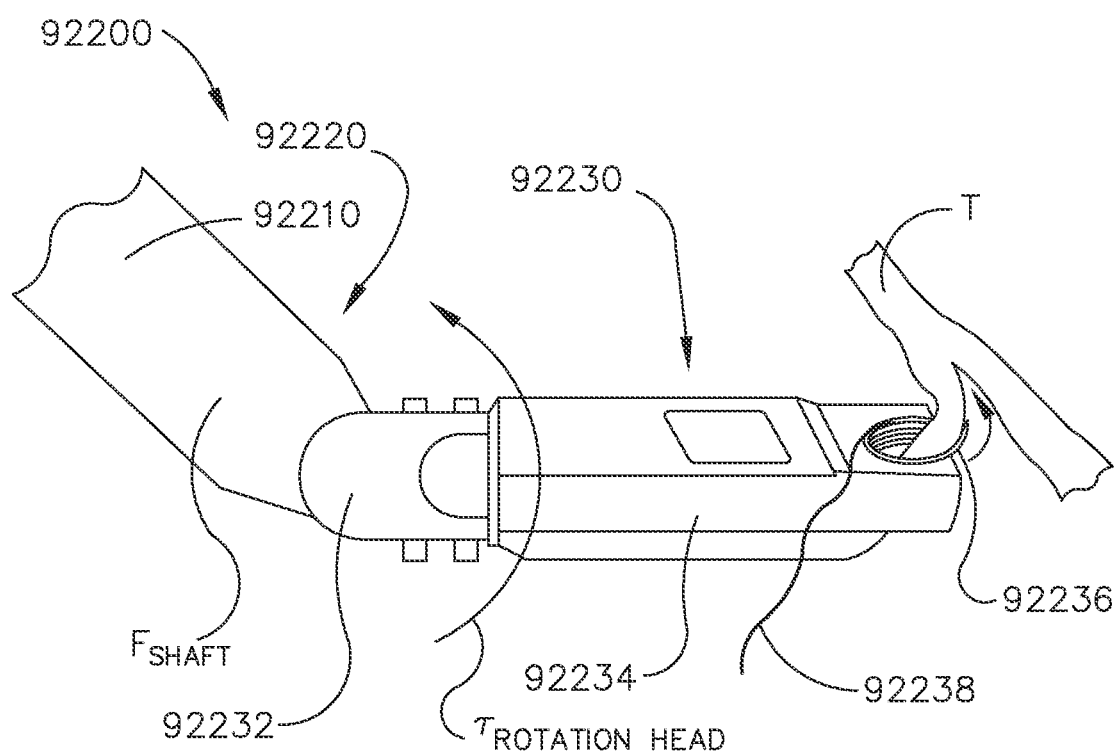
FIG. 28 is a partial perspective view of a surgical suturing instrument.

Many different forces experienced by a surgical suturing instrument can be monitored throughout a suturing procedure to improve efficiency of the operation. FIG. 28 depicts a surgical suturing instrument 92200 comprising a shaft 92210, an end effector 92230, and an articulation joint 92220 attaching the end effector 92230 to the shaft 92210 and permitting articulation of the end effector 92230 relative to the shaft 92210. The end effector 92230 comprises a frame 92232 and a suture cartridge 92234. The cartridge 92234 comprises a needle 92236 comprising suturing material 92238 attached thereto configured to pass through tissue T.

Figure 29:
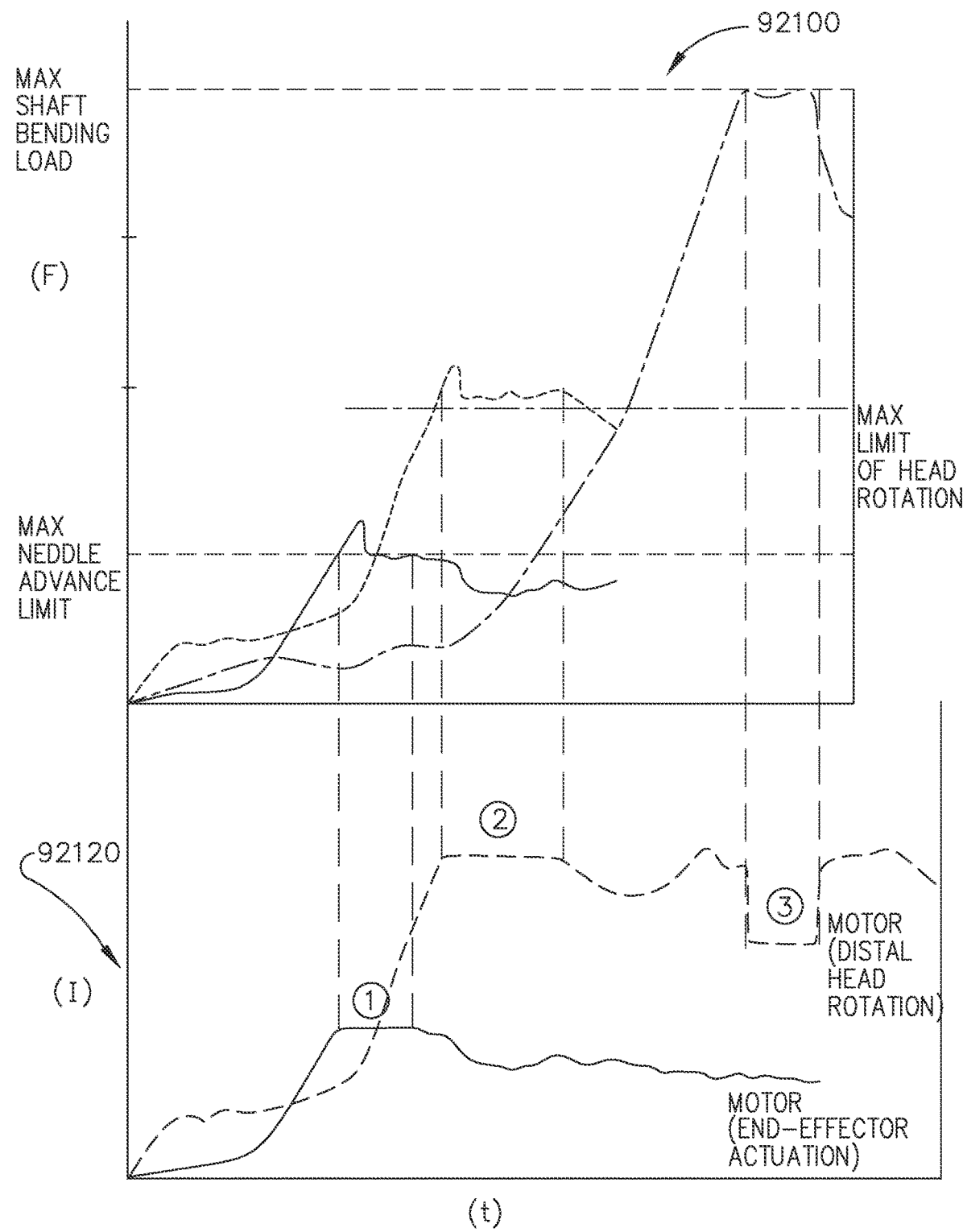
FIG. 29 is a graph depicting sensed parameters of the surgical suturing instrument of FIG. 28 and also depicting an algorithm for the surgical suturing instrument to react to the sensed parameters.

Various parameters of the instrument 92200 can be monitored during a surgical suturing procedure. The force, or load, experienced by the needle 92236 can be monitored, the torque load that resists distal head rotation of the end effector 92230 can be monitored, and/or the bending load of the shaft 92210 that can cause drive systems within the shaft to bind up can be monitored. The monitoring of these parameters is illustrated in the graph 92100 in FIG. 29. The surgical instrument 92200 is configured to limit corresponding motor current if certain thresholds of the parameters are exceeded. The force experienced by the needle 92236 is represented by the solid plot line in the graph 92100. This force can directly correspond to the current drawn by the motor that fires the needle 92236. As the load on the needle 92236 increases, the motor that is firing the needle slows down thereby reducing the load on the needle and reducing current through the motor. If this force, or current, exceeds a certain pre-determined threshold, the power applied to the needle firing motor can be limited to prevent possible failure of drive system components and/or driving a needle through an unintended target. This limiting event is labeled (1) in the reaction graph 92120. The torque load experienced by the end effector 92230 is represented by the dashed plot in the graph 92100. This torque load can be a result of trying to rotate the end effector 92230 while the suturing material 92238 is still connected to tissue T and the needle 92236. This torque load can directly correspond to the current of the motor that rotates the end effector 92230. If this torque load, or current, exceeds a certain pre-determined threshold, power to the motor that rotates the end effector 92230 can be limited. This limiting event is labeled (2) in the reaction graph 92120. The bending load experienced by the shaft 92210 is represented by the dash-dot plot in the graph 92100 and can be sensed by using a strain gauge placed on the shaft 92210, for example. If this bending load exceeds a certain pre-determined threshold, power to the motor that rotates the end effector 92230 can be limited and reduced. This limiting event is labeled (3) in the reaction graph 92120.

Figure 30:
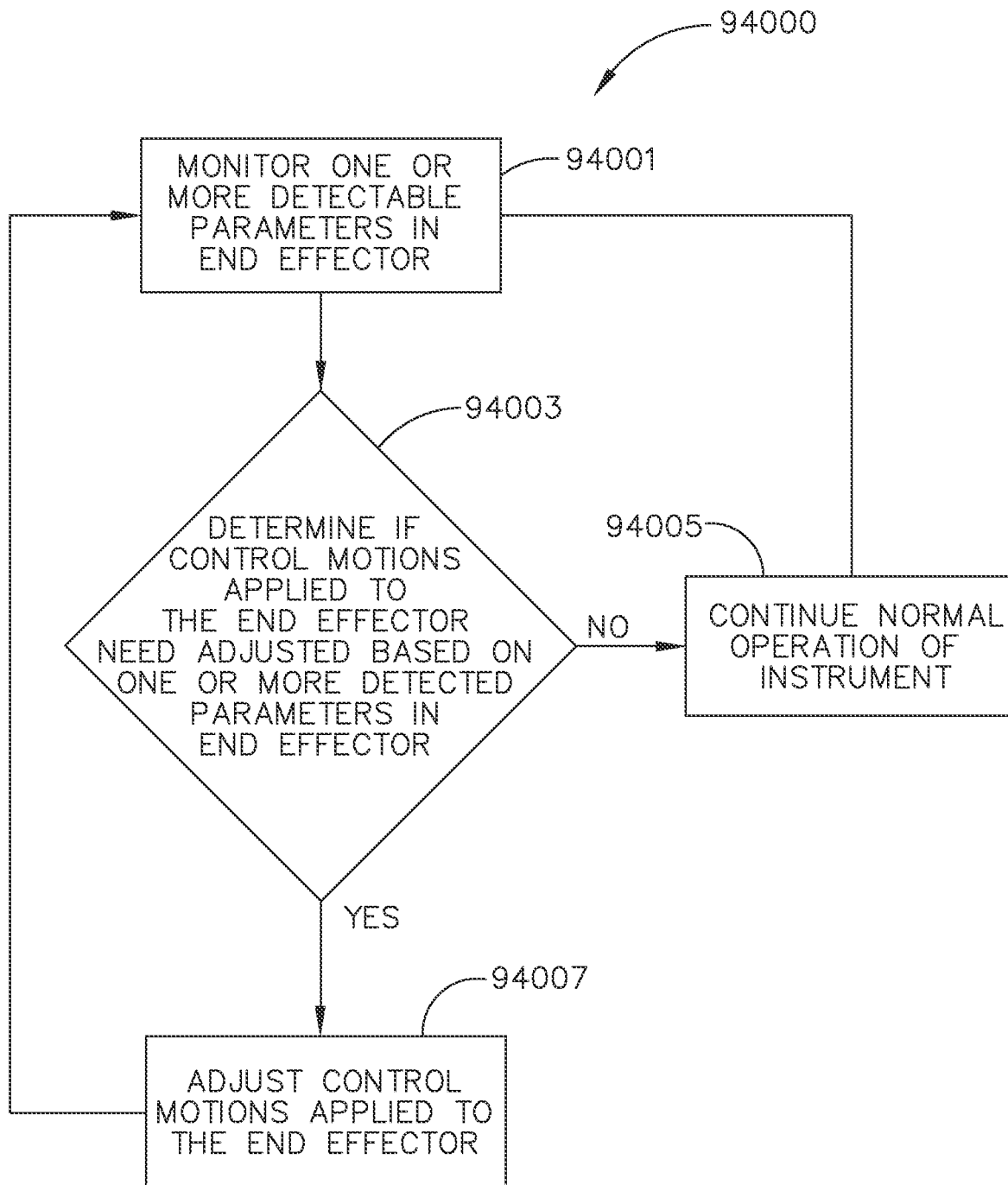
FIG. 30 is a logic diagram of a process depicting a control program for controlling a surgical suturing instrument.

FIG. 30 illustrates a logic diagram of a process 94000 depicting a control program for controlling a surgical suturing instrument. The process 94000 comprises monitoring 94001 one or more detectable parameters of the surgical suturing instrument. For example, the force experienced by the suturing needle, the torque load experienced by the shaft of the instrument, and/or the torque load experienced by the end effector of the instrument can be monitored. In fact, any combination of detectable parameters can be monitored. The process 94000 further includes determining 94003 if the detected parameters warrant a change in the operation of the instrument. For example, if the shaft is experiencing a torque load that is greater than a predetermined threshold, the control program can adjust 94007 the control motions applied to the end effector, such as stopping the actuation of the instrument, until the torque experienced by the shaft falls below the predetermined threshold. If all of the detected parameters are within operational conditions, the control program can continue 94005 the normal operation of the instrument.

Another system for detecting and/or monitoring the location of the suturing needle during its firing stroke can include utilizing one or more magnets and Hall Effect sensors. In such an embodiment, a permanent magnet can be placed within and/or on the needle and a Hall Effect sensor can be placed within, or adjacent to, the needle track, for example. In such an instance, movement of the needle will cause the magnet to move into, within, and/or out of the field created by the Hall Effect sensor thereby providing a way to detect the location of the needle. In the same embodiment, and/or in another embodiment, a magnet can be placed on one side of the needle track and a corresponding Hall Effect sensor can be placed on the other side of the needle track. In such an embodiment, the needle itself can interrupt the magnetic field between the magnet and the Hall Effect sensor as the needle passes between the two magnets, thereby providing a way to detect the location of the needle.

Figure 31:
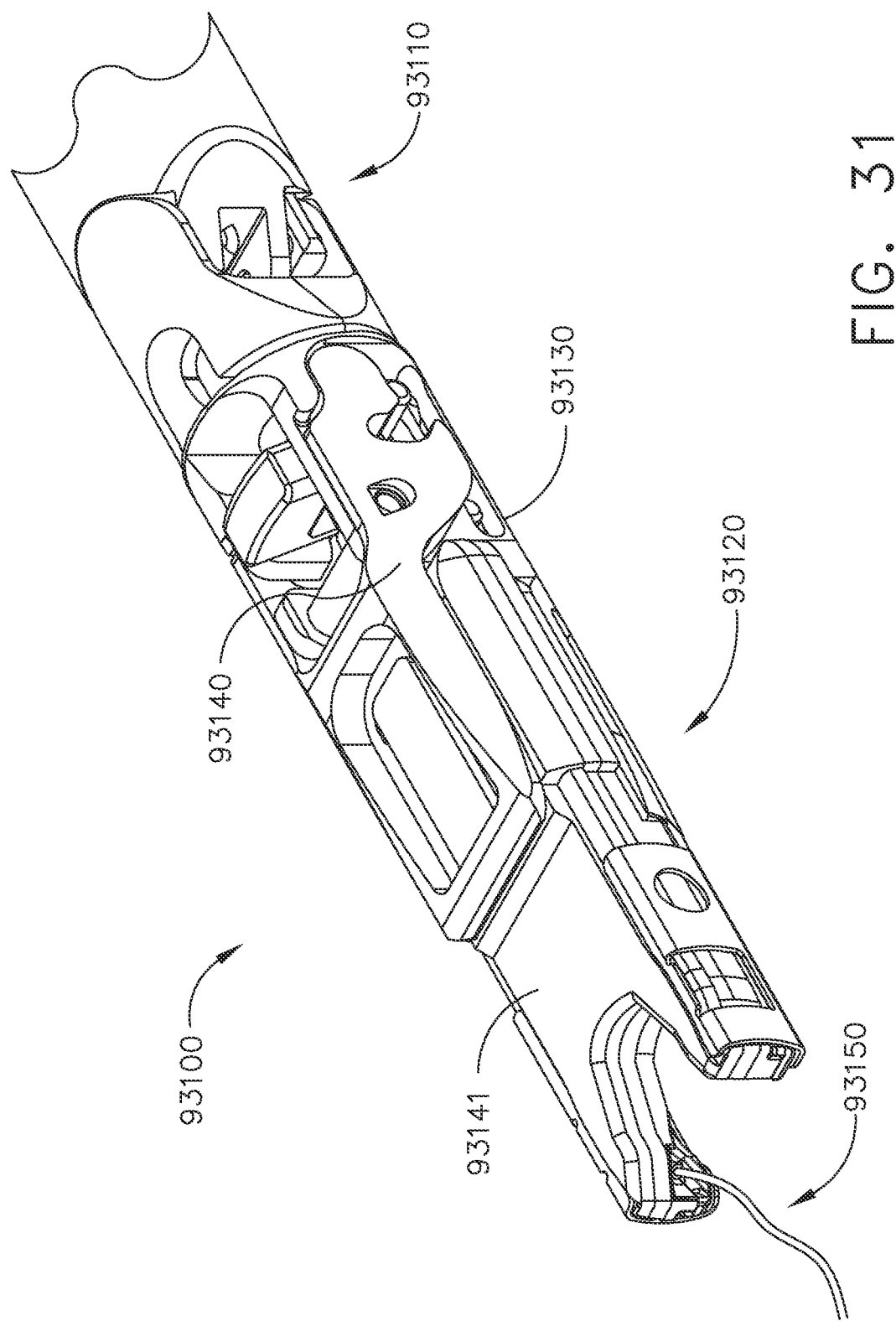
FIG. 31 is a perspective view of an end effector assembly comprising a suture cartridge.
Figure 32:
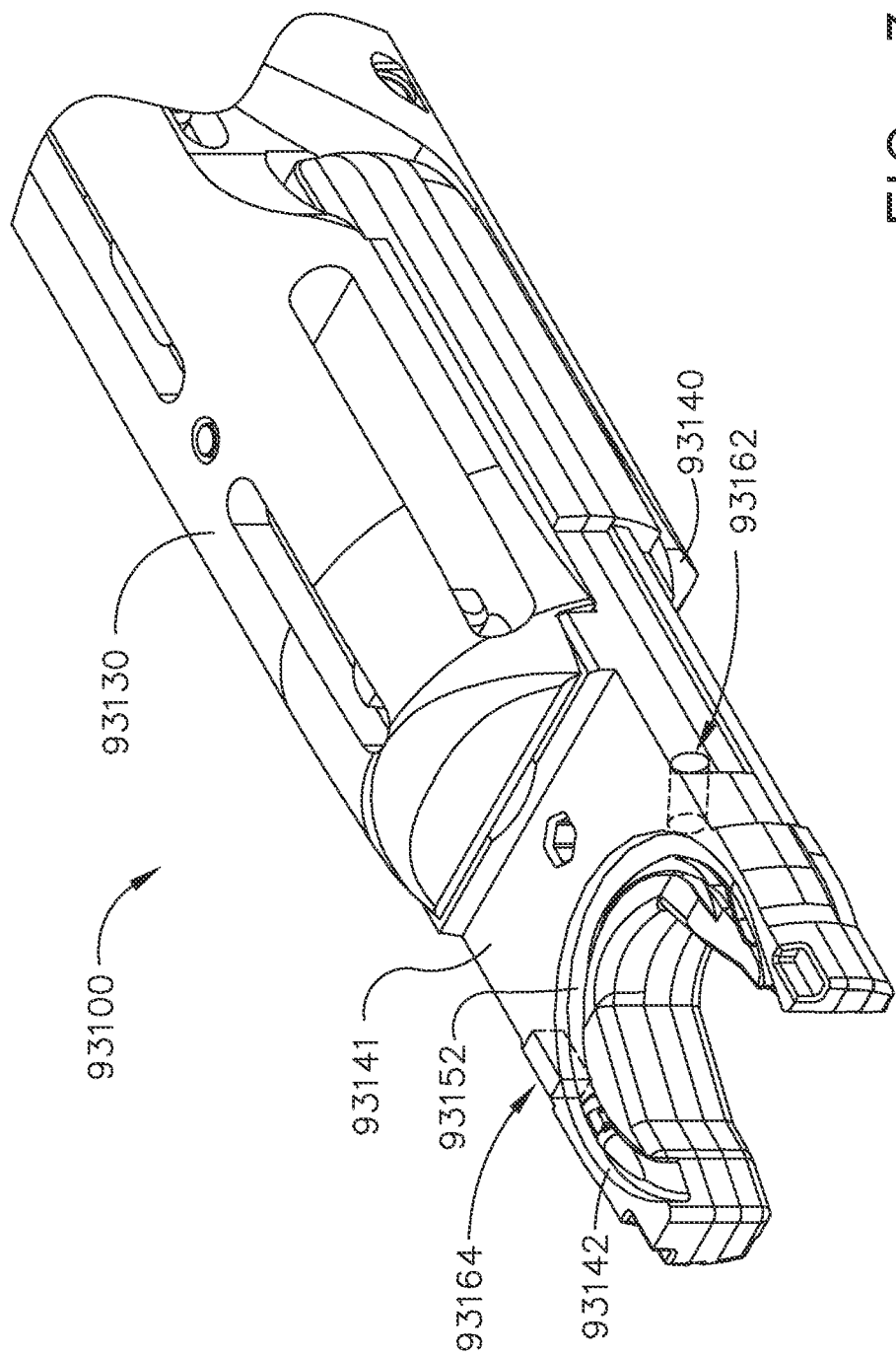
FIG. 32 is a partial perspective view of the end effector assembly of FIG. 31.

FIGS. 31 and 32 depict a surgical suturing end effector assembly 93100 configured to suture the tissue of a patient during a surgical suturing procedure. The end effector assembly 93100 comprises a shaft 93110 and an end effector 93120 extending distally from the shaft 93110. The end effector 93120 comprises a first jaw 93130 and a second jaw 93140 configured to receive a replaceable suturing cartridge 93141 therein. The suturing cartridge 93141 comprises a needle 93152 and suture material 93150 attached thereto configured to be driven through a needle firing stroke and guided by a needle track 93142 in the suturing cartridge 93141.

The surgical suturing end effector assembly 93100 further comprises a needle sensing system comprising a magnet 93162 and a Hall Effect sensor 93164. The magnet 93162 and Hall Effect sensor 93164 are positioned within the suturing cartridge 93141 such that the needle 93152 is configured to interrupt the magnetic field between the magnet 93162 and the Hall Effect sensor 93164. Such an interruption can indicate to a control program the position of the needle 93152 relative to the suturing cartridge 93141 and/or within its firing stroke. The sensor and magnet may be embedded within the cartridge and/or placed adjacent the needle track such as, for example, on top of, on bottom of, and/or on the sides of the needle track.

Figure 33:
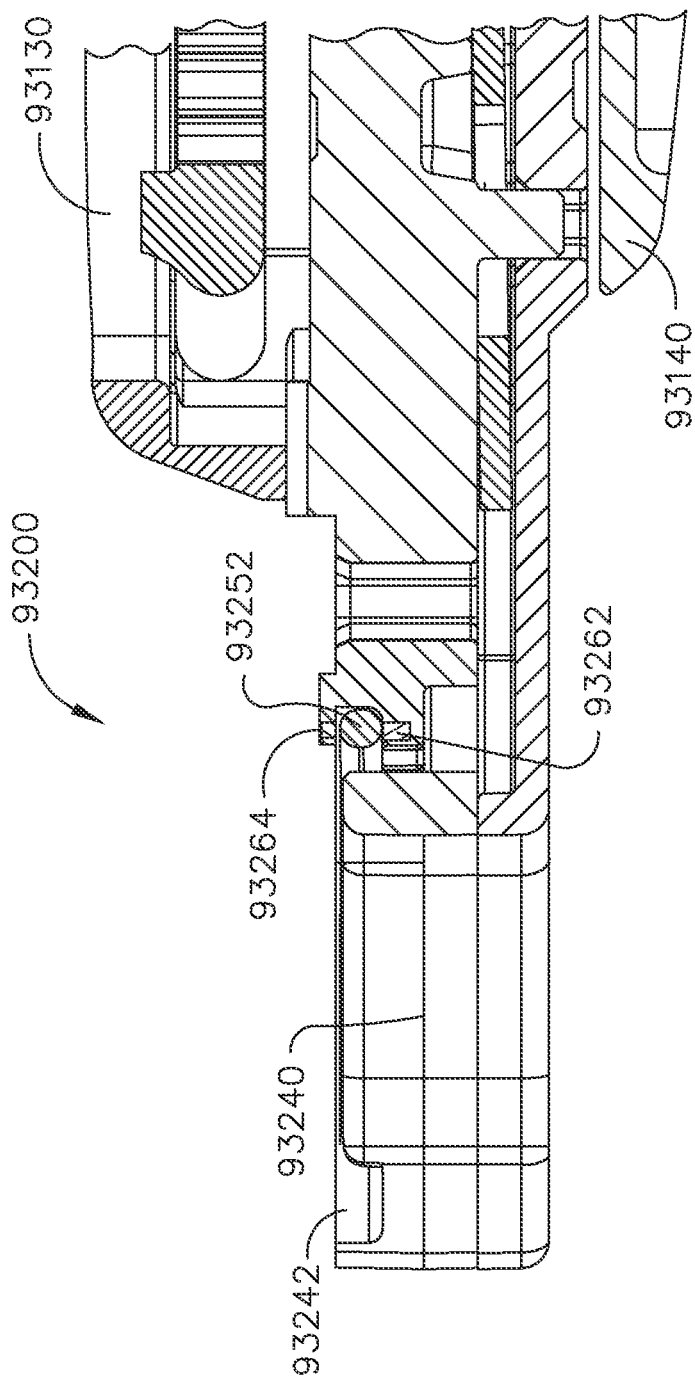
FIG. 33 is a partial cross-sectional view of an end effector assembly comprising a needle sensing system.

FIG. 33 depicts a needle sensing system 93200 positioned within a suturing cartridge 93240. The suturing cartridge 93240 comprises a needle 93252 and a needle track 93242 configured to guide the needle 93252 through a needle firing stroke. The needle sensing system 93200 comprises a magnet 93264 and a Hall Effect sensor 93262 positioned above and below, respectively, the needle track 93242. The Hall Effect sensor 93262 and the magnet 93264 are configured to indicate the position of the needle to a control circuit as the needle interrupts the magnetic field between the Hall Effect sensor 93262 and the magnet 93264. Such an arrangement can provide a more localized needle position detection system. In at least one embodiment, a suturing cartridge can contain more than one Hall Effect sensor and magnet arranged in this manner to provide multiple detection locations along the needle track. That said, any suitable sensor arrangement can be used. A control program can determine the position of the needle based on the sensor reading(s) of the Hall Effect sensor(s). A control program of the surgical instrument can adjust control motions applied to the surgical suturing instrument based on the readings from the Hall Effect sensor(s). For example, if the needle is detected to be moving slower than preferred during a firing stroke based on the time it takes for the needle to trip consecutive sensors, the control program can increase the speed of the motor driving the needle through its firing stroke. Also, for example, the control program can compensate for a lag in the position of the needle during its stroke. In at least one instance, the electrical motor of the needle firing drive can be left on for a few additional rotations to reposition the needle in its stroke.

Another system for detecting and/or monitoring the location of the suturing needle during its firing stroke can include utilizing one or more proximity sensors near the needle and/or the needle driver. As discussed above, the needle driver is configured to drive the needle out of its needle track and back into the other side of the needle track, release the needle, and return to its original position to grab the needle on the other side of the track to prepare for a second half of a firing stroke. The proximity sensor(s) can be used to monitor the location of the needle and/or the needle driver. In an instance where multiple proximity sensors are used, a first proximity sensor can be used near the entry point on the needle track and a second proximity sensor can be used near the exit point on the needle track, for example.

Figure 34:
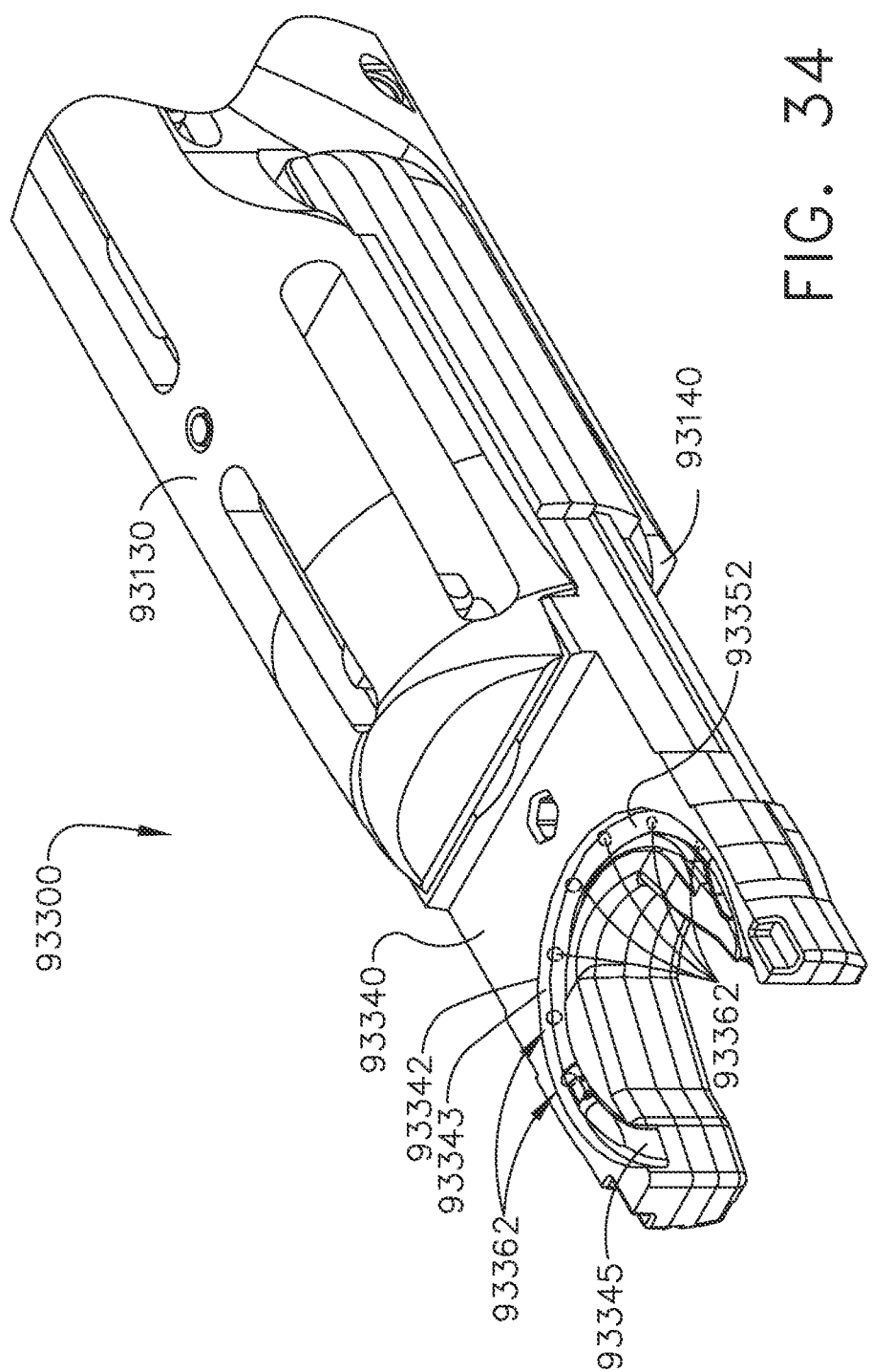
FIG. 34 is a partial perspective view of an end effector assembly comprising a needle sensing system.

FIG. 34 depicts a needle sensing system 93300 positioned within a suturing cartridge 93340. The suturing cartridge 93340 comprises a needle 93352 and a needle track 93342 configured to guide the needle 93352 through a needle firing stroke. The needle sensing system 93300 comprises a plurality of proximity sensors 93362 positioned within the needle track 93342. In at least one embodiment, the sensors 93362 are molded into a sidewall 93343 of the needle track 93342. In the same embodiment and/or another embodiment, the sensors 93362 are molded into a top, or bottom, surface 93345 of the needle track 93342. Any suitable location within the end effector assembly can be used. The sensor information can be used to determine the location of the needle 93352 which can then be used to modify the operation of the surgical instrument if appropriate.

In at least one embodiment, a plurality of proximity sensors can be used within the end effector of a suturing device to determine if a needle of the suturing device has been de-tracked or fallen out of its track. To achieve this, an array of proximity sensors can be provided such that the needle contacts at least two sensors at all times during its firing stroke. If a control program determines that only one sensor is contacted based on the data from the proximity sensors, the control system can then determine that the needle has been de-tracked and modify the operation of the drive system accordingly.

Figure 35:
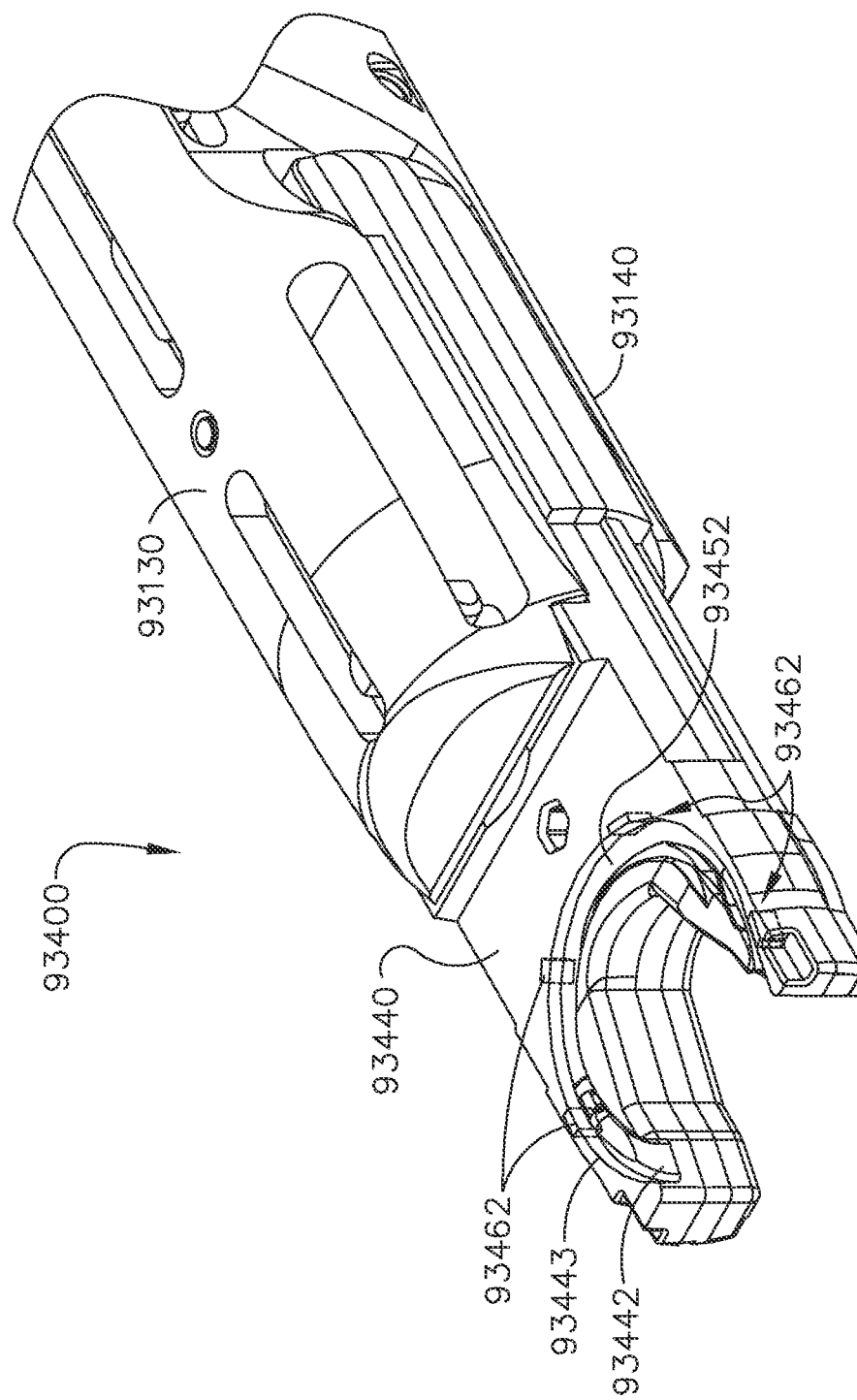
FIG. 35 is a partial perspective view of an end effector assembly comprising a needle sensing system.

FIG. 35 depicts a needle sensing system 93400 positioned within a suturing cartridge 93440. The suturing cartridge 93440 comprises a needle 93452 and a needle track 93442 configured to guide the needle 93452 through a needle firing stroke. The needle sensing system 93400 comprises a plurality of conductive sensors 93462 positioned within the needle track 93442. In one embodiment, the sensors 94362 are positioned adjacent a sidewall 93443 of the needle track 93442 such that the needle 93452 may progressively contact the sensors 94362 as the needle 93452 progresses through a needle firing stroke. In the same embodiment and/or another embodiment, the sensors 93462 are positioned adjacent a top, or bottom, surface 93445 of the needle track 93442. Any suitable location within the end effector assembly can be used. The sensor information can be used to determine the location of the needle 93452 which can then be used to modify the operation of the surgical instrument if appropriate.

Another system for detecting and/or monitoring the location of the suturing needle during its firing stroke can include placing a circuit in communication with the needle track. For example, a conductive supply leg can be wired in contact with one side of the needle track and a conductive return leg can be wired in contact with the other side of the needle track. Thus, as the needle passes by the circuit, the needle can act as a circuit switch and complete the circuit to lower the resistance within the circuit thereby providing a way to detect and/or monitor the location of the needle. Several of these circuits can be placed throughout the needle track. To aid the needle conductivity between the circuit contacts, brushes can be used to cradle the needle as the needle passes the circuit location. A flex circuit can also be used and can be adhered to inner walls of the needle track, for example. The flex circuit can contain multiple contacts, and/or terminals. In at least one instance, the contacts can be molded directly into the walls. In another instance, the contacts of the flex circuit can be folded over an inner wall of the needle track and stuck to the wall with an adhesive, for example, such that the contacts face the needle path. In yet another instance, both of these mounting options can be employed.

Another system for detecting and/or monitoring the location of the suturing needle during its firing stroke can include one or more inductive sensors. Such sensors can detect the needle and/or the needle grabber, or driver.

Another system for detecting and/or monitoring the location of the suturing needle during its firing stroke can include using a light source and a photodetector which are positioned such that movement of the needle interrupts the detection of the light source by the photodetector. A light source can be positioned within, and/or near, the needle track, for example, and faced toward the needle path. The photodetector can be positioned opposite the light source such that needle can pass between the light source and the photodetector thereby interrupting the detection of light by the photodetector as the needle passes between the light source and the photodetector. Interruption of the light provided by the light source can indicate the needle's presence or lack thereof. The light source may be an infrared LED emitter, for example. Infrared light may be preferred due to its ability to penetrate tissue and organic debris, especially within a suturing site, which otherwise could produce a false positive reading by the photodetector. That said, any suitable light emitter could be used.

Figure 36:
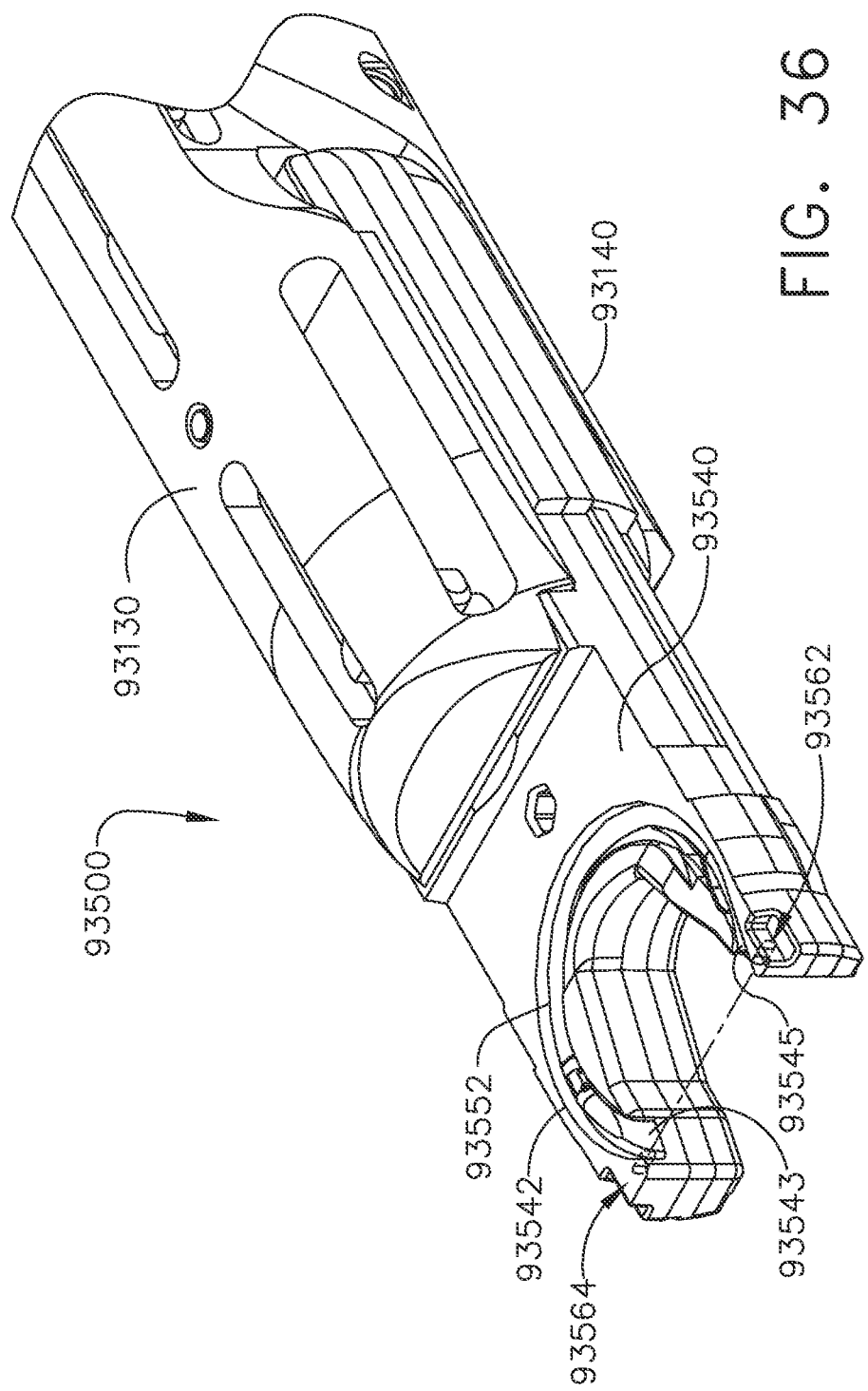
FIG. 36 is a partial perspective view of an end effector assembly comprising a needle sensing system.

FIG. 36 depicts a needle sensing system 93500 positioned within a suturing cartridge 93540. The suturing cartridge 93540 comprises a needle 93552 and a needle track 93542 configured to guide the needle 93552 through a needle firing stroke. The needle sensing system 93500 comprises a light source 93562 positioned at an entry point 93545 of the needle track 93542 and a photodetector 93564 positioned at an exit point 93543 of the needle track 93542. When the needle 93552 is in its home position as illustrated in FIG. 36, the light source 93562 is configured to emit light that spans across the capture opening of the suturing cartridge 93540 to indicate that the needle 93552 is in its home position. Once the needle 93552 interrupts the path between the light source 93562 and the photodetector 93564, a control program can determine that the needle is not in its home position. The location of the needle 93552 can be determined by a control program based on the interruption of light between the light sources and photodetectors which can then be used to modify the operation of the surgical instrument if appropriate.

Figure 37:
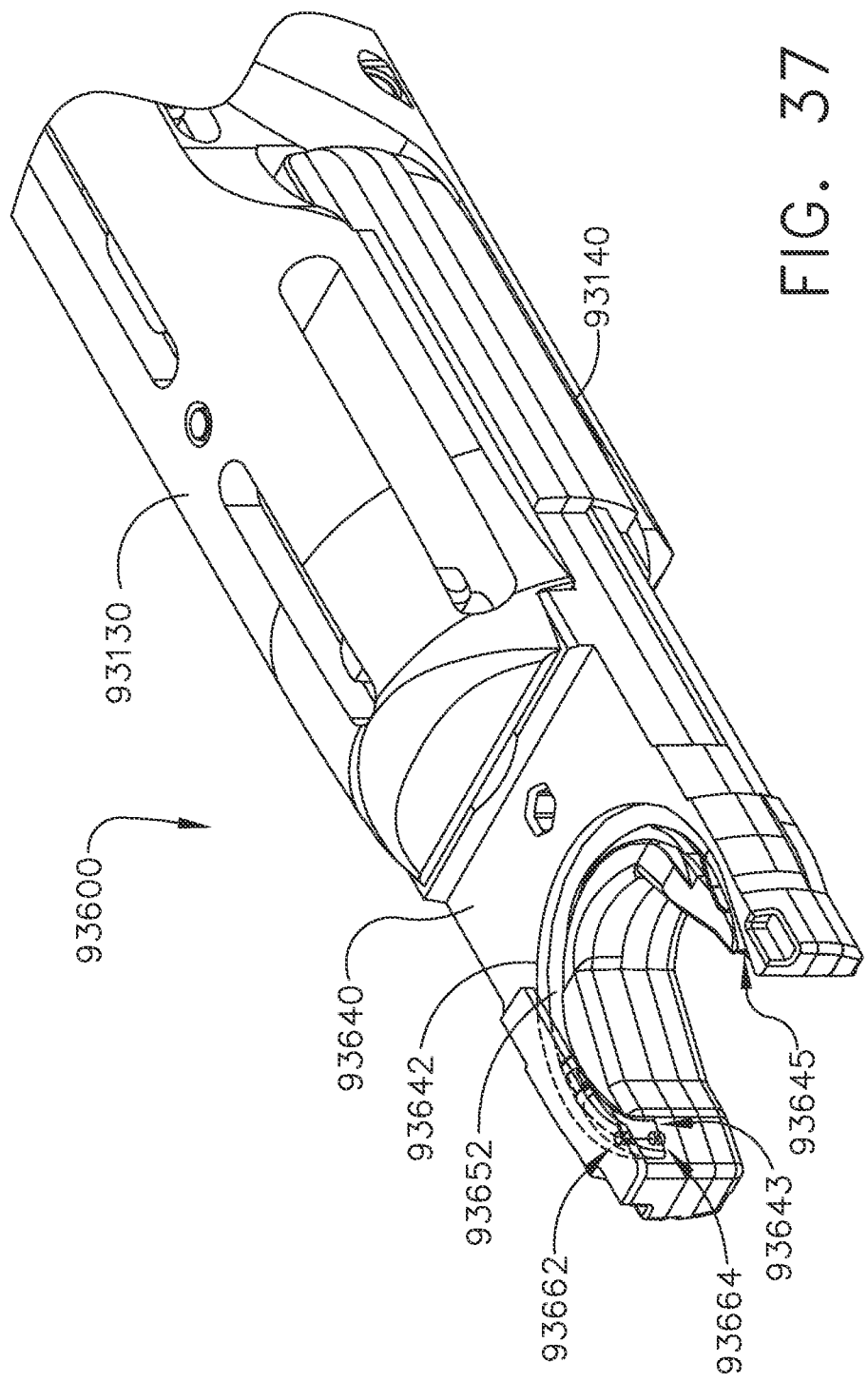
FIG. 37 is a partial perspective view of an end effector assembly comprising a needle sensing system.

FIG. 37 depicts a needle sensing system 93600 positioned within a suturing cartridge 93640. The suturing cartridge 93640 comprises a needle 93652 and a needle track 93642 configured to guide the needle 93652 through a needle firing stroke. The needle sensing system 93600 comprises a light source 93662 and a photodetector 93664 positioned at an exit point 93643 of the needle track 93642. The light source 93662 is configured to emit light that spans across the needle track cavity of the suturing cartridge 96640 to indicate the position of the needle 93652. In another embodiment, another photodetector and light source are positioned at an exit point 93645 of the needle track 93642. In yet another embodiment, an array of photodetectors and light sources are placed along the length of the needle track 93642. The location of the needle 93652 can be determined by a control program based on the interruption of light between the light source 93662 and the photodetector 93664.

In at least one embodiment, a surgical suturing needle can comprise a helical profile to provide helical suturing strokes. Such a needle comprises a length spanning 360 degrees where a butt end of the needle and a tip of the needle do not reside in the same plane and define a vertical distance therebetween. This needle can be actuated through a helical, or coil shaped, stroke to over-sew a staple line, for example, providing a three dimensional needle stroke. A needle having the helical shape discussed above provides a three dimensional suturing path.

Figure 38:
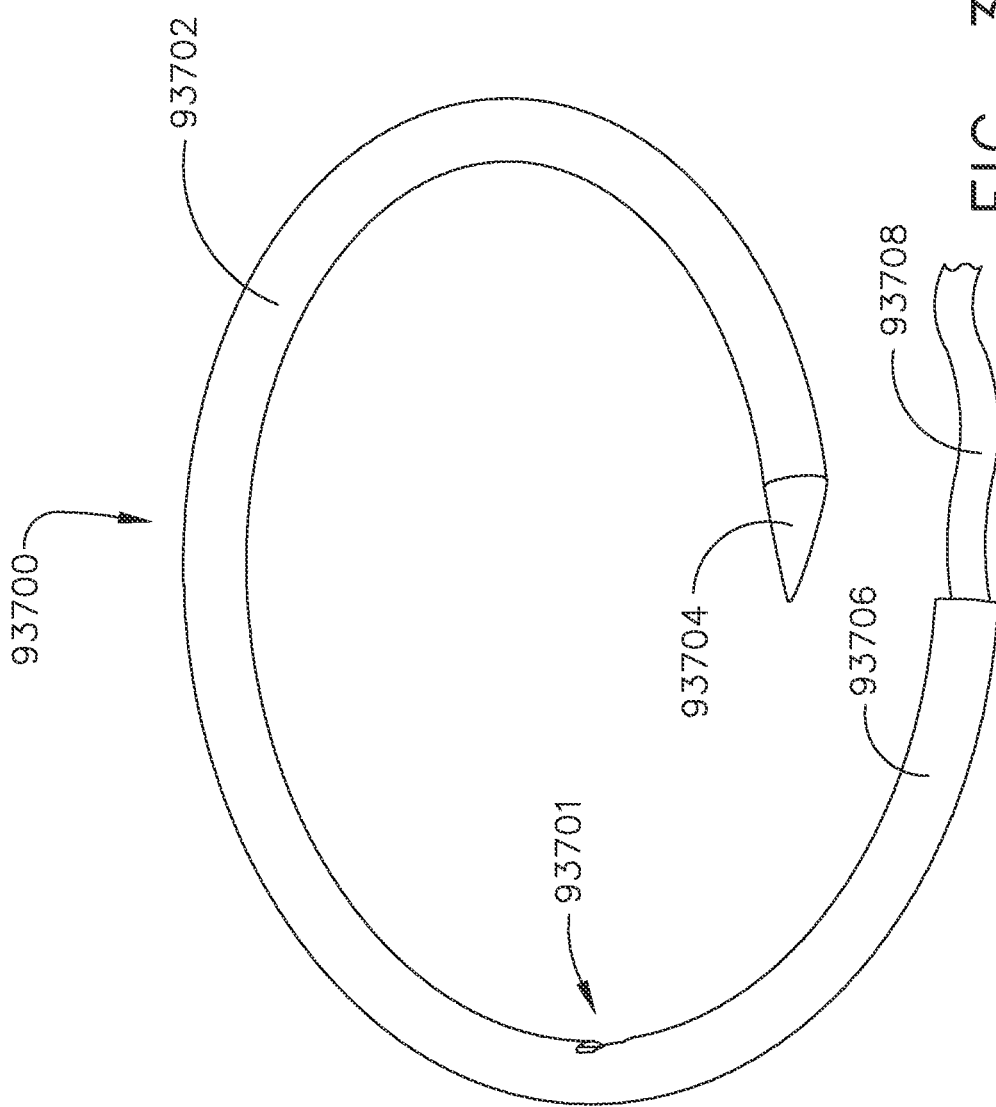
FIG. 38 is a perspective view of a helical suturing needle for use with a surgical suturing instrument.
Figure 39:
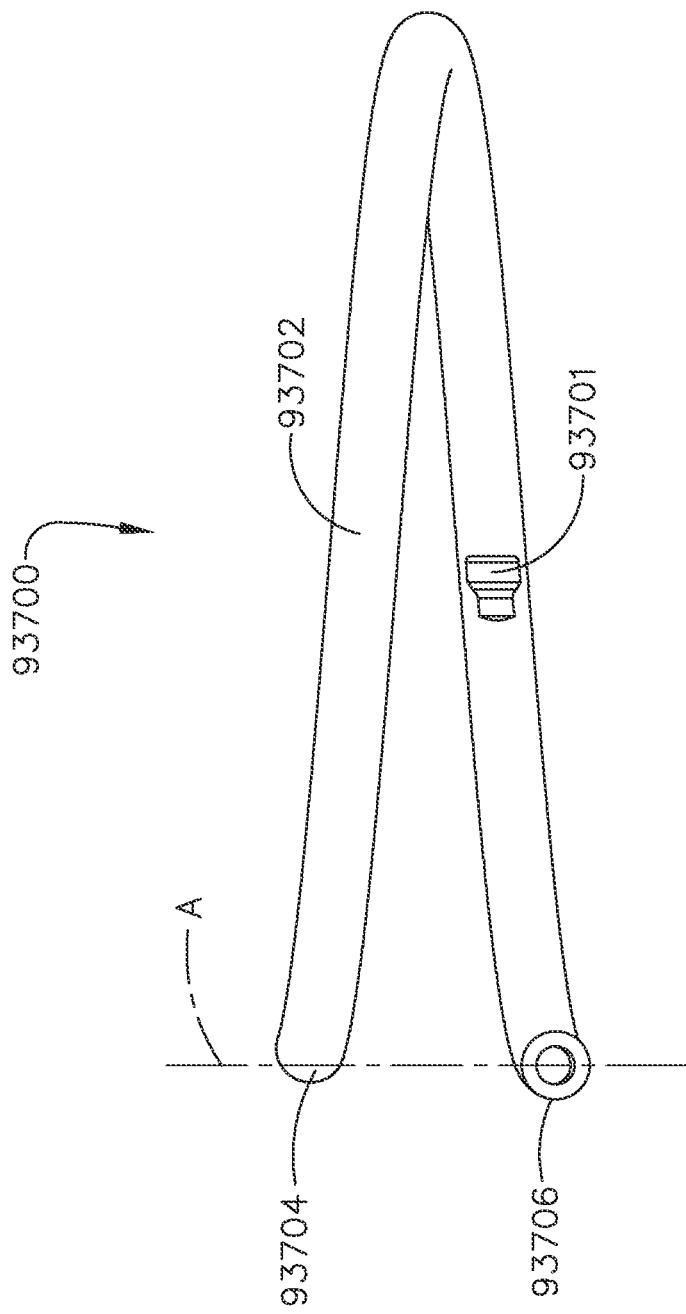
FIG. 39 is an elevational view of the helical suturing needle of FIG. 38.

FIGS. 38 and 39 depict a helical suturing needle assembly 93700 for use with a surgical suturing instrument. The suturing needle assembly 93700 comprises a tip 93704, a proximal end 93706, and a helical body portion 93702 extending therebetween. The helical body portion 93702 comprises a catch feature 93701 that a needle driver of a surgical suturing instrument is configured to catch on a return stroke of the driver. The tip 93704 and the proximal end 93706 reside in different horizontal planes and comprise a vertical distance therebetween; however, the tip 93704 and the proximal end 93706 terminate along a common axis A (FIG. 39). The needle assembly 93700 can be actuated through a helical, or coil shaped, stroke to over-sew a staple line, for example, providing a three dimensional needle stroke.

In various instances, the needle comprises a circular configuration that is less than 360 degrees in circumference. In at least one instance, the needle can be stored in the end effector in an orientation which stores the needle within the profile of the end effector. Once the end effector is positioned within the patient, the needle can be rotated out of its stored position to then perform a firing stroke.

In various embodiments, a surgical suturing instrument can accommodate different needle and suture sizes for different suturing procedures. Such an instrument can comprise a means for detecting the size of the needle and/or suture loaded into the instrument. This information can be communicated to the instrument so that the instrument can adjust the control program accordingly. Larger diameter needles may be rotated angularly at a slower rate than smaller diameter needles. Needles with different lengths may also be used with a single instrument. In such instances, a surgical instrument can comprise means for detecting the length of the needle. This information can be communicated to a surgical instrument to modify the needle driver's path, for example. A longer needle may require a smaller stroke path from the needle driver to sufficiently advance the longer needle through its firing stroke as opposed to a smaller needle which may require a longer stroke path from the needle driver to sufficiently advance the shorter needle through its firing stroke in the same needle track.

Figure 40:
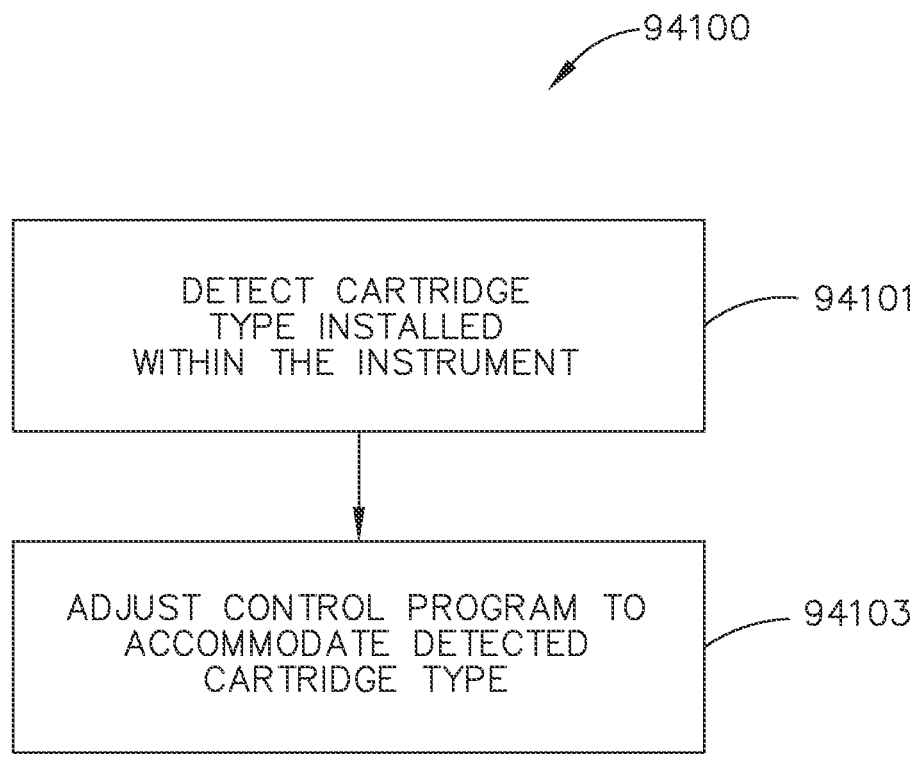
FIG. 40 is a logic flow diagram of a process depicting a control program for controlling a surgical instrument.

FIG. 40 depicts a logic diagram of a process 94100 depicting a control program for controlling a surgical instrument. The process 94100 comprises detecting 94101 the type of suturing cartridge installed within the surgical suturing instrument. In various instances, different suture cartridges may have different suture lengths, needle lengths, needle diameters, and/or suture materials, for example. The type of suture cartridge and/or its characteristics can be communicated to a control circuit by an identification chip positioned within the cartridge such that, when a suture cartridge is installed within a surgical instrument, the control circuit can identify what type of cartridge has been installed and assess the characteristics of the suture cartridge. In order to accommodate different cartridge types, a control circuit may adjust the control motions that will be applied to the suture cartridge. For example, firing speeds may differ for different sized needles. Another example may include adjusting the range of angular needle rotation based on different needle lengths, or sizes. To accommodate such differences, the process 94100 implemented by a process, for example, comprises adjusting 94103 a motor control program of the instrument based on what type of suture cartridge is installed.

In at least one embodiment, a suture needle is stored in a suturing instrument in a folded manner. In at least one such instance, the suture needle comprises two portions which are hingedly connected to one another at a hinge. After the end effector has been passed through the trocar, the suture needle can be unfolded and locked into its unfolded configuration. In at least one instance, a one-way snap feature can be used to rigidly hold the suture needle in its unfolded configuration.

In at least one embodiment, a surgical instrument is configured to apply a suture to the tissue of a patient which comprises a lockout system. The lockout system comprises a locked configuration and an unlocked configuration. The surgical instrument further comprises a control circuit and is configured to identify if a cartridge is installed or not installed within an end effector of the surgical instrument. The control circuit is configured to place the lockout system in the locked condition when a cartridge is not installed in the end effector and place the lockout system in the unlocked condition when a cartridge is installed in the end effector. Such a lockout system can include an electrical sensing circuit of which a cartridge can complete upon installation indicating that a cartridge has been installed. In at least one instance, the actuator comprises an electric motor and the lockout system can prevent power from being supplied to the electric motor. In at least one instance, the actuator comprises a mechanical trigger, and the lockout system blocks the mechanical trigger from being pulled to actuate the suture needle. When the lockout system is in the locked configuration, the lockout system prevents an actuator from being actuated. When the lockout system is in the unlocked configuration, the lockout system permits the actuator to deploy the suture positioned within the cartridge. In one embodiment, the control circuit provides haptic feedback to a user of the surgical instrument when the electrical sensing circuit places the surgical instrument in the locked configuration. In one embodiment, the control circuit prevents the actuation of an electric motor configured to actuate the actuator when the electrical sensing circuit determines that the lockout system is in the locked configuration. In one embodiment, the lockout system is in the unlocked configuration when a cartridge is positioned in the end effector and the cartridge has not been completely expended.

Figure 41:
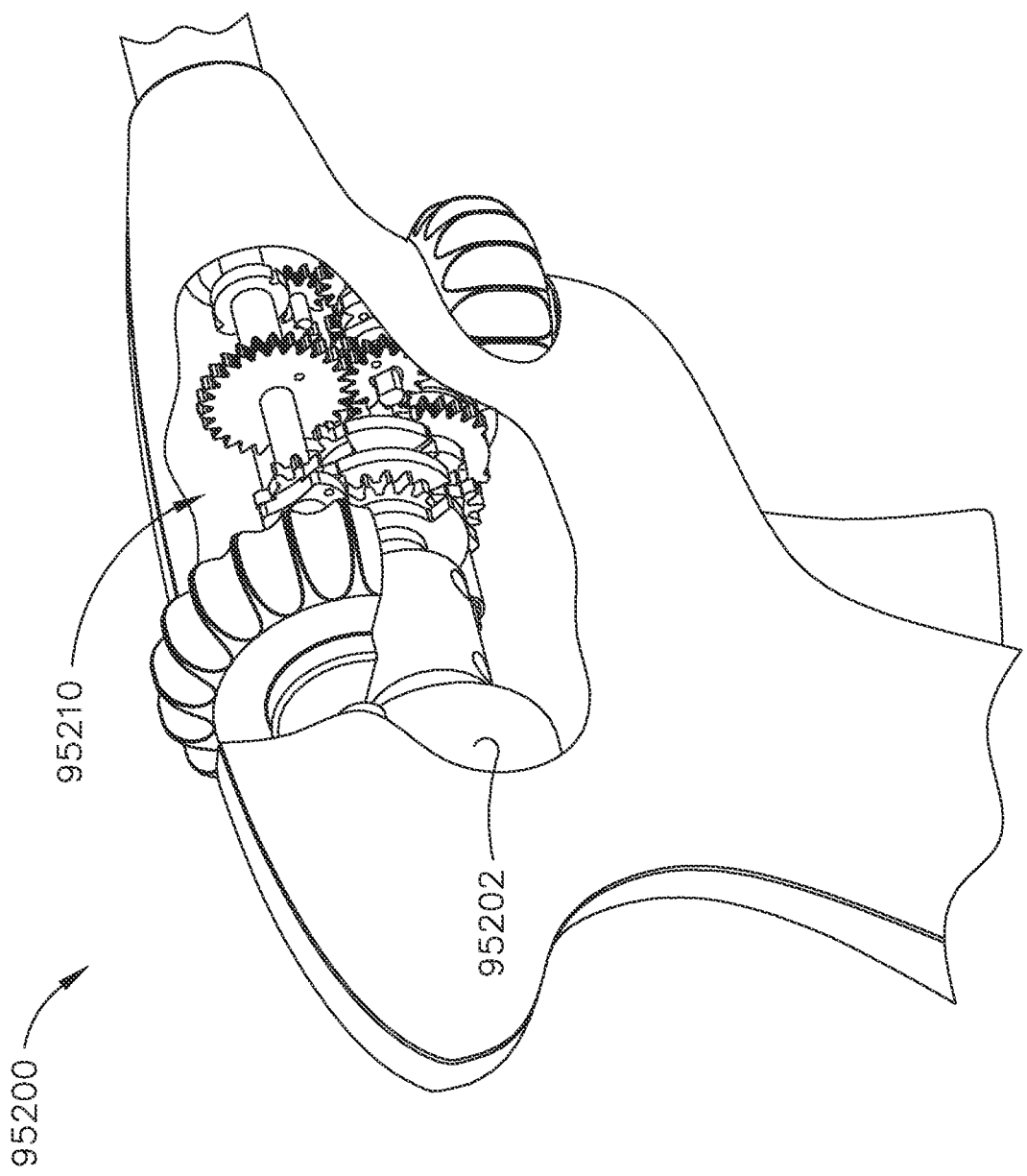
FIG. 41 is a perspective view of a surgical suturing instrument handle comprising a motor.
Figure 42:
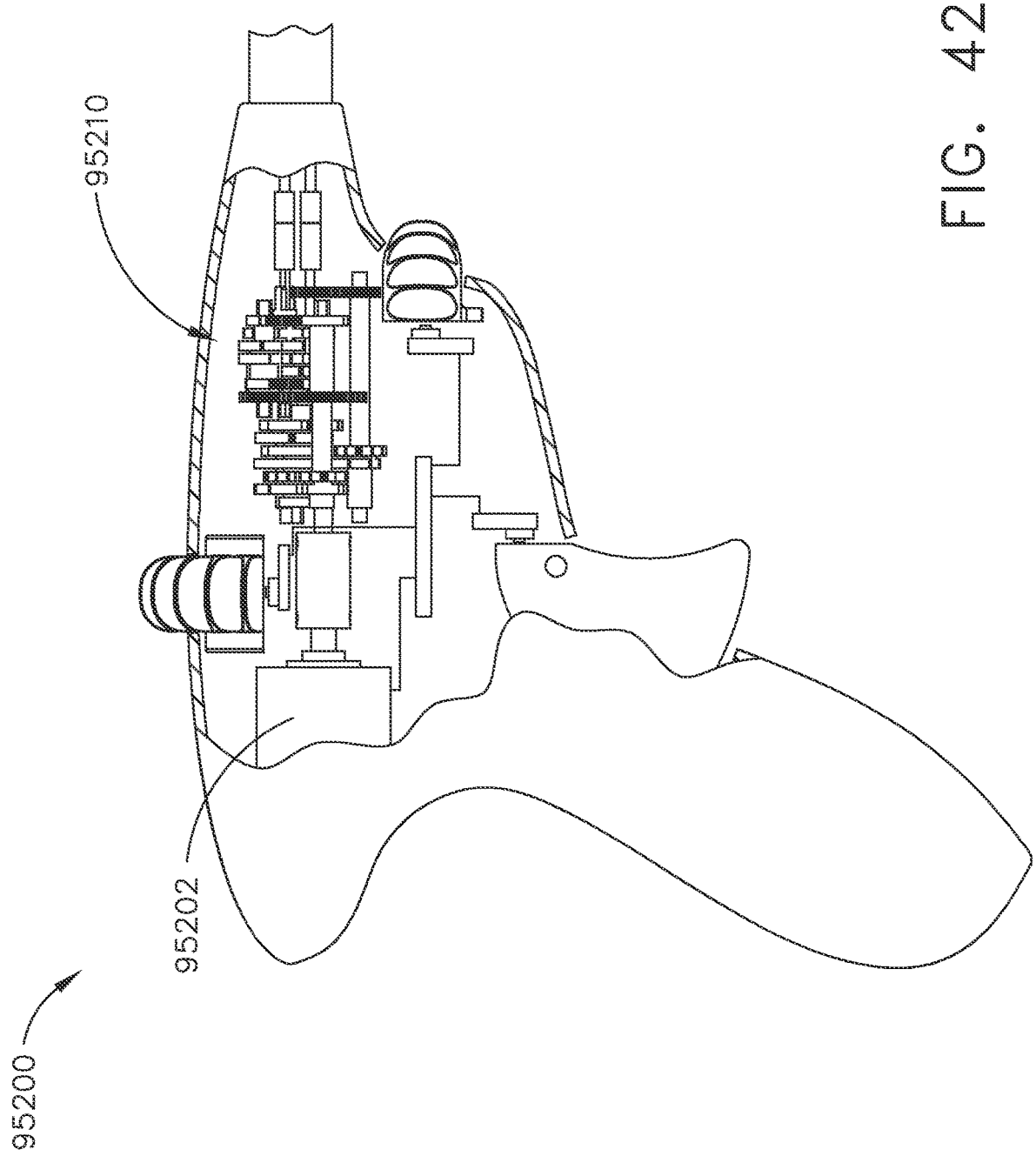
FIG. 42 is a partial cross-sectional view of the surgical suturing instrument handle of FIG. 41.

FIGS. 41 and 42 depict a handle assembly 95200 that is operable for use a surgical suturing instrument. The handle assembly 95200 is connected to a proximal end of a shaft. The handle assembly 95200 includes a motor 95202 and a transmission assembly 95210. The motor 95202 is configured to actuate a needle of a surgical suturing end effector by way of a needle driver, articulate the end effector, and rotate the end effector by way of the transmission assembly 95210. The transmission assembly 95210 is shifted between three states by a double acting solenoid, for example, so as to allow the motor 95202 to be used to actuate a needle of a surgical suturing end effector, articulate the end effector, and/or rotate the end effector. In at least one embodiment, the handle assembly 95200 could take the form of a robotic interface or a housing comprising gears, pulleys, and/or servomechanisms, for example. Such an arrangement could be used with a robotic surgical system.

Figure 43:
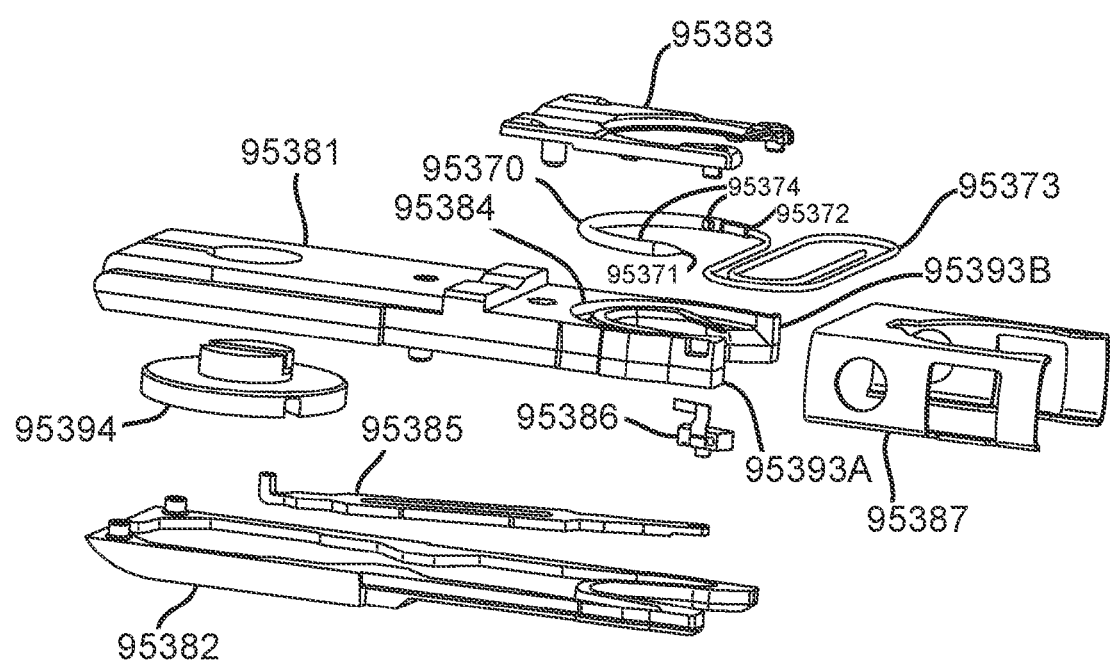
FIG. 43 is an exploded view of a suturing cartridge for use with a surgical suturing system.

FIG. 43 depicts a suturing cartridge 93590 comprising a lower body 93581, an upper body 93582, and a needle cover 93583. The cartridge 93590 further comprises a drive system comprising a needle driver 93586, a rotary input 93594, and a link 93585 connecting the needle driver 93586 and the rotary input 93594. The needle driver 93586, rotary input 93594, and link 93585 are captured between the lower body 93581 and the upper body 93582. The needle driver 93586, the link 93585, and the rotary input 93594 are configured to be actuated to drive a needle 93570 through a needle firing stroke by way of a motor-driven system, a manually-driven handheld system, and/or a robotic system, for example. The lower and upper bodies 93581, 93582 are attached to one another using any suitable technique, such as, for example, welds, pins, adhesives, and/or the like to form the cartridge body. The needle 93570 comprises a leading end 93571 configured to puncture tissue, a trailing end 93572, and a length of suture 93573 extending from and attached to the trailing end 93572. The needle 93570 is configured to rotate in a circular path defined by a needle track 93584. The needle track 93584 is defined in the cartridge body. The needle 93570 is configured to exit one of a first arm 95393A and a second arm 95393B of the cartridge body and enter the other of the first arm 95393A and the second arm 95393B during a needle firing stroke. Recessed features 93574 are provided to so that the needle driver 93586 can engage and drive the needle 93570 through the needle firing stroke in a ratchet-like motion. The needle 93570 is positioned between the needle track 93584 and the needle cover 93583. The suturing cartridge 93590 further comprises a cage 93587 that is configured to slide over the cartridge body to attach the needle cover 93583 to the lower body 93581.

Figure 44:
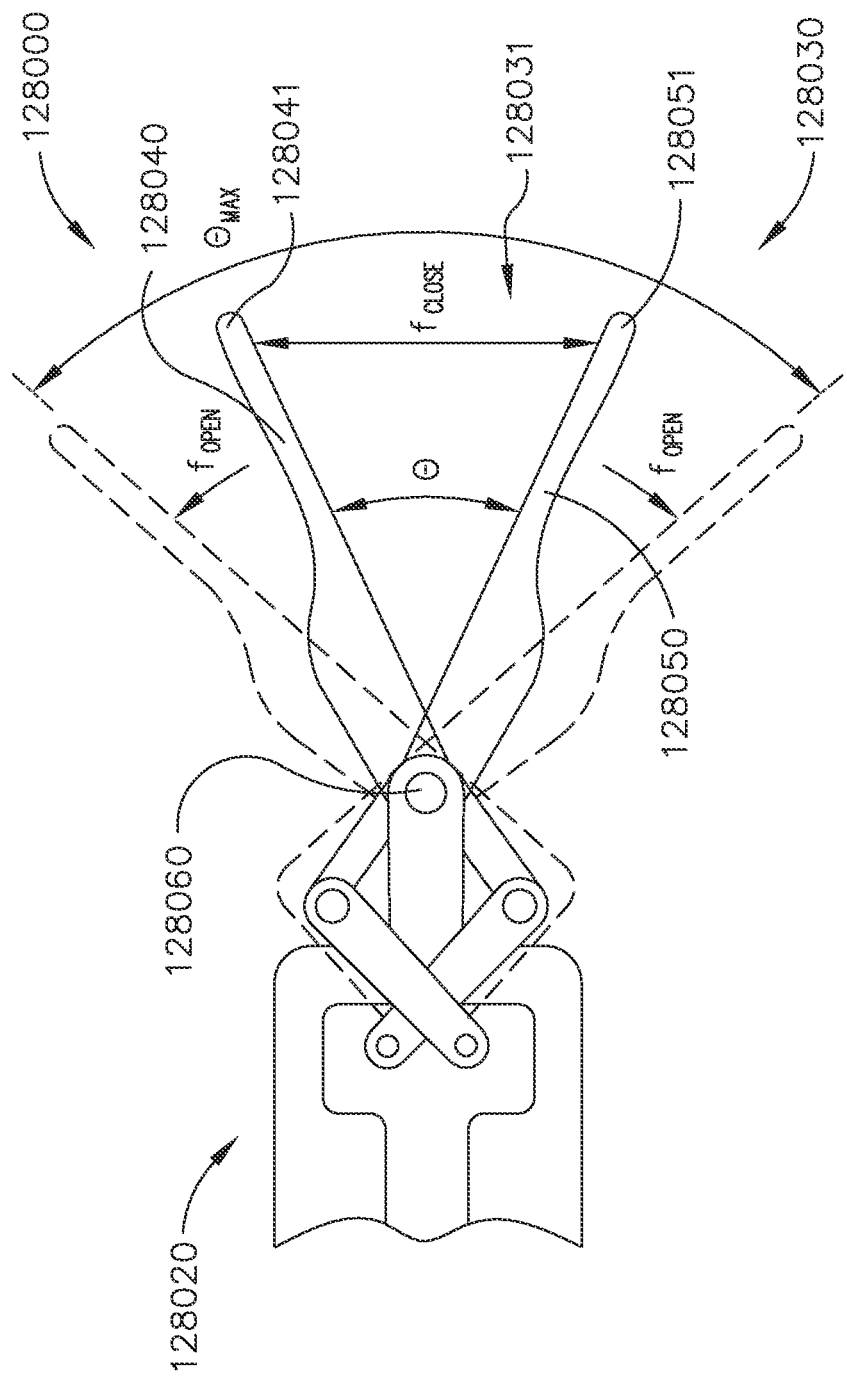
FIG. 44 is a partial cross-sectional view of a surgical instrument including a jaw assembly capable of grasping and dissection in accordance with at least one embodiment.

A surgical system 128000 is illustrated in FIG. 44. The surgical system 128000 comprises a handle, a shaft 128020 extending from the handle, and an end effector 128030 extending from the shaft 128020. In alternative embodiments, the surgical system 128000 comprises a housing configured to be mounted to a robotic surgical system. In at least one such embodiment, the shaft 128020 extends from the robotic housing mount instead of the handle. In either event, the end effector 128030 comprises jaws 128040 and 128050 which are closeable to grasp a target, such as the tissue T of a patient and/or a suture needle, for example, as discussed in greater detail below. The jaws 128040 and 128050 are also openable to dissect the tissue of a patient, for example. In at least one instance, the jaws 128040 and 128050 are insertable into the patient tissue to create an otomy therein and then spread to open the otomy, as discussed in greater detail below.

Referring again to FIG. 44, the jaws 128040 and 128050 are pivotably coupled to the shaft 128020 about a pivot joint 128060. The pivot joint 128060 defines a fixed axis of rotation, although any suitable arrangement could be used. The jaw 128040 comprises a distal end, or tip, 128041 and an elongate profile which narrows from its proximal end to its distal end 128041. Similarly, the jaw 128050 comprises a distal end, or tip, 128051 and an elongate profile which narrows from its proximal end to its distal end 128051. The distance between the tips 128041 and 128051 define the mouth width, or opening, 128032 of the end effector 128030. When the tips 128041 and 128051 are close to one another, or in contact with one another, the mouth 128032 is small, or closed, and the mouth angle θ is small, or zero. When the tips 128041 and 128051 are far apart, the mouth 128032 is large and the mouth angle θ is large.

Further to the above, the jaws of the end effector 128030 are driven by a jaw drive system including an electric motor. In use, a voltage potential is applied to the electric motor to rotate the drive shaft of the electric motor and drive the jaw drive system. The surgical system 128000 comprises a motor control system configured to apply the voltage potential to the electric motor. In at least one instance, the motor control system is configured to apply a constant DC voltage potential to the electric motor. In such instances, the electric motor will run at a constant speed, or an at least substantially constant speed. In various instances, the motor control system comprises a pulse width modulation (PWM) circuit and/or a frequency modulation (FM) circuit which can apply voltage pulses to the electric motor. The PWM and/or FM circuits can control the speed of the electric motor by controlling the frequency of the voltage pulses supplied to the electric motor, the duration of the voltage pulses supplied to the electric motor, and/or the duration between the voltage pulses supplied to the electric motor.

The motor control system is also configured to monitor the current drawn by the electric motor as a means for monitoring the force being applied by the jaws of the end effector 128030. When the current being drawn by the electric motor is low, the loading force on the jaws is low. Correspondingly, the loading force on the jaws is high when the current being drawn by the electric motor is high. In various instances, the voltage being applied to the electric motor is fixed, or held constant, and the motor current is permitted to fluctuate as a function of the force loading at the jaws. In certain instances, the motor control system is configured to limit the current drawn by the electric motor to limit the force that can be applied by the jaws. In at least one embodiment, the motor control system can include a current regulation circuit that holds constant, or at least substantially constant, the current drawn by the electric motor to maintain a constant loading force at the jaws.

The force generated between the jaws of the end effector 128030, and/or on the jaws of the end effector 128030, may be different depending on the task that the jaws are being used to perform. For instance, the force needed to hold a suture needle may be high as suture needles are typically small and it is possible that a suture needle may slip during use. As such, the jaws of the end effector 128030 are often used to generate large forces when the jaws are close together. On the other hand, the jaws of the end effector 128030 are often used to apply smaller forces when the jaws are positioned further apart to perform larger, or gross, tissue manipulation, for example.

Figure 45:
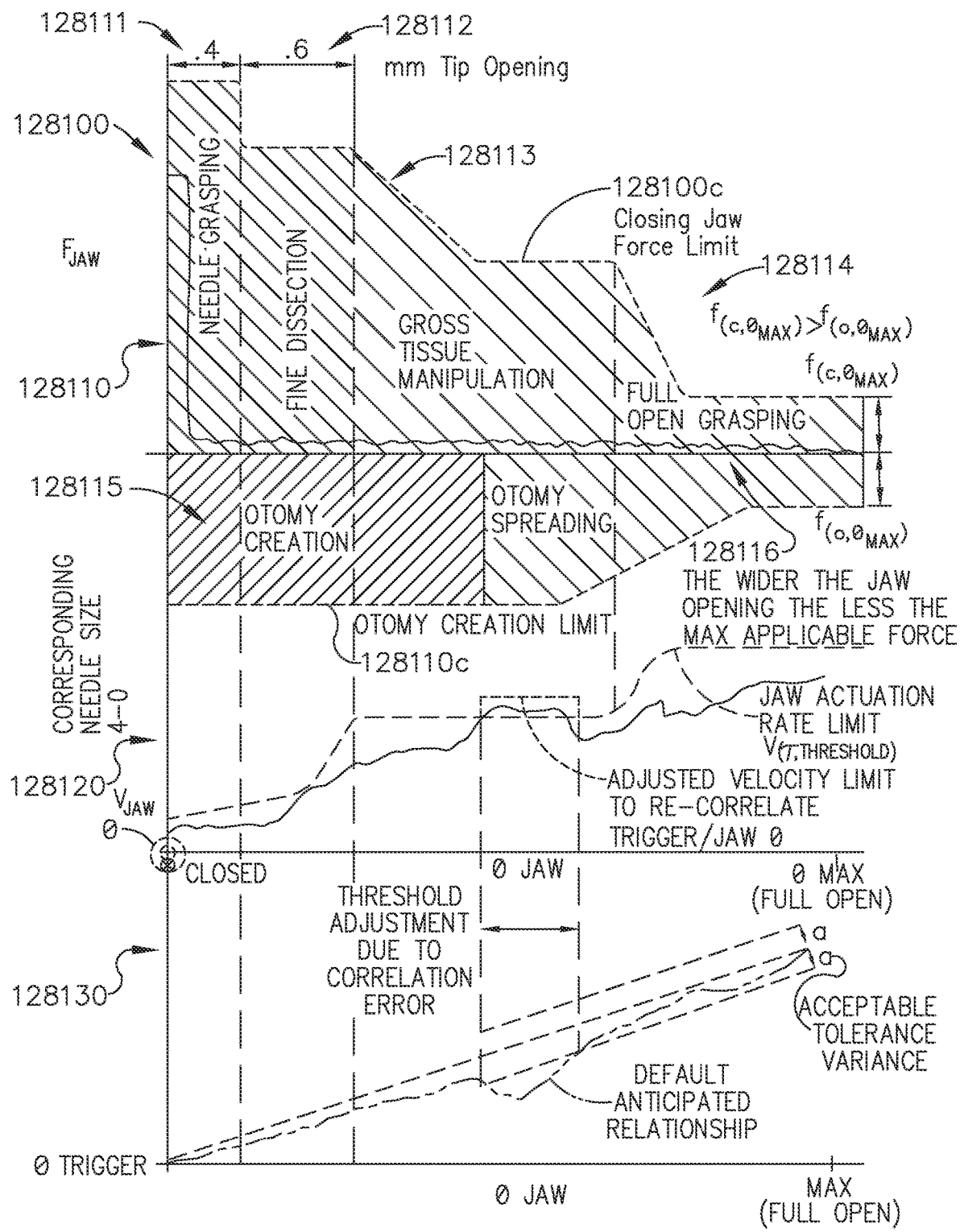
FIG. 45 is a graph depicting the force, speed, and orientation of the jaw assembly of FIG. 44 in accordance with at least one embodiment.

Referring to the upper portion 128110 of the graph 128100 illustrated in FIG. 45, the loading force, f, experienced by the jaws of the end effector 128030 can be limited by a force profile stored in the motor control system. The force limit profile 128110o for opening the jaws 128040 and 128050 is different than the force limit profile 128110c for closing the jaws 128040 and 128050. This is because the procedures performed when forcing the jaws 128040 and 128050 open are typically different than the procedures performed when forcing the jaws 128040 and 128050 closed. That said, the opening and closing force limit profiles could be the same. While it is likely that the jaws 128040 and 128050 will experience some force loading regardless of whether the jaws 128050 are being opened or closed, the force limit profiles typically come into play when the jaws 128040 and 128050 are being used to perform a particular procedure within the patient. For instance, the jaws 128040 and 128050 are forced open to create and expand an otomy in the tissue of a patient, as represented by graph sections 128115 and 128116, respectively, of graph 128100, while the jaws 128040 and 128050 are forced closed to grasp a needle and/or the patient tissue, as represented by graph sections 128111 and 128112, respectively, of graph 128100.

Referring again to FIG. 45, the opening and closing jaw force limit profiles 128110o and 128110c, respectively, are depicted on the opposite sides of a zero force line depicted in the graph 128100. As can be seen in the upper section 128110 of graph 128100, the jaw force limit threshold is higher—for both force limit profiles 128110o and 128110c—when the jaws 128040 and 128050 are just being opened from their fully-closed position. As can also be seen in the upper section 128110 of graph 128100, the jaw force limit threshold is lower—for both force limit profiles 128110o and 128110c—when the jaws 128040 and 128050 are reaching their fully-opened position. Such an arrangement can reduce the possibility of the jaws 128040 and 128050 damaging adjacent tissue when the being fully opened, for example. In any event, the force that the jaws 128040 and 128050 are allowed to apply is a function of the mouth opening size between the jaws and/or the direction in which the jaws are being moved. For instance, when the jaws 128040 and 128050 are opened widely, or at their maximum, to grasp large objects, referring to graph section 128114 of upper graph section 128110, the jaw force f limit is very low as compared to when the jaws 128040 and 128050 are more closed to perform gross tissue manipulation, referring to graph section 128113 of upper graph section 128110. Moreover, different jaw force limit profiles can be used for different jaw configurations. For instance, Maryland dissectors, which have narrow and pointy jaws, may have a different jaw force limit profile than a grasper having blunt jaws, for example.

In addition to or in lieu of the above, the speed of the jaws 128040 and 128050 can be controlled and/or limited by the motor control system as a function of the mouth opening size between the jaws 128040 and 128050 and/or the direction the jaws are being moved. Referring to the middle portion 128120 and lower portion 128130 of the graph 128100 in FIG. 45, the rate limit profile for moving the jaws 128040 and 128050 permits the jaws to be moved slowly when the jaws are near their closed position and moved quickly when the jaws are near their open position. In such instances, the jaws 128040 and 128050 are accelerated as the jaws are opened. Such an arrangement can provide fine control over the jaws 128040 and 128050 when they are close together to facilitate the fine dissection of tissue, for example. Notably, the rate limit profile for opening and closing the jaws 128040 and 128050 is the same, but they could be different in other embodiments. In alternative embodiments, the rate limit profile for moving the jaws 128040 and 128050 permits the jaws to be moved quickly when the jaws are near their closed position and slowly when the jaws are near their open position. In such instances, the jaws 128040 and 128050 are decelerated as the jaws are opened. Such an arrangement can provide fine control over the jaws 128040 and 128050 when the jaws are being used to stretch an otomy, for example. The above being said, the speed of the jaws 128040 and 128050 can be adjusted once the jaws experience loading resistance from the patient tissue, for example. In at least one such instance, the jaw opening rate and/or the jaw closing rate can be reduced once the jaws 128040 and 128050 begin to experience force resistance above a threshold, for example.

In various instances, further to the above, the handle of the surgical system 128000 comprises an actuator, the motion of which tracks, or is supposed to track, the motion of the jaws 128040 and 128050 of the end effector 128030. For instance, the actuator can comprise a scissors-grip configuration which is openable and closable to mimic the opening and closing of the end effector jaws 128040 and 128050. The control system of the surgical system 128000 can comprise one or more sensor systems configured to monitor the state of the end effector jaws 128040 and 128050 and the state of the handle actuator and, if there is a discrepancy between the two states, the control system can take a corrective action once the discrepancy exceeds a threshold and/or threshold range. In at least one instance, the control system can provide feedback, such as audio, tactile, and/or haptic feedback, for example, to the clinician that the discrepancy exists and/or provide the degree of discrepancy to the clinician. In such instances, the clinician can make mental compensations for this discrepancy. In addition to or in lieu of the above, the control system can adapt its control program of the jaws 128040 and 128050 to match the motion of the actuator. In at least one instance, the control system can monitor the loading force being applied to the jaws and align the closed position of the actuator with the position of the jaws when the jaws experience the peak force loading condition when grasping tissue. Similarly, the control system can align the open position of the actuator with the position of the jaws when the jaws experience the minimum force loading condition when grasping tissue. In various instances, the control system is configured to provide the clinician with a control to override these adjustments and allow the clinician to use their own discretion in using the surgical system 128000 in an appropriate manner.

A surgical system 128700 is illustrated in FIGS. 46 and 47. The surgical system 128700 comprises a handle, a shaft assembly 128720 extending from the handle, and an end effector 128730 extending from the shaft assembly 128720. In alternative embodiments, the surgical system 128700 comprises a housing configured to be mounted to a robotic surgical system. In at least one such embodiment, the shaft 128720 extends from the robotic housing mount instead of the handle. In either event, the end effector 128730 comprises shears configured to transect the tissue of a patient. The shears comprise two jaws 128740 and 128750 configured to transect the patient tissue positioned between the jaws 128740 and 128750 as the jaws 128740 and 128750 are being closed. Each of the jaws 128740 and 128750 comprises a sharp edge configured to cut the tissue and are pivotably mounted to the shaft 128720 about a pivot joint 128760. Such an arrangement can comprise bypassing scissors shears. Other embodiments are envisioned in which one of the jaws 128740 and 128750 comprises a knife edge and the other comprises a mandrel against the tissue is supported and transected. Such an arrangement can comprise a knife wedge in which the knife wedge is moved toward the mandrel. In at least one embodiment, the jaw comprising the knife edge is movable and the jaw comprising the mandrel is stationary. The above being said, embodiments are envisioned in which the tissue-engaging edges of one or both of the jaws 128740 and 128750 are not necessarily sharp.

Figure 48:
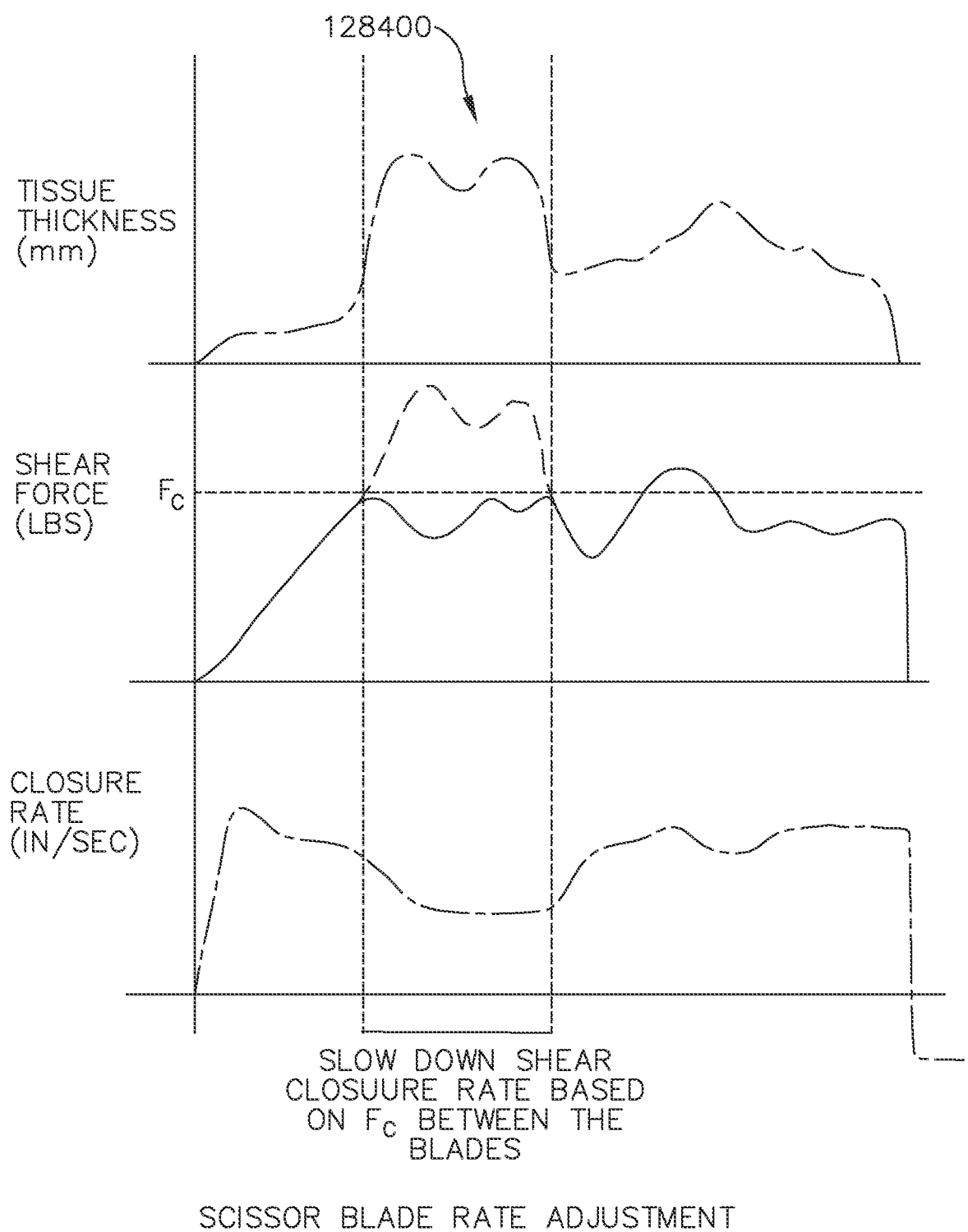
FIG. 48 is a graph depicting the force and speed of the jaws of the bipolar forceps of FIG. 46 in accordance with at least one embodiment.

As discussed above, the end effector 128730 comprises two scissor jaws 128740 and 128750 movable between an open position and a closed position to cut the tissue of a patient. The jaw 128740 comprises a sharp distal end 128741 and the jaw 128750 comprises a sharp distal end 128751 which are configured to snip the tissue of the patient at the mouth 128731 of the end effector 128730, for example. That said, other embodiments are envisioned in which the distal ends 128741 and 128751 are blunt and can be used to dissect tissue, for example. In any event, the jaws are driven by a jaw drive system including an electric drive motor, the speed of which is adjustable to adjust the closure rate and/or opening rate of the jaws. Referring to the graph 128400 of FIG. 48, the control system of the surgical system is configured to monitor the loading, or shear, force on the jaws 128740 and 128750 as the jaws 128740 and 128750 are being closed and adaptively slow down the drive motor when large forces, or forces above a threshold Fc, are experienced by the jaws 128740 and 128750. Such large forces often occur when the tissue T being cut by the jaws 128740 and 128750 is thick, for example. Similar to the above, the control system can monitor the current drawn by the drive motor as a proxy for the loading force being experienced by the jaws 128740 and 128750. In addition to or in lieu of this approach, the control system can be configured to measure the jaw loading force directly by one or more load cells and/or strain gauges, for example. Once the loading force experienced by the jaws 128740 and 128750 drops below the force threshold Fc, the control system can adaptively speed up the jaw closure rate. Alternatively, the control system can maintain the lower closure rate of the jaws 128740 and 128750 even though the force threshold is no longer being exceeded.

The above-provided discussion with respect to the surgical system 128700 can provide mechanical energy or a mechanical cutting force to the tissue of a patient. That said, the surgical system 128700 is also configured to provide electrosurgical energy or an electrosurgical cutting force to the tissue of a patient. In various instances, the electrosurgical energy comprises RF energy, for example; however, electrosurgical energy could be supplied to the patient tissue at any suitable frequency. In addition to or in lieu of AC power, the surgical system 128700 can be configured to supply DC power to the patient tissue. The surgical system 128700 comprises a generator in electrical communication with one or more electrical pathways defined in the instrument shaft 128720 which can supply electrical power to the jaws 128740 and 128750 and also provide a return path for the current. In at least one instance, the jaw 128740 comprises an electrode 128742 in electrical communication with a first electrical pathway in the shaft 128720 and the jaw 128750 comprises an electrode 128752 in electrical communication with a second electrical pathway in the shaft 128720. The first and second electrical pathways are electrically insulated, or at least substantially insulated, from one another and the surrounding shaft structure such that the first and second electrical pathways, the electrodes 128742 and 128752, and the tissue positioned between the electrodes 128742 and 128752 forms a circuit. Such an arrangement provides a bipolar arrangement between the electrodes 128742 and 128752. That said, embodiments are envisioned in which a monopolar arrangement could be used. In such an arrangement, the return path for the current goes through the patient and into a return electrode positioned on or under the patient, for example.

As discussed above, the tissue of a patient can be cut by using a mechanical force and/or an electrical force. Such mechanical and electrical forces can be applied simultaneously and/or sequentially. For instance, both forces can be applied at the beginning of a tissue cutting actuation and then the mechanical force can be discontinued in favor of the electrosurgical force finishing the tissue cutting actuation. Such an approach can apply an energy-created hemostatic seal to the tissue after the mechanical cutting has been completed. In such arrangements, the electrosurgical force is applied throughout the duration of the tissue cutting actuation. In other instances, the mechanical cutting force, without the electrosurgical cutting force, can be used to start a tissue cutting actuation which is then followed by the electrosurgical cutting force after the mechanical cutting force has been stopped. In such arrangements, the mechanical and electrosurgical forces are not overlapping or co-extensive. In various instances, both the mechanical and electrosurgical forces are overlapping and co-extensive throughout the entire tissue cutting actuation. In at least one instance, both forces are overlapping and co-extensive throughout the entire tissue cutting actuation but in magnitudes or intensities that change during the tissue cutting actuation. The above being said, any suitable combination, pattern, and/or sequence of mechanical and electrosurgical cutting forces and energies could be used.

Figure 49:
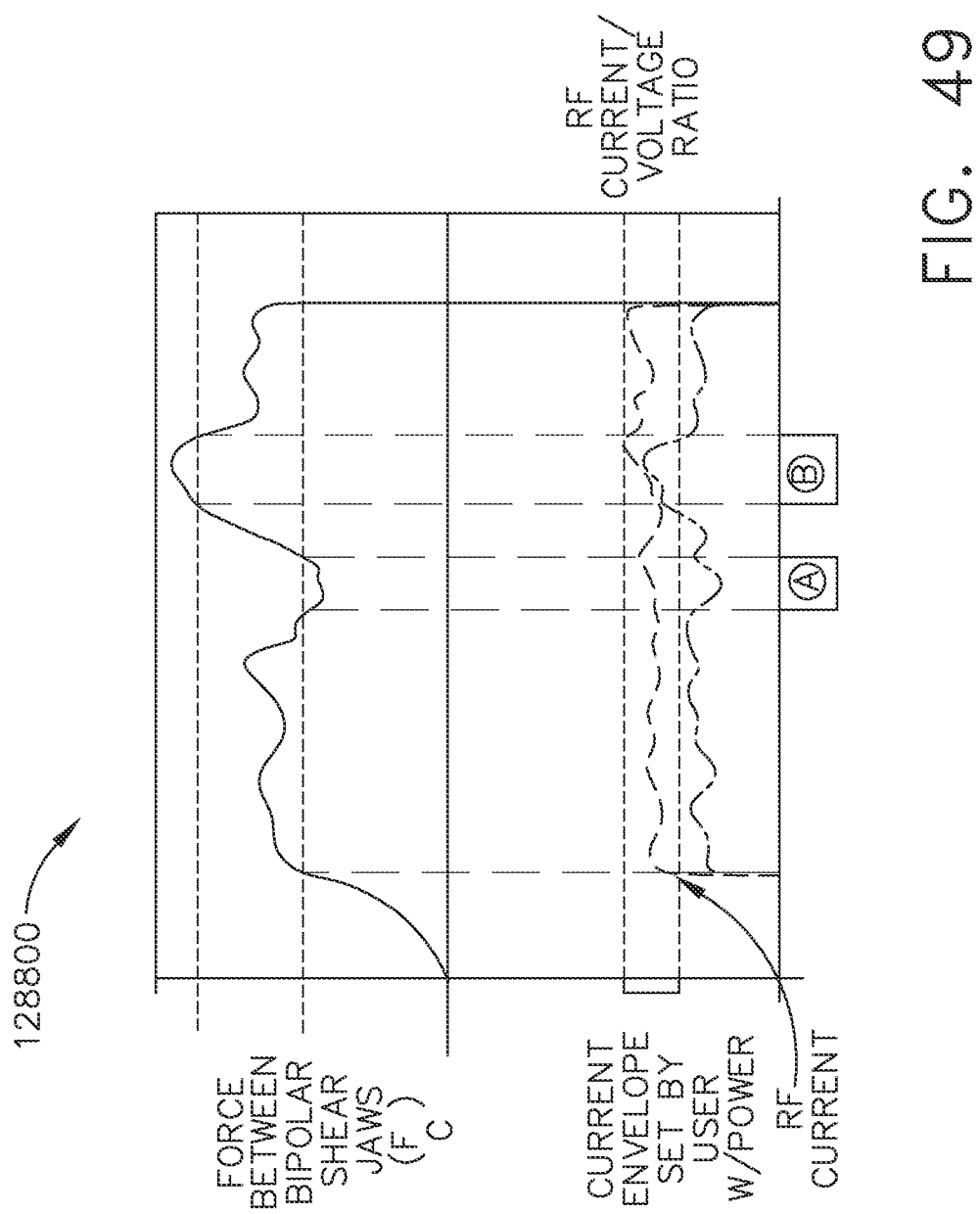
FIG. 49 is another graph depicting the operation of the bipolar forceps of FIG. 46 in accordance with at least one embodiment.

Further to the above, the surgical system 128700 comprises a control system configured to co-ordinate the application of the mechanical force and electrosurgical energy to the patient tissue. In various instances, the control system is in communication with the motor controller which drives the jaws 128740 and 128750 and, also, the electrical generator and comprises one or more sensing systems for monitoring the mechanical force and electrosurgical energy being applied to the tissue. Systems for monitoring the forces within a mechanical drive system are disclosed elsewhere herein. Systems for monitoring the electrosurgical energy being applied to the patient tissue include monitoring the impedance, or changes in the impedance, of the patient tissue via the electrical pathways of the electrosurgical circuit. In at least one instance, referring to the graph 128800 in FIG. 49, the RF current/voltage ratio of the electrosurgical power being applied to the patient tissue by the generator is evaluated by monitoring the current and voltage of the power being supplied by the generator. The impedance of the tissue and the RF current/voltage ratio of the electrosurgical power are a function of many variables such as the temperature of the tissue, the density of the tissue, the thickness of the tissue, the type of tissue between the jaws 128740 and 128750, the duration in which the power is applied to the tissue, among others, which change throughout the application of the electrosurgical energy.

Further to the above, the control system and/or generator of the surgical system 128700 comprises one or more ammeter circuits and/or voltmeter circuits configured to monitor the electrosurgical current and/or voltage, respectively, being applied to the patient tissue. Referring again to FIG. 49, a minimum amplitude limit and/or a maximum amplitude limit on the current being applied to the patient tissue can be preset in the control system and/or can be controllable by the user of the surgical instrument system through one or more input controls. The minimum and maximum amplitude limits can define a current envelope within which the electrosurgical portion of the surgical system 128700 is operated.

In various instances, the control system of the surgical system 128700 is configured to adaptively increase the electrosurgical energy applied to the patient tissue when the drive motor slows. The motor slowing can be a reaction to an increase in the tissue cutting load and/or an adaptation of the control system. Similarly, the control system of the surgical system 128700 is configured to adaptively increase the electrosurgical energy applied to the patient tissue when the drive motor stops. Again, the motor stopping can be a reaction to an increase in the tissue cutting load and/or an adaptation of the control system. Increasing the electrosurgical energy when the electric motor slows and/or stops can compensate for a reduction in mechanical cutting energy. In alternative embodiments, the electrosurgical energy can be reduced and/or stopped when the electric motor slows and/or stops. Such embodiments can afford the clinician to evaluate the situation in a low-energy environment.

In various instances, the control system of the surgical system 128700 is configured to adaptively decrease the electrosurgical energy applied to the patient tissue when the drive motor speeds up. The motor speeding up can be a reaction to a decrease in the cutting load and/or an adaptation of the control system. Decreasing the electrosurgical energy when the electric motor slows and/or stops can compensate for, or balance out, an increase in mechanical cutting energy. In alternative embodiments, the electrosurgical energy can be increased when the electric motor speeds up. Such embodiments can accelerate the closure of the jaws and provide a clean, quick cutting motion.

In various instances, the control system of the surgical system 128700 is configured to adaptively increase the speed of the drive motor when the electrosurgical energy applied to the patient tissue decreases. The electrosurgical energy decreasing can be a reaction to a change in tissue properties and/or an adaptation of the control system. Similarly, the control system of the surgical system 128700 is configured to adaptively increase the speed of the drive motor when electrosurgical energy applied to the patient tissue stops in response to an adaptation of the control system. Increasing the speed of the drive motor when the electrosurgical energy decreases or is stopped can compensate for a reduction in electrosurgical cutting energy. In alternative embodiments, the speed of the drive motor can be reduced and/or stopped when the electrosurgical energy decreases and/or is stopped. Such embodiments can afford the clinician to evaluate the situation in a low-energy and/or static environment.

In various instances, the control system of the surgical system 128700 is configured to adaptively decrease the speed of the electric motor when the electrosurgical energy applied to the patient tissue increases. The electrosurgical energy increasing can be a reaction to a change in tissue properties and/or an adaptation of the control system. Decreasing the drive motor speed when the electrosurgical energy increases can compensate for, or balance out, an increase in electrosurgical cutting energy. In alternative embodiments, the drive motor speed can be increased when the electrosurgical energy increases. Such embodiments can accelerate the closure of the jaws and provide a clean, quick cutting motion.

In various instances, the surgical system 128700 comprises controls, such as on the handle of the surgical system 128700, for example, that a clinician can use to control when the mechanical and/or electrosurgical forces are applied. In addition to or in lieu of manual controls, the control system of the surgical system 128700 is configured to monitor the mechanical force and electrical energy being applied to the tissue and adjust one or the other, if needed, to cut the tissue in a desirable manner according to one or more predetermined force-energy curves and/or matrices. In at least one instance, the control system can increase the electrical energy being delivered to the tissue once the mechanical force being applied reaches a threshold limit. Moreover, the control system is configured to consider other parameters, such as the impedance of the tissue being cut, when making adjustments to the mechanical force and/or electrical energy being applied to the tissue.

Figure 50:
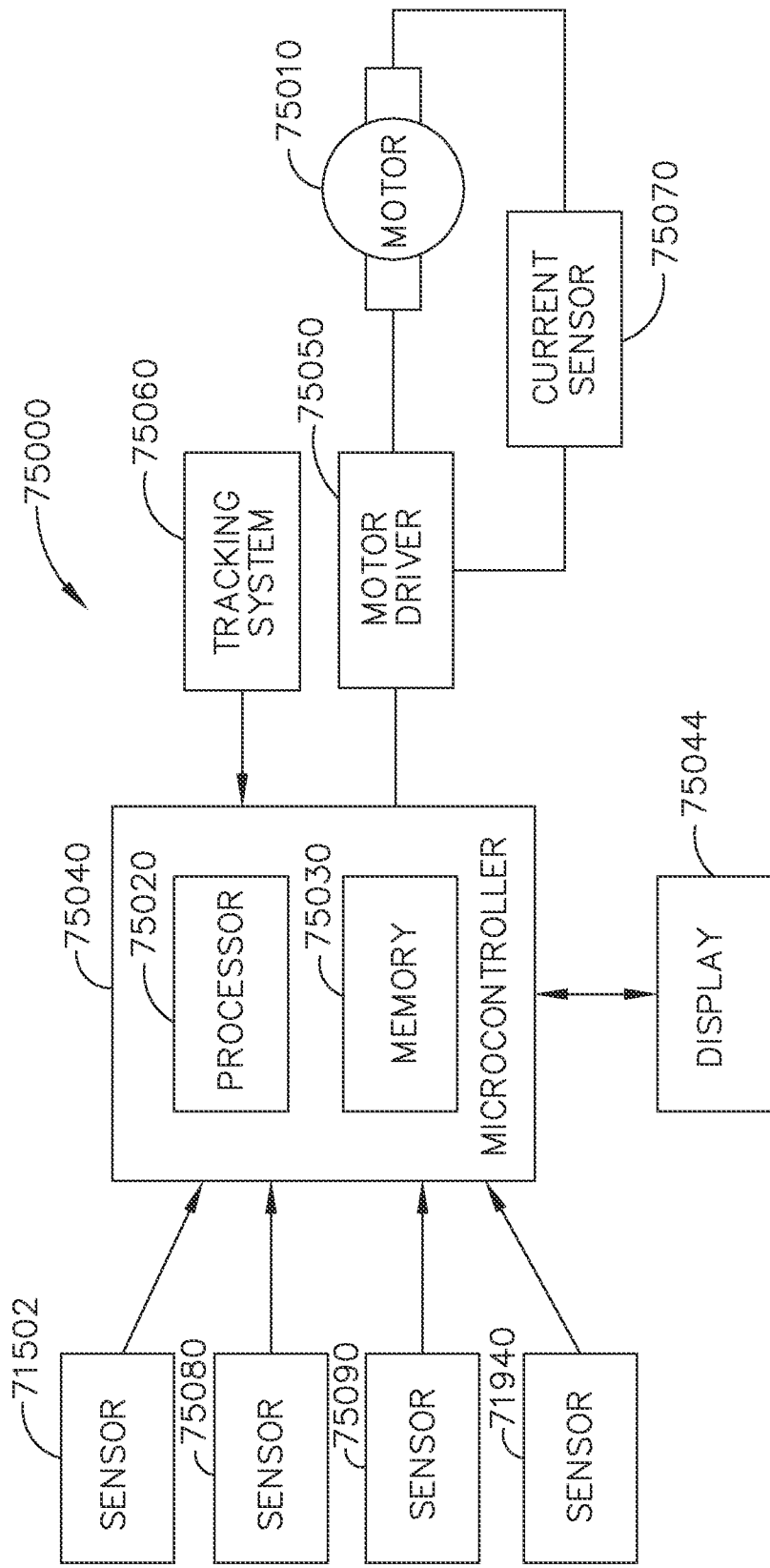
FIG. 50 is a schematic of a control system for use with any of the surgical instruments disclosed herein.
Figure 51:
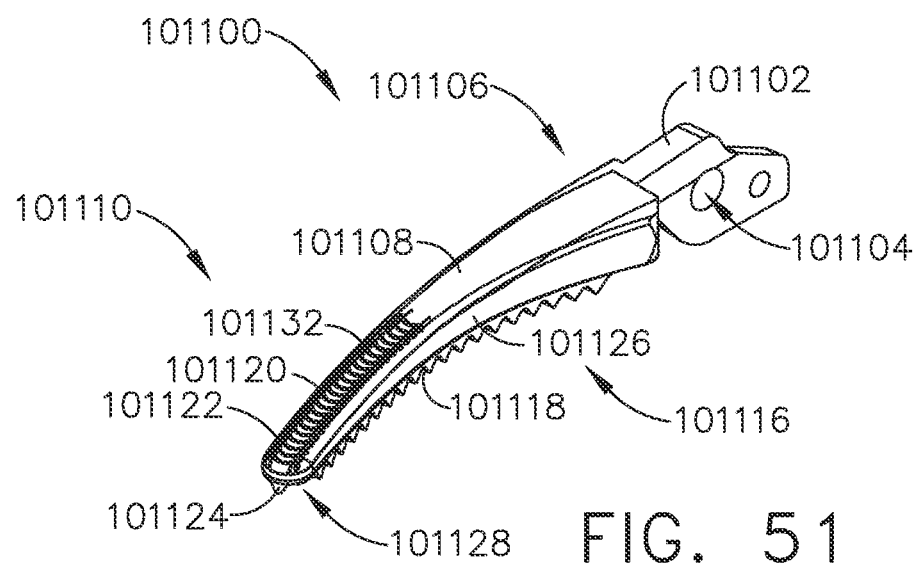
FIG. 51 is a top perspective view of a jaw of a surgical instrument.
Figure 53:
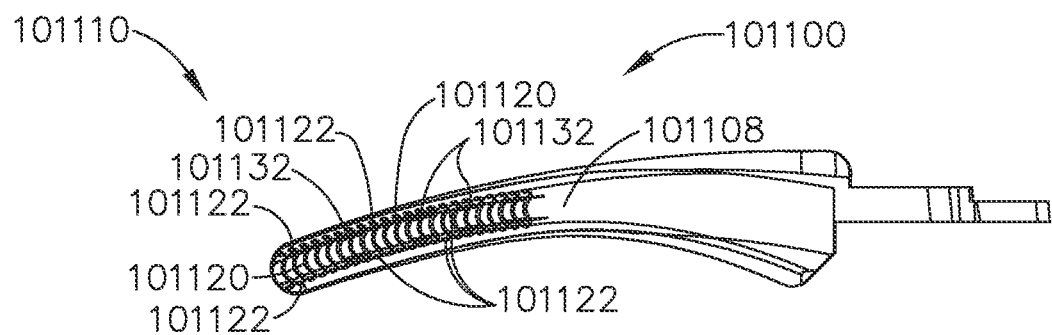
FIG. 53 is a top plan view of the jaw depicted in FIG. 51.
Figure 54:
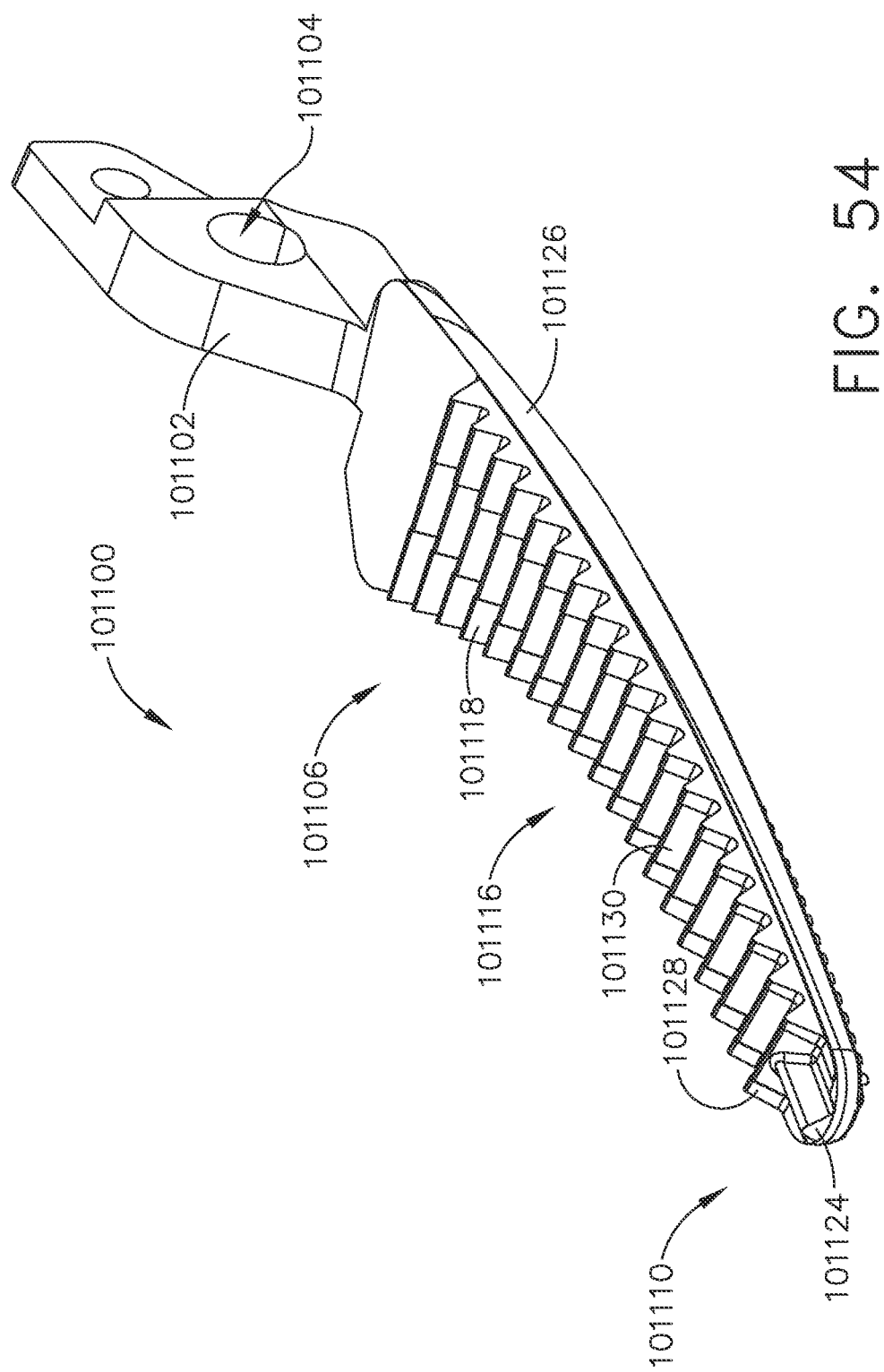
FIG. 54 is a bottom perspective view of the jaw depicted in FIG. 51.

FIG. 50 is a logic diagram of a control system 75000 for use with any of the various suturing instruments described herein. The control system 75000 comprises a control circuit. The control circuit includes a microcontroller 75040 comprising a processor 75020 and a memory 75030. One or more sensors, such as sensor 75080, sensor 75090, sensor 71502, and sensor array 71940, for example, provide real time feedback to the processor 75020. The control system 75000 further comprises a motor driver 75050 configured to control an electric motor 75010 and a tracking system 75060 configured to determine the position of one or more movable components in the suturing instruments, such as a needle, needle drive system, suture, and/or suture spool, for example. The tracking system 75060 provides position information to the processor 75020, which can be programmed or configured to, among other things, determine the position of the suture needle, for example. The motor driver 75050 may be an A3941 available from Allegro Microsystems, Inc., for example; however, other motor drivers may be readily substituted for use in the tracking system 75060. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 75040 may be any single core or multicore processor such as those known under the trade name ARM Cortex by Texas Instruments, for example. In at least one instance, the microcontroller 75040 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 75040 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 75040 is programmed to perform various functions such as precisely controlling the speed and/or position of the suture needle, for example. The microcontroller 75040 is also programmed to precisely control the rotational speed and position of the end effector of the suturing instrument and the articulation speed and position of the end effector of the suturing instrument. In various instances, the microcontroller 75040 computes a response in the software of the microcontroller 75040. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 75010 is controlled by the motor driver 75050. In various forms, the motor 75010 is a DC brushed driving motor having a maximum rotational speed of approximately 25,000 RPM, for example. In other arrangements, the motor 75010 includes a brushless motor, a cordless motor, a synchronous motor, a stepper motor, or any other suitable electric motor. The motor driver 75050 may comprise an H-bridge driver comprising field-effect transistors (FETs), for example. The motor driver 75050 may be an A3941 available from Allegro Microsystems, Inc., for example. The A3941 motor driver 75050 is a full-bridge controller for use with external N-channel power metal oxide semiconductor field effect transistors (MOSFETs) specifically designed for inductive loads, such as brush DC motors. In various instances, the motor driver 75050 comprises a unique charge pump regulator provides full (>10 V) gate drive for battery voltages down to 7 V and allows the A3941 motor driver 75050 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 75060 comprises a controlled motor drive circuit arrangement comprising one or more position sensors, such as the sensor 75080, sensor 75090, sensor 71502, and sensory array 71940, for example. The position sensors for an absolute positioning system provide a unique position signal corresponding to the location of a displacement member. As used herein, the term displacement member is used generically to refer to any movable member of any of the surgical instruments disclosed herein. In various instances, the displacement member may be coupled to any position sensor suitable for measuring linear displacement or rotational displacement. Linear displacement sensors may include contact or non-contact displacement sensors. The displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 75080, 75090, 71502, and 71940 for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 75060 comprise a magnetic rotary absolute positioning system. Such position sensors may be implemented as an AS5055EQFT single-chip magnetic rotary position sensor available from Austria Microsystems, AG and can be interfaced with the controller 75040 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 75040. The position sensors can provide 12 or 14 bits of resolution, for example. The position sensors can be an AS5055 chip provided in a small QFN 16-pin 4×4×0.85 mm package, for example.

The tracking system 75060 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 75010 has taken to infer the position of a device actuator, the needle driver, and the like.

A sensor 75080 and/or 71502 comprising a strain gauge or a micro-strain gauge, for example, is configured to measure one or more parameters of the end effector of the suturing instrument, such as, for example, the strain experienced by the needle during a suturing operation. The measured strain is converted to a digital signal and provided to the processor 75020. A sensor 75090 comprising a load sensor, for example, can measure another force applied by the suturing instrument. In various instances, a current sensor 75070 can be employed to measure the current drawn by the motor 75010. The force required to throw, or rotate, the suturing needle can correspond to the current drawn by the motor 75010, for example. The measured force is converted to a digital signal and provided to the processor 75020. A magnetic field sensor can be employed to measure the thickness of the captured tissue. The measurement of the magnetic field sensor can also be converted to a digital signal and provided to the processor 75020.

The measurements of the tissue thickness and/or the force required to rotate the needle through tissue as measured by the sensors can be used by the controller 75040 to characterize the position and/or speed of the movable member being tracked. In at least one instance, the memory 75030 may store a technique, an equation, and/or a look-up table which can be employed by the controller 75040 in the assessment. In various instances, the controller 75040 can provide the user of the suturing instrument with a choice as to the manner in which the suturing instrument should be operated. To this end, a display 75044 can display a variety of operating conditions of the suturing instrument and can include touch screen functionality for data input. Moreover, information displayed on the display 75044 may be overlaid with images acquired via the imaging modules of one or more endoscopes and/or one or more additional surgical instruments used during the surgical procedure.

As discussed above, the suturing instruments disclosed herein may comprise control systems. Each of the control systems can comprise a circuit board having one or more processors and/or memory devices. Among other things, the control systems are configured to store sensor data, for example. They are also configured to store data which identifies the type of suturing instrument attached to a handle or housing. More specifically, the type of suturing instrument can be identified when attached to the handle or housing by the sensors and the sensor data can be stored in the control system. Moreover, they are also configured to store data including whether or not the suturing instrument has been previously used and/or how many times the suture needle has been cycled. This information can be obtained by the control system to assess whether or not the suturing instrument is suitable for use and/or has been used less than a predetermined number of times, for example.

FIGS. 51-58 illustrate surgical instruments that comprise the mechanical features of surgical dissectors and the electrosurgical features of electrosurgical devices. The combination of surgical dissector and electrosurgical instrument can allow the surgical instruments illustrated in FIGS. 51-58 to perform various surgical procedures. In addition, the combination of the mechanical and electrosurgical features may allow a surgeon to perform a surgical procedure without having to switch between different surgical instruments. As discussed in greater detail below, the combination of a mechanical dissector and an electrosurgical instrument can provide synergistic effects and improve the overall efficiencies and abilities of surgical end effectors.

The embodiments disclosed in FIGS. 51-58 illustrate various end effector jaws comprising mechanical dissector features and electrosurgical device features. These end effector jaws can be used with surgical instruments to deliver mechanical as well as electrical energy to a patient's tissue. The surgical instruments can comprise proximal and distal end effector portions. The proximal portion may include a user interface, such as a handle portion and/or a connector that can connect the surgical instrument to a robotic system, for example. The distal portion of the surgical instruments can comprise a surgical end effector. The surgical end effector can comprise a pair of jaws that are rotatable between open and closed positions. The embodiments disclosed in FIGS. 51-58 illustrate an end effector jaw that can be used in a pair of jaws of a surgical end effector.

FIGS. 51-54 illustrate a surgical end effector jaw 101100 comprising a frame 101102, a metallic core 101130, and a covering 101126. The end effector jaw 101100 comprises an inner surface 101118 and an outer surface 101108. When the end effector jaw 101100 is used in a pair of jaws of a surgical instrument, the inner surfaces 101118 of the end effector jaws 101100 are positioned adjacent one another. The outer surfaces, 101108 of the end effector jaw 101100 are positioned on opposite sides of the end effector jaw 101100.

The frame 101102 of the surgical end effector jaw 101100 comprises a socket 101104. When the end effector jaw 101100 is used in a pair of jaws of a surgical instrument, the sockets 101104 of the two end effector jaws 101100 are aligned and a pin can be inserted through the sockets 101104. The pair of end effector jaws 101100 can be rotated about the pin between open and closed positions. The surgical instrument can also comprise an actuator that can move the end effector jaws 101100 between open and closed positions.

The surgical end effector jaw 101100 comprises a proximal portion 101106 and a distal portion 101110. The overall geometry of the end effector jaw 101100 is curved between the proximal portion 101106 and the distal portion 101110. In addition, the end effector jaw 101100 is tapered from the wider proximal portion 101106 to the narrower distal portion 101110. The tapered profile of the end effector jaw 101100 can permit a surgeon to target a specific location within a patient.

In addition, or in the alternative, the surgical end effector jaw 101100 can comprise other geometries, such as a symmetrical geometry and/or and a tapered geometry with a larger distal portion 101110 and a narrower proximal portion 101106, for example. When the surgical end effector jaw 101100 comprises a symmetrical profile, the surgical end effector jaw 101100 can grasp a patient's tissue evenly over the entire end effector jaw 101100. When the surgical end effector jaw 101100 comprises a tapered geometry with a larger distal portion 101110 and a narrower proximal portion 101106, the larger distal portion 101110 can allow the surgical end effector 101100 to grasp a larger portion of the patient's tissue.

The proximal portion 101106 of the outer surface 101108 comprises a substantially smooth surface. The substantially smooth surface can refer to a surface, for example, that is substantially free from projections or unevenness, generally flat or unruffled, and/or substantially of uniform consistency. The distal portion 101110 of the outer surface 101108 comprises a plurality of features. The plurality of features comprises central features 101120, peripheral features 101122, and lateral features 101132, and/or any other suitable features.

The central features 101120, peripheral features 101122, and lateral features 101132 comprise ridges, or teeth, but could comprise any suitable configuration. The central features 101120, peripheral features 101122, and lateral features 101132 can be comprised of various materials. The central, peripheral, and/or lateral features 101120, 101122, 101132 can be comprised of a first material and the outer surface 101108 of the end effector jaw 101100 can be comprised of a second material. The first material can have a greater elasticity than the second material. The second material can have a greater rigidity than the first material. With a less rigid and more elastic material, the central, peripheral, and/or lateral features 101120, 101122, 101132 can deform against a target, such as a patient's tissue, and increase the traction and interaction between the surgical end effector jaw 101100 and the target object.

The plurality of central features 101120 can be substantially perpendicular to the chord of the arc of the jaw 101108. The plurality of central features 101120 are raised above the outer surface of the jaw 101108. In addition, the central features 101120 can be overlaid or overmolded with the lateral features 101132 that can be positioned along the jaw 101108. The lateral features 101132 can be comprised of a different material having a different rigidity and elasticity. For instance, the lateral features 101132 can be more elastic and/or have greater compliance than the central features 101120 which can allow the lateral features 101132 to have a greater ability to interact with a target, such as a patient's tissue. The plurality of central features 101120 can have a slight concavity with respect to the proximal portion 101106 of the end effector jaw 101100, for example. The plurality of peripheral features 101122 can include a convex shape with respect to the proximal portion 101106 of the end effector jaw 101100, for example. The convex-concave-convex pattern of the peripheral-central-peripheral feature combination can allow for greater interaction with a target, such as a patient's tissue.

Where the central features 101120 are aligned substantially perpendicular to the chord of the arc on the surgical end effector jaw 101100, the central features 101120 can facilitate a desired interaction with a patient's tissue. This configuration may allow the surgical end effector jaw 101100 to be drawn through the tissue plane and create a parting action of the tissue. Furthermore, where the patterns of the central features 101120 at the tip of the surgical instrument are aligned with the chord of the arc of the surgical end effector jaw 101100, this pattern facilitates the lateral movement of the surgical end effector jaw 101100 to create a tissue parting action.

The central, peripheral, and lateral features 101120, 101122, 101132 of the end effector jaw 101100 can include symmetrical or asymmetrical patterns that extend along the end effector jaw 101100. The patterns of the central, peripheral, and/or lateral features 101120, 101122, 101132 can be continuous or interlocking and become more interrupted and staggered as they extend towards the proximal portion 101106 and/or distal portion 101110 of the end effector jaw 101100. The various configurations of the central, peripheral, and lateral features 101120, 101122, 101132 can result in posts or standing pillars that can enhance the interaction of these features with the target object, such as a patient's tissue.

The central, peripheral, and lateral features 101120, 101122, 101132 can comprise overmolded plastic and/or polymers. The central, peripheral, and lateral features 101120, 101122, 101132 can comprise various polymers or plastics having different densities and/or properties. A first layer of plastic may be overmolded onto portions of the metallic core 101130 of the end effector jaw 101100. The first layer of plastic can have a first density, rigidity, and elasticity. A second layer of plastic may be overmolded onto portions of the first layer of overmolded plastic and/or onto portions of the metallic core 101130. The second layer of plastic can have a second density, rigidity, and elasticity. The first density, rigidity, and/or elasticity can be the same or different than the second density, rigidity and/or elasticity.

Various sections of the covering 101126 can comprise overmolded plastic and/or polymers. The various sections of the covering 101126 can comprise various polymers or plastics having different densities and/or properties. A first layer of plastics may be overmolded onto portions of the metallic core 101130 of the end effector jaw 101100. The first layer of plastic can have a first density, rigidity, and elasticity. A second layer of plastic may be overmolded onto portions of the first layer of overmolded plastic and/or onto portions of the metallic core 101130. The second layer of plastic can have a second density, rigidity, and elasticity. The first density, rigidity, and/or elasticity can be the same or different than the second density, rigidity and/or elasticity.

In one embodiment, the first layer can comprise a rigid layer that can provide a structural support or backbone to the end effector jaw 101100 along with the metallic core 101130. The second layer can comprise a more elastic and/or less rigid layer. The second layer can be more deformable to create a tissue interaction outer surface that allows for grasping and securing the tissue. The first layer that is more rigid can have a sharper profile and edges that can maintain its shape and actively shear tissue while the outer softer layer acts more like a bumper to prevent cutting tissue before the surgical end effector jaw 101100 is engaged with the desired location or section of tissue.

The inner surface 101118 of the end effector jaw 101100 comprises a plurality of teeth 101116 that extend between the proximal portion 101106 and the distal portion 101110 of the end effector jaw 101100. The plurality of teeth 101116 extend across the width of the inner surface 101118 and follow the tapered profile of the end effector jaw 101100. The central portion of the plurality of teeth 101116 comprises an exposed section of the metallic core 101130. The exposed section of the metallic core 101130 extends substantially uniformly down the central portion of the plurality of teeth 10116 between the proximal portion 101106 and the distal portion 101110. In the alternative, the metallic core 101130 can extend to the inner surface 101118 of the end effector jaw 101100, for example, in an asymmetrical pattern. The different exposed patterns of the metallic core 101130 can allow the end effector jaw 101100 to transmit electrosurgical energy to a patient's tissue in different ways, as described in greater detail below.

When a patient's tissue comes in contact with the metallic core 101130, a surgeon can apply electrosurgical energy to the targeted tissue through the metallic core 101130. The electrosurgical energy can cause ablation and/or cauterization of the targeted tissue.

The distal most portion of the inner surface 101118 comprises a distal bumper portion 101124 and a distal tip 101128. The distal bumper portion 101124 comprises an elastic and/or deformable material that can allow the end effector jaw 101100 to interact with a target object with less irritation to the object. The distal tip 101128 comprises the metallic core 101130 and is configured to deliver electrosurgical energy to a target object, such as a patient's tissue. The distal bumper portion 101124 being constructed of a more elastic and less rigid material can allow the user of the surgical end effector jaw 101100 to be more aggressive without increasing the irritation of the target object, such as a patient's tissue.

In addition, or in the alternative, the various polymers and/or plastics that comprise the surgical end effector jaw 101100 may comprise hydrophobic plastic or materials. The hydrophobic materials can repel liquid, such as body fluids and/or water to keep the dissection features free to dissect. In addition, by repelling fluids, the hydrophobic material may allow a user greater visibility of the interaction portions of the device when using the device in a minimally invasive procedure. The hydrophobic materials may also allow for a consistent dissection surface during the use of the surgical instrument by repelling and keeping away the fluids from the interaction site.

Figure 55:
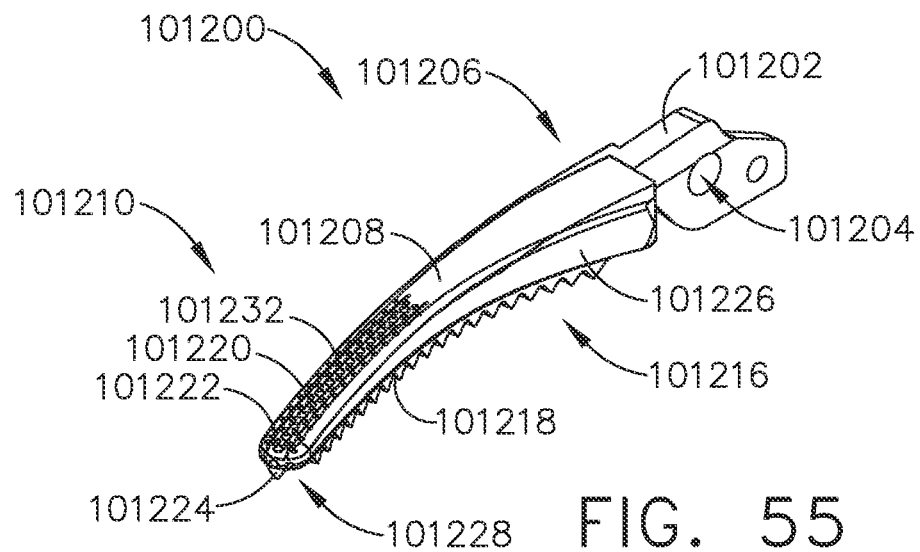
FIG. 55 is a top perspective view of a jaw of a surgical instrument.
Figure 56:
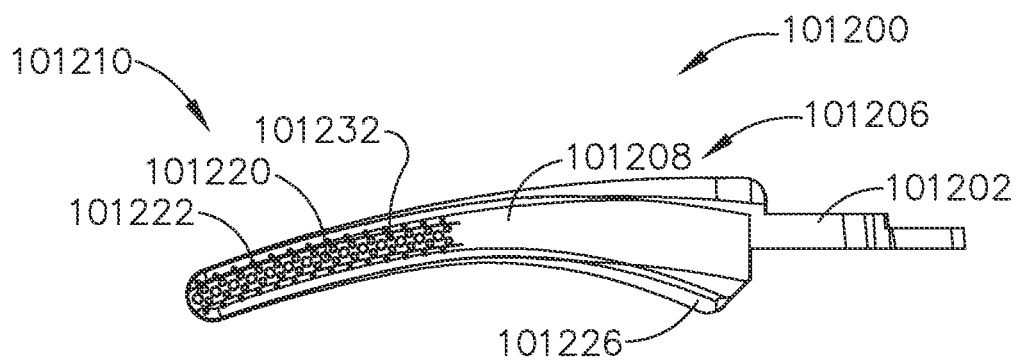
FIG. 56 is a top plan view of the jaw depicted in FIG. 55.
Figure 57:
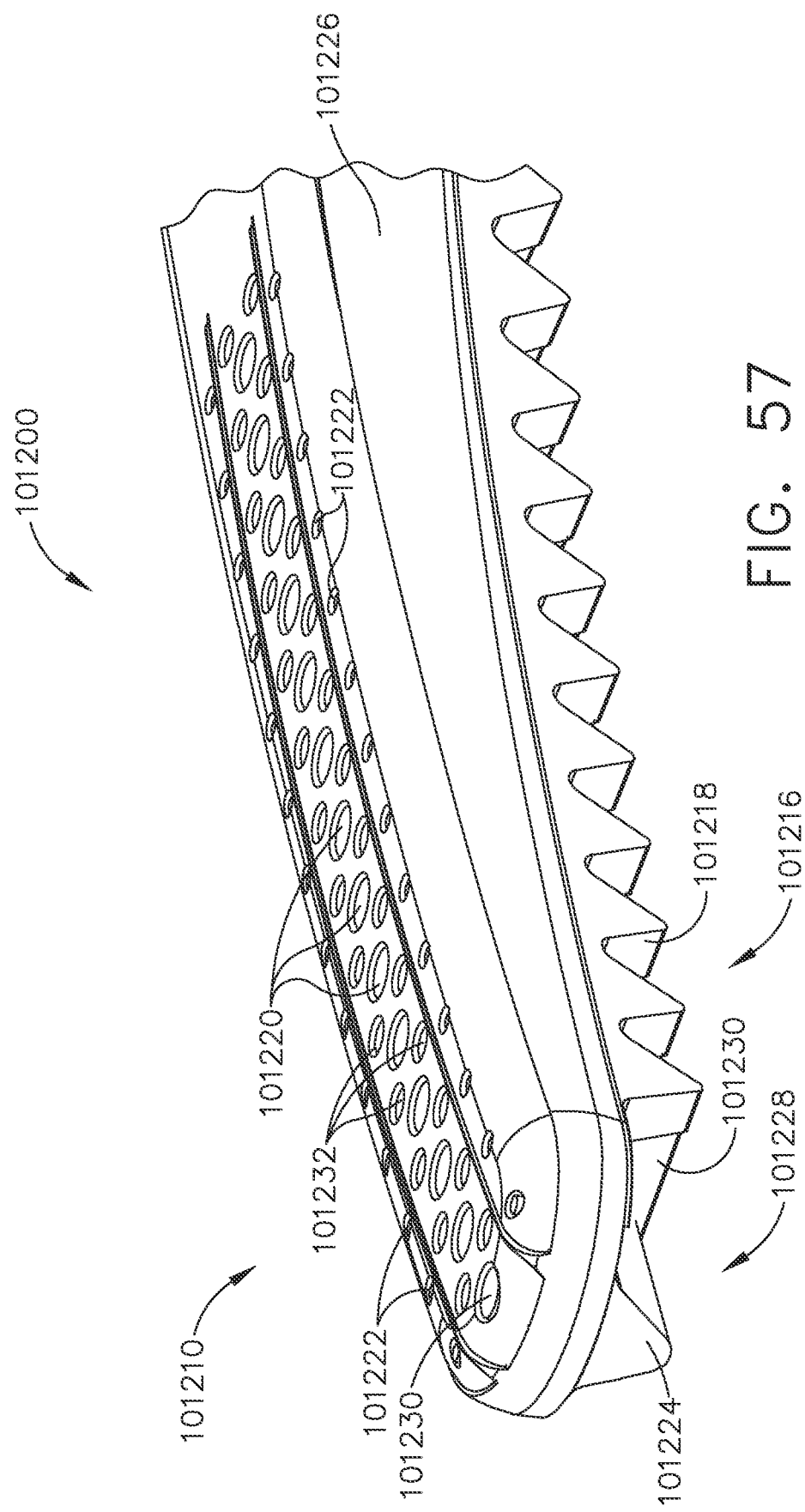
FIG. 57 is a partial perspective view of the jaw depicted in FIG. 55.

FIGS. 55-57 illustrate a surgical end effector jaw 101200 comprising a frame 101202, a metallic core 101230, and a covering 101226. The end effector jaw 101200 comprises an inner surface 101218 and an outer surface 101208. When the end effector jaw 101200 is used in a pair of jaws of a surgical instrument, the inner surfaces 101218 of the end effector jaws 101200 are positioned adjacent one another. The outer surfaces 101208 of the end effector jaw 101200 are positioned on opposite sides of the end effector jaw 101200.

The frame 101202 of the surgical end effector jaw 101200 comprises a socket 101204. When the end effector jaw 101200 is used in a pair of jaws of a surgical instrument, the sockets 101204 of the two end effector jaws 101200 are aligned and a pin can be inserted through the sockets 101204. The pair of end effector jaws 101200 can be rotated about the pin between open and closed positions. The surgical instrument can also comprise an actuator that can move the end effector jaws 101200 between open and closed positions.

The surgical end effector jaw 101200 comprises a proximal portion 101206 and a distal portion 101210. The overall geometry of the end effector jaw 101200 is curved between the proximal portion 101206 and the distal portion 101210. In addition, the end effector jaw 101200 is tapered from the wider proximal portion 101206 to the narrower distal portion 101210. The tapered profile of the end effector jaw 101200 can permit a surgeon to target a specific location within a patient.

In addition, or in the alternative, the surgical end effector jaw 101200 can comprise other geometries, such as a symmetrical geometry and/or and a tapered geometry with a larger distal portion 101210 and a narrower proximal portion 101206, for example. When the surgical end effector jaw 101200 comprises a symmetrical profile, the surgical end effector jaw 101200 can grasp a patient's tissue evenly over the entire end effector jaw 101200. When the surgical end effector jaw 101200 comprises a tapered geometry with a larger distal portion 101210 and a narrower proximal portion 101206, the larger distal portion 101210 can allow the surgical end effector 101200 to grasp a larger portion of the patient's tissue.

The proximal portion 101206 of the outer surface 101208 comprises a substantially smooth surface. The substantially smooth surface can refer to a surface, for example, that is substantially free from projections or unevenness, generally flat or unruffled, and/or substantially of uniform consistency. The distal portion 101210 of the outer surface 101208 comprises a plurality of features. The plurality of features comprises central features 101220, peripheral features 101222, and lateral features 101232, and/or any other suitable features.

The central features 101220, peripheral features 101222, and lateral features 101232 comprise recesses or through holes, but could comprise any suitable configuration. The recesses or through holes expose the metallic core 101230 to the outer surface 101208 and patient tissue. The central features 101220, peripheral features 101122, and lateral features 101232 can comprise different diameters and/or depths, or the same diameters and/or depths. The central features 101220, peripheral features 101122, and lateral features 101232 can also comprise different patterns and/or orientations along the outer surface 101208 of the surgical end effector jaw 101200.

The central features 101220, peripheral features 101222, and lateral features 101232 allow a patient's tissue to come in contact with the metallic core 101230 of the surgical end effector jaw 101200. When a pair of end effector jaws 101200 is used to stretch out tissue, the mechanical forces used to stretch out the tissue can cause the tissue to flow into the central features 101220, peripheral features 101222, and/or lateral features 101232. Once the tissue is in contact with the metallic core 101230 within the central features 101220, peripheral features 101222, and/or lateral features 101232, a clinician can apply electrosurgical energy to the tissue. The combination of mechanical force and electrosurgical energy can allow for ablation of the tissue without tearing the tissue. In addition, or in the alternative, the electrosurgical energy can allow the end effector jaws 101200 to cauterize the tissue as the tissue is spread and/or torn. The combination of electrosurgical energy and mechanical forces can allow a surgeon to perform a surgical procedure with using less mechanical force as the effects of the electrosurgical energy and mechanical force are cumulative.

In various instances, less mechanical force, for example, is required to dissect tissue when more electrosurgical energy is applied. Correspondingly, more mechanical force is required to dissect tissue when less electrosurgical energy is applied. That said, the ratio of mechanical force to electrosurgical energy can be held constant throughout the opening stroke of the dissector jaws. In other instances, the ratio of mechanical force to electrosurgical energy can change throughout the opening stroke of the dissector jaws. In at lease one instance, the electrosurgical energy can increase as the dissector jaws are opened. Such an arrangement can apply the electrosurgical energy when tissue tearing and/or bleeding is most likely to occur. In other instances, the electrosurgical energy can decrease as the dissector jaws are opened. Such an arrangement can create or start an initial otomy that then is stretched open by the mechanical force.

The inner surface 101218 of the end effector jaw 101200 comprises a plurality of teeth 101216 that extend between the proximal portion 101206 and the distal portion 101210 of the end effector jaw 101200. The plurality of teeth 101216 extend across the width of the inner surface 101218 and follow the tapered profile of the end effector jaw 101200. The central portion of the plurality of teeth 101216 comprises an exposed section of the metallic core 101230. The exposed section of the metallic core 101230 extends substantially uniformly down the central portion of the plurality of teeth 10126 between the proximal portion 101206 and the distal portion 101210. In the alternative, the metallic core 101230 can extend to the inner surface 101218 of the end effector jaw 101200, for example, in an asymmetrical pattern. The different exposed patterns of the metallic core 101230 can allow the end effector jaw 101200 to transmit electrosurgical energy to a patient's tissue in different ways, as described in greater detail below.

When a patient's tissue comes in contact with the metallic core 101230, a surgeon can apply electrosurgical energy to the targeted tissue through the metallic core 101230. The electrosurgical energy can cause ablation and/or cauterization of the targeted tissue.

The distal most portion of the inner surface 101218 comprises a distal bumper portion 101224 and a distal tip

101228. The distal bumper portion 101224 comprises an elastic and/or deformable material that can allow the end effector jaw 101200 to interact with a target object with less irritation to the object. The distal tip 101228 comprises the metallic core 101230 and is configured to deliver electrosurgical energy to a target object, such as a patient's tissue. The distal bumper portion 101224 being constructed of a more elastic and less rigid material can allow the user of the surgical end effector jaw 101200 to be more aggressive without increasing the irritation of the target object, such as a patient's tissue.

Various sections of the covering 101226 can comprise overmolded plastic and/or polymers. The various sections of the covering 101226 can comprise various polymers or plastics having different densities and/or properties. A first layer of plastics may be overmolded onto portions of the metallic core 101230 of the end effector jaw 101200. The first layer of plastic can have a first density, rigidity, and elasticity. A second layer of plastic may be overmolded onto portions of the first layer of overmolded plastic and/or onto portions of the metallic core 101230. The second layer of plastic can have a second density, rigidity, and elasticity. The first density, rigidity, and/or elasticity can be the same or different than the second density, rigidity and/or elasticity.

In addition, or in the alternative, the various polymers and/or plastics that comprise the surgical end effector jaw 101200 may comprise hydrophobic plastic or materials. The hydrophobic materials can repel liquid, such as body fluids and/or water to keep the dissection features free to dissect. In addition, by repelling fluids, the hydrophobic material may allow a user greater visibility of the interaction portions of the device when using the device in a minimally invasive procedure. The hydrophobic materials may also allow for a consistent dissection surface during the use of the surgical instrument by repelling and keeping away the fluids from the interaction site.

Figure 58:
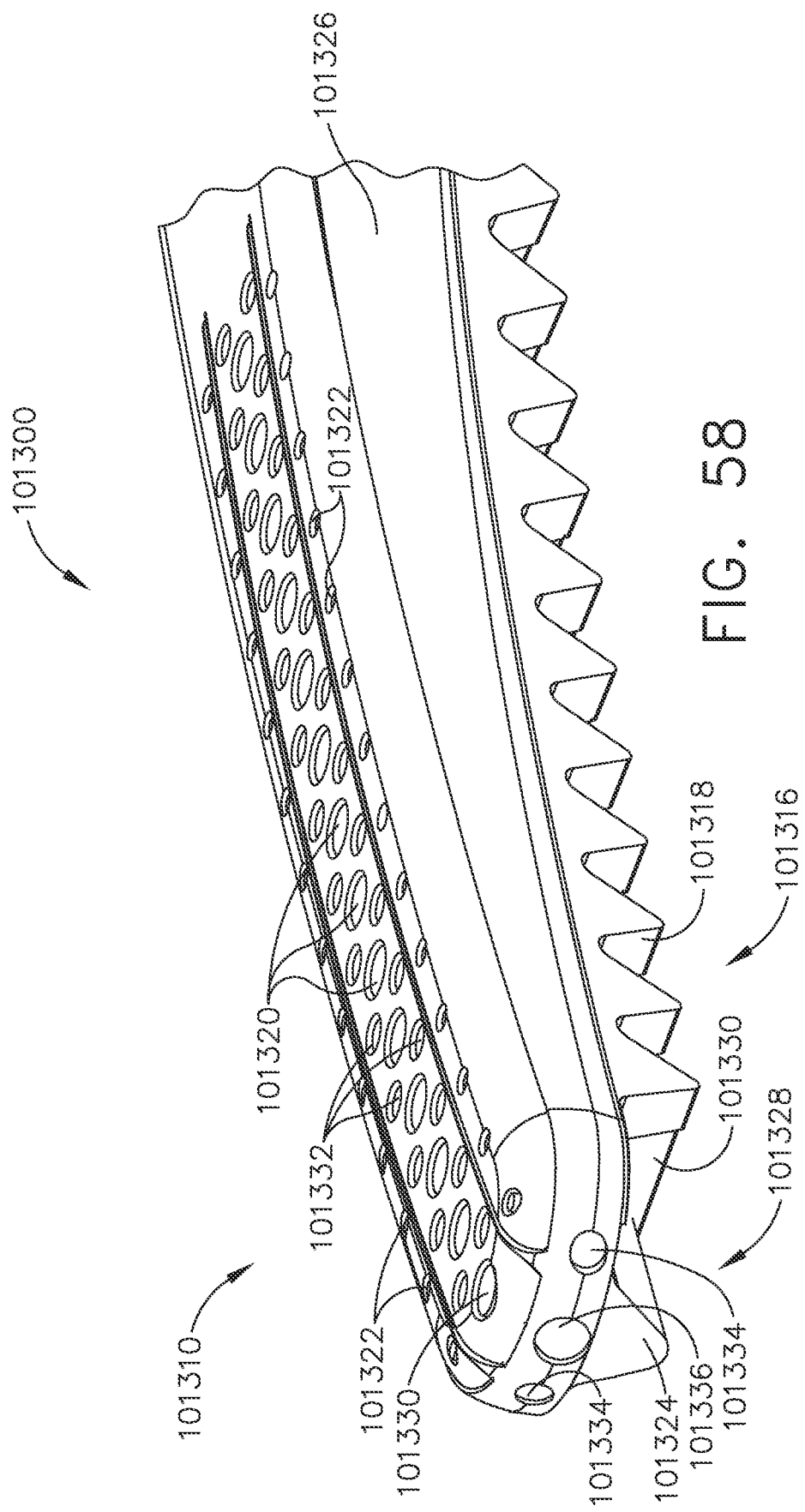
FIG. 58 is a partial perspective view of a jaw of a surgical instrument.

FIG. 58 illustrates an embodiment similar to the end effector 101300, discussed above. The end effector 101300 includes a central distal feature 101336 and lateral distal features 101334 that are positioned on the distal nose of the end effector jaw 101300. The central distal feature 101336 and lateral distal features 101334 comprise recesses or through holes. The recesses or through holes expose the metallic core 101330 to the outer surface 101308. The central distal feature 101336 and lateral distal features 101334 can comprise different diameters and/or depths, or the same diameters and/or depths. The central distal feature 101336 and lateral distal features 101334 can also comprise different patterns and/or orientations along the outer surface 101308 of the surgical end effector jaw 101300.

The central distal feature 101336 and lateral distal features 101334 allow a patient's tissue to come in contact with the metallic core 101330 of the surgical end effector jaw 101300. When a surgeon pushes tissue with the nose of the surgical end effector jaw 101300, the mechanical forces used to push the jaw 101300 into the tissue to stretch out the tissue can cause the tissue to flow into the central distal feature 101336 and lateral distal features 101334. Once the tissue is in contact with the metallic core 101330 within the central distal feature 101336 and/or lateral distal features 101334, electrosurgical energy can be transmitted to the tissue. The combination of mechanical force and electrosurgical energy can allow for ablation of the tissue without tearing the tissue. In addition, or in the alternative, the electrosurgical energy can allow the end effector jaws 101300 to cauterize the tissue as the tissue is spread and/or torn. The combination of electrosurgical energy and mechanical forces can allow a surgeon to perform a surgical procedure with using less mechanical force as the effects of the electrosurgical energy and mechanical force are cumulative.

In various instances, less mechanical force, for example, is required to dissect tissue when more electrosurgical energy is applied. Correspondingly, more mechanical force is required to dissect tissue when less electrosurgical energy is applied. That said, the ratio of mechanical force to electrosurgical energy can be held constant throughout the opening stroke of the dissector jaws. In other instances, the ratio of mechanical force to electrosurgical energy can change throughout the opening stroke of the dissector jaws. In at lease one instance, the electrosurgical energy can increase as the dissector jaws are opened. Such an arrangement can apply the electrosurgical energy when tissue tearing and/or bleeding is most likely to occur. In other instances, the electrosurgical energy can decrease as the dissector jaws are opened. Such an arrangement can create or start an initial otomy that then is stretched open by the mechanical force.

The surgical end effector jaws may also have overmolded plastic bodies having fractal exterior geometries. The fractal exterior geometries can enable the distal tip of the end effector jaws to be more aggressive without creating undesired interaction with the tissue. In another embodiment, the metallic core of the end effector jaws can be positioned near the outer surface and at the distal tip as well as along the spine of the surgical end effector, as seen in FIGS. 55-58. The metallic core may be exposed to the tissue through the various features and recesses along the end effector jaw's outer surface. The metallic core may be recessed within 0.0001-0.001 mm of the outer surface and in electrical contact with the shaft of the surgical instrument to permit the transmission of electrosurgical energy along the end effector jaw. With the metallic core exposed to the tissue, the metallic core can deliver electrosurgical energy to the patient's tissue. In this configuration, the surgical instrument may operate as a hybrid between a mechanical surgical dissector and an electrosurgical instrument.

Example Set 1

Example 1

A surgical suturing system comprising a firing system and an end effector comprising a needle track, a needle comprising suturing material attached thereto, wherein the needle is configured to be guided by and movable within the needle track, and wherein the firing system is configured to apply control motions to the needle to advance the needle through a firing stroke to suture tissue with the suturing material, and means for detecting a parameter of the needle during the firing stroke, wherein the surgical suturing system is configured to automatically adjust the control motions applied to the needle based on the detected parameter.

Example 2

A surgical suturing system comprising a shaft comprising a shaft diameter, a firing drive, and an end effector comprising a flexible needle comprising suturing material attached thereto, wherein the firing drive is configured to apply control motions to the needle to advance the needle through a firing stroke to suture tissue with the suturing material, and wherein the flexible needle comprises a first end and a second end, and a movable needle guide, wherein the movable needle guide is movable between, one, a collapsed configuration for passing the end effector through a trocar, wherein, in the collapsed configuration, the end effector comprises a collapsed diameter which is less than or equal to the shaft diameter, and wherein the first end of the flexible needle is oriented proximal to the second end in the collapsed configuration and, two, an expanded configuration for suturing tissue with the flexible needle, wherein, in the expanded configuration, the end effector comprises an expanded diameter which is greater than the shaft diameter, and wherein the flexible is configured to be advanced through its firing stroke when the movable need guide is in the expanded configuration.

Example 3

A surgical suturing system comprising a shaft comprising a shaft diameter, a firing drive, and an end effector extending distally from the shaft, wherein the end effector comprises a needle track and a needle comprising suturing material attached thereto, wherein the needle is configured to be guided by the needle track and actuated by the firing drive, and wherein the needle is movable along a needle path comprising a maximum capture width which is greater than the shaft diameter.

Example 4

A surgical suturing system comprising a shaft comprising a shaft diameter, a firing drive, and an end effector extending distally from the shaft, wherein the end effector comprises a needle track comprising a linear section and a needle comprising a linear segment, an arcuate segment extending from the linear segment, and suturing material attached to the needle, wherein the needle is configured to be guided by the needle track and actuated by the firing drive, and wherein the firing drive is configured to rotate the needle and displace the needle linearly to move the needle along a continuous loop stroke.

Example 5

A surgical suturing system comprising a shaft, a firing drive, and an end effector extending distally from the shaft, wherein the end effector comprises a needle track and a needle comprising suturing material attached thereto, wherein the needle is configured to be guided by the needle track and actuated by the firing drive through a firing stroke to suture tissue. The surgical suturing system further comprises means for detecting a load experienced by the needle during the firing stroke and means for monitoring the detected load, wherein the surgical suturing system is configured to initiate a change in the operation of the surgical suturing system when the load exceeds a predetermined threshold.

Example 6

A modular surgical instrument comprising a control interface, a shaft extending from the control interface, a drive system, and means for detecting electrical potential applied to the modular surgical instrument, wherein the modular surgical instrument is configured to automatically initiate a change in operation of the modular surgical instrument when the detected electrical potential exceeds a predetermined threshold.

Example 7

A surgical suturing cartridge comprising a needle movable through a firing stroke, wherein the firing stroke comprises a home position, a partially fired position, and a fully actuated position, wherein the needle moves along a path in a single direction from the home position to the fully actuated position and from the fully actuated position to the home position during a full firing stroke. The surgical suturing cartridge further comprises a sensing circuit comprising a supply conductor comprising a first resistive leg, wherein the first resistive leg terminates at a first terminal and comprises a first resistance, and a return conductor comprising a second resistive leg terminating at a second terminal and comprising a second resistance and a third resistive leg terminating at a third terminal and comprising a third resistance, wherein the first resistance, the second resistance, and the third resistance are different, and wherein the first resistive leg and the second resistive leg are wired in parallel with respect to the return conductor. The needle is movable through the firing stroke to contact the first terminal, the second terminal, and the third terminal in the home position of the firing stroke, the second terminal and the third terminal in a partially fired position of the firing stroke, and the first terminal and the third terminal in a fully fired position of the firing stroke. The surgical suturing cartridge further comprises means for monitoring the resistance of the sensing circuit during the firing stroke, wherein the sensing circuit comprises a first circuit resistance when the needle is in the home position, a second circuit resistance when the needle is in the partially fired position, and a third circuit resistance when the needle is in the fully fired position, wherein the first circuit resistance, the second circuit resistance, and the third circuit resistance are different, and wherein the resistance of the sensing circuit indicates the position of the needle during the firing stroke.

Example 8

A surgical suturing system comprising a shaft, a firing drive, and an end effector extending distally from the shaft, wherein the end effector comprises a needle track and a needle comprising suturing material attached thereto, wherein the needle is configured to be guided by the needle track and actuated by the firing drive through a firing stroke to suture tissue. The surgical suturing system further comprises a proximity sensor configured to sense movement of the needle during its firing stroke to indicate the position of the needle to a control program of the surgical suturing system.

Example 9

A surgical suturing system comprising a shaft, a firing drive, and an end effector extending distally from the shaft, wherein the end effector comprises a needle driver configured to be actuated by the firing drive, a needle track, and a needle comprising suturing material attached thereto, wherein the needle is configured to be guided by the needle track and actuated by the needle driver through a firing stroke to suture tissue. The surgical suturing system further comprises a proximity sensor configured to sense movement of the needle driver as the needle driver advances the needle through the firing stroke to indicate the position of the needle driver to a control program of the surgical suturing system.

Example 10

A surgical suturing system comprising a shaft, a firing drive, and an end effector extending distally from the shaft, wherein the end effector comprises a needle driver configured to be actuated by the firing drive, a needle track, and a needle comprising suturing material attached thereto, wherein the needle is configured to be guided by the needle track and actuated by the needle driver through a firing stroke to suture tissue. The surgical suturing system further comprises a position sensing system comprising a magnet and a Hall Effect sensor, wherein the needle is configured to interrupt a magnetic field induced by the magnet to change the condition of the Hall Effect sensor to indicate the position of the needle driver to a control program of the surgical suturing system.

Example 11

A surgical suturing system comprising a shaft, a firing drive, and an end effector extending distally from the shaft, wherein the end effector comprises a needle driver configured to be actuated by the firing drive, a needle track comprising a first wall and a second wall, and a needle comprising suturing material attached thereto, wherein the needle is configured to be guided by the needle track and actuated by the needle driver through a firing stroke to suture tissue. The surgical suturing system further comprises a position sensing circuit comprising a first conductor connected to the first wall of the track and a second conductor connected to the second wall of the track, wherein the needle is configured to move into and out of contact with the first wall and the second wall as the needle is moved through the firing stroke to indicate the position of the needle.

Example 12

A surgical suturing system comprising a shaft, a firing drive, and an end effector extending distally from the shaft, wherein the end effector comprises a needle driver configured to be actuated by the firing drive, a needle track comprising a first wall and a second wall, and a needle comprising suturing material attached thereto, wherein the needle is configured to be guided by the needle track and actuated by the needle driver through a firing stroke to suture tissue. The surgical suturing system further comprises a position sensing flex circuit comprising a first conductor comprising a first terminal folded over and adhered to the first wall of the track and a second conductor comprising a second terminal folded over and adhered to the second wall of the track, wherein the needle is configured to move into and out of contact with the first terminal and the second terminal as the needle is moved through the firing stroke to indicate the position of the needle.

Example 13

A surgical suturing system comprising a shaft, a firing drive, and an end effector extending distally from the shaft, wherein the end effector comprises a needle driver configured to be actuated by the firing drive, a needle track comprising a first wall and a second wall, and a needle comprising suturing material attached thereto, wherein the needle is configured to be guided by the needle track and actuated by the needle driver through a firing stroke to suture tissue. The surgical suturing system further comprises a position sensing circuit comprising a first conductor comprising a first terminal molded into to the first wall of the track and a second conductor comprising a second terminal molded into to the second wall of the track, wherein the needle is configured to move into and out of contact with the first terminal and the second terminal as the needle is moved through the firing stroke to indicate the position of the needle.

Example 14

A surgical suturing system comprising a shaft, a firing drive, and an end effector extending distally from the shaft, wherein the end effector comprises a needle driver configured to be actuated by the firing drive, a needle track comprising a first wall and a second wall, and a needle comprising suturing material attached thereto, wherein the needle is configured to be guided by the needle track and actuated by the needle driver through a firing stroke to suture tissue. The surgical suturing system further comprises a position sensing system comprising an infrared LED emitter, and a photodetector configured to detect infrared light emitted by the infrared LED emitter, wherein the needle is configured to interrupt the infrared light emitted by the infrared LED emitter as the needle is moved through the firing stroke to indicate the position of the needle.

Example 15

A surgical suturing system comprising a shaft, a firing drive, and an end effector attached to the shaft, wherein the end effector comprises a needle configured to be driven by the firing drive, a needle track configured to guide the needle through a firing stroke, and suturing material attached to the needle. The surgical suturing system further comprises a plurality of proximity sensors configured to detect the position of the needle as the needle is advanced through the firing stroke, wherein the plurality of proximity sensors are positioned such that the needle is configured to trip at least two of the plurality of proximity sensors at all times during the firing stroke, wherein the surgical suturing system is configured to determine if the needle has diverted from the needle track if less than two of the proximity sensors are tripped at any point during the firing stroke.

Example 16

A surgical suturing system comprising a shaft comprising a shaft diameter, a firing drive, and an end effector attached to the shaft, wherein the end effector comprises a needle driver configured to be actuated by the firing drive, a needle track, a needle comprising suturing material attached thereto, wherein the needle is configured to be guided by the needle track and actuated by the needle driver through a firing stroke to suture tissue, and a tissue bite region where the needle is configured to be advanced through the tissue bite region to suture tissue, wherein the tissue bite region comprises a width greater than the shaft diameter. The end effector is movable relative to the shaft such that the tissue bite region can extend beyond the shaft diameter.

Example 17

A surgical suturing system comprising a shaft, a firing drive, and an end effector extending distally from the shaft, wherein the end effector comprises a needle track comprising a linear section and a needle comprising a linear segment, an arcuate segment extending from the linear segment, and suturing material attached to the needle, wherein the needle is configured to be guided by the needle track and actuated by the firing drive, wherein the firing drive is configured to rotate the needle and displace the needle linearly to move the needle throughout a needle firing stroke, and wherein the needle firing stroke can be varied from stroke to stroke.

Example 18

A surgical suturing system comprising a shaft, a firing drive, and an end effector extending distally from the shaft, wherein the end effector comprises a circular needle comprising a first end and a second end helically extending at least 360 degrees from the first end, wherein the first end and the second end define a vertical distance therebetween. The end effector further comprises suturing material attached to the circular needle, wherein the circular needle is configured to be actuated through a helical drive stroke to suture tissue.

Example 19

A surgical suturing system comprising a shaft, a firing drive, and an end effector extending distally from the shaft, wherein the end effector comprises a helical needle and suturing material attached to the helical needle, wherein the helical needle is configured to be driven through a three dimensional needle stroke by the firing drive to suture tissue.

Example 20

A surgical suturing system comprising a shaft, a firing drive, and an end effector extending distally from the shaft, wherein the end effector comprises a needle driver configured to be actuated by the firing drive, wherein the needle driver is configured to drive a needle installed within the end effector, and a needle track configured to guide the needle installed within the end effector through a needle firing stroke. The end effector is configured to receive suturing needles having different circumference lengths, and wherein the surgical suturing system is configured to adjust the actuation of the needle driver to accommodate needles with different circumference lengths installed within the end effector.

Example 21

A surgical suturing system comprising a shaft, a firing drive, and an end effector extending distally from the shaft, wherein the end effector comprises a needle driver configured to be actuated by the firing drive, wherein the needle driver is configured to drive a needle installed within the end effector, and a needle track configured to guide the needle installed within the end effector through a needle firing stroke. The end effector is configured to receive suturing needles having different diameters, and wherein the surgical suturing system is configured to adjust the actuation speed of the needle driver to accommodate needles with different diameters installed within the end effector.

Example 22

A surgical suturing system comprising an actuation interface comprising a motor, an attachment interface, and an output drive configured to be driven by the motor. The surgical suturing system further comprises a modular attachment configured to be attached to and detached from the actuation interface, wherein the modular attachment comprises a shaft, an input drive configured to be coupled with the output drive upon the attachment of the modular attachment and the actuation interface, and an end effector extending distally from the shaft. The surgical suturing system further comprises a load sensor configured to detect the load applied to the input drive and the output drive when the input drive and the output drive are actuated by the motor, wherein the surgical suturing system is configured to limit current flow through the motor when the detected load reaches a first threshold, and wherein the surgical suturing system is configured to shut off the motor when the detected load falls below a second threshold.

Example 23

A surgical suturing system comprising an actuation interface comprising a motor, an attachment interface, and an output drive configured to be driven by the motor. The surgical suturing system further comprises a modular attachment configured to be attached to and detached from the actuation interface, wherein the modular attachment comprises a shaft, an input drive configured to be coupled with the output drive upon the attachment of the modular attachment and the actuation interface, and an end effector extending distally from the shaft. The surgical suturing system further comprises a load sensor configured to detect the load applied to the input drive and the output drive when the input drive and the output drive are actuated by the motor, wherein the surgical suturing system is configured to limit power to the motor when the detected load reaches a first threshold, and wherein the surgical suturing system is configured to stop power to the motor when the detected load falls below a second threshold.

Example 24

A surgical instrument comprising a motor, a drive system configured to be actuated by the motor, and a shaft. The surgical instrument further comprises an articulation joint, an end effector attached to the shaft by way of the articulation joint, wherein the end effector is configured to be articulated relative to the shaft by the drive system, and a monitoring system configured to monitor electrical energy applied to the surgical instrument, wherein the surgical instrument is configured to reverse the actuation of the motor when an unexpected electrical energy is detected.

Example 25

A surgical instrument comprising a motor, a drive system configured to be actuated by the motor, and a shaft. The surgical instrument further comprises an articulation joint, an end effector attached to the shaft by way of the articulation joint, wherein the end effector is configured to be articulated relative to the shaft by the drive system, and a monitoring system configured to monitor electrical energy applied to the surgical instrument, wherein the surgical instrument is configured to pause actuation of the motor when an unexpected electrical energy is detected and indicate to a user the condition of the surgical instrument.

Example 26

A surgical instrument comprising a motor, a drive system configured to be actuated by the motor, and a shaft. The surgical instrument further comprises an end effector attached to the shaft and a strain gauge mounted to the shaft, wherein the surgical instrument is configured to indicate to a user the strain detected by the strain gauge to indicate force being applied to tissue with the shaft.

Example 27

A surgical suturing system comprising a first motor, a second motor, a shaft, and an end effector attached to the shaft, wherein the end effector comprises a longitudinal axis, wherein the second motor is configured to rotate the end effector about the longitudinal axis, a needle configured to be driven through a firing stroke by the first motor, and suturing material attached to the needle. The surgical suturing system further comprises a first sensor configured to sense force experienced by the needle as the needle is advanced through the firing stroke, a second sensor configured to sense load torque experienced by the end effector as the end effector is rotated about the longitudinal axis, a third sensor configured to sense bending load experienced by the shaft and a control program configured to monitor the force experienced by the needle such that, if the force experienced by the needle exceeds a first predetermined threshold, the control program limits the current flow through the first motor, monitor the load torque experienced by the end effector such that, if the load torque experienced by the end effector exceeds a second predetermined threshold, the control program limits the current flow through the second motor, and monitor the bending load experienced by the shaft such that, if the load bending load experienced by the shaft exceeds a third predetermined threshold, the control program reduces the current flow through the second motor.

Example 28

A surgical instrument configured to apply a suture to the tissue of a patient comprising an end effector comprising a replaceable suture cartridge comprising a suture removably stored therein, an actuator configured to deploy the suture, and a lockout configurable in a locked configuration and an unlocked configuration, wherein the lockout is in the locked configuration when the replaceable suture cartridge is not in the end effector, wherein the lockout prevents the actuator from being actuated when the lockout is in the locked configuration, wherein the lockout is in the unlocked configuration when the replaceable suture cartridge is positioned in the end effector, and wherein the lockout permits the actuator to deploy the suture when the lockout is in the unlocked configuration. The surgical instrument further comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the locked configuration.

Example 29

A surgical instrument configured to apply a suture to the tissue of a patient comprising an end effector. The end effector comprises a replaceable suture cartridge comprising a suture removably stored therein, an actuator configured to deploy the suture, and a lockout configurable in a locked configuration and an unlocked configuration, wherein the lockout is in the locked configuration when the replaceable suture cartridge is not in the end effector, wherein the lockout prevents the actuator from being actuated when the lockout is in the locked configuration, wherein the lockout is in the unlocked configuration when the replaceable suture cartridge is positioned in the end effector, and wherein the lockout permits the actuator to deploy the suture when the lockout is in the unlocked configuration. The surgical instrument further comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit provides haptic feedback to the user of the surgical instrument when the sensing system determines that the lockout is in the locked configuration.

Example 30

A surgical instrument configured to apply a suture to the tissue of a patient comprising an end effector. The end effector comprises a replaceable suture cartridge comprising a suture removably stored therein, an actuator configured to deploy the suture, and a lockout configurable in a locked configuration and an unlocked configuration, wherein the lockout is in the locked configuration when the replaceable suture cartridge has been completely expended, wherein the lockout prevents the actuator from being actuated when the lockout is in the locked configuration, wherein the lockout is in the unlocked configuration when the replaceable suture cartridge is positioned in the end effector and has not been completely expended, and wherein the lockout permits the actuator to deploy the suture when the lockout is in the unlocked configuration. The surgical instrument further comprises a handle, an electric motor configured to drive the actuator, a control circuit configured to control the electric motor, and a sensing system configured to determine when the lockout is in the locked configuration, wherein the sensing system is in communication with the control circuit, and wherein the control circuit prevents the actuation of the electric motor when the sensing system determines that the lockout is in the configuration.

Example Set 2

Example 1

A surgical dissector for manipulating the tissue of a patient comprising a shaft comprising an electrical pathway and a first jaw pivotably coupled to the shaft. The first jaw comprises a first inner surface, a first outer surface comprising a first opening, wherein the first outer surface faces away from the first inner surface, a first electrically-conductive portion in electrical communication with the electrical pathway, wherein the first electrically-conductive portion can contact the tissue through the first opening, and a first electrically-insulative portion. The surgical dissector further comprises a second jaw pivotably coupled to the shaft, wherein the second jaw comprises a second inner surface, wherein the second inner surface faces toward the first inner surface, a second outer surface comprising a second opening, wherein the second outer surface faces away from the second inner surface, a second electrically conductive portion in electrical communication with the electrical pathway, wherein the second electrically-conductive portion can contact the tissue through the second opening, and a second electrically-insulative portion.

Example 2

The surgical dissector of Example 1, further comprising a drive system operably coupled with the first jaw and the second jaw, wherein the drive system comprises an electric motor configured to drive the first jaw and the second jaw from a closed position into an open position.

Example 3

The surgical dissector of Example 2, further comprising a handle comprising a grip, wherein the electric motor is position in the handle.

Example 4

The surgical dissector of Examples 2 or 3, further comprising a housing configured to be attached to a robotic surgical system, wherein the electric motor is position in the robotic surgical system.

Example 5

The surgical dissector of Examples 2, 3, or 4, further comprising a control system in communication with the electric motor and the electrical pathway, wherein the control system is configured to control the electrical power supplied to the motor and the electrical pathway.

Example 6

The surgical dissector of Example 5, wherein the control system comprises a pulse width modulation motor control circuit configured to control the speed of the electric motor.

Example 7

The surgical dissector of Examples 5 or 6, wherein the control system comprises at least one of a voltage regulation circuit and a current regulation circuit configured to control the electrical power supplied to the electrical pathway.

Example 8

The surgical dissector of Examples 5, 6, or 7 wherein the control system is configured to control the voltage potential applied to the electrical pathway to control the electrical power applied to the patient tissue.

Example 9

The surgical dissector of Examples 5, 6, 7, or 8, wherein the control system comprises an AC voltage control circuit configured to control the voltage potential applied to the electrical pathway to control the electrical power applied to the patient tissue.

Example 10

The surgical dissector of Example 5, 6, 7, 8, or 9, wherein the control system comprises a DC voltage control circuit configured to control the voltage potential applied to the electrical pathway to control the electrical power applied to the patient tissue.

Example 11

The surgical dissector of Examples 5, 6, 7, 8, 9, or 10, wherein the control system comprises a current control circuit configured to control the electrical power applied to the patient tissue.

Example 12

The surgical dissector of Examples 1, 2, 3, 4, 5, 6, 7, 8, 9, 10, or 11, further comprising a drive system operably coupled with the first jaw and the second jaw, wherein the drive system comprises an electric motor configured to drive the first jaw and the second jaw from an open position into a closed position.

Example 13

A surgical dissector for manipulating the tissue of a patient comprising a shaft comprising an electrical pathway and a first jaw pivotably coupled to the shaft. The first jaw comprises an inner surface, an outer surface comprising an opening, an electrically-conductive electrode in electrical communication with the electrical pathway, wherein the electrically-conductive electrode can contact the tissue through the opening, and an electrically-insulative portion. The surgical dissector further comprises a second jaw pivotably coupled to the shaft.

Example 14

The surgical dissector of Example 14, further comprising a drive system operably coupled with the first jaw and the second jaw, wherein the drive system comprises an electric motor configured to drive the first jaw and the second jaw from a closed position into an open position.

Example 15

The surgical dissector of Examples 14 or 15, further comprising a control system in communication with the electric motor and the electrical pathway, wherein the control system is configured to control the electrical power supplied to the electric motor and the electrical pathway.

Example 16

The surgical dissector of Example 15, wherein the control system comprises a pulse width modulation motor control circuit configured to control the speed of the electric motor.

Example 17

The surgical dissector of Examples 15 or 16, wherein the control system comprises at least one of a voltage regulation circuit and a current regulation circuit configured to control the electrical power supplied to the electrical pathway.

Example 18

The surgical dissector of Examples 15, 16, or 17, wherein the control system comprises an AC voltage control circuit configured to control the voltage potential applied to the electrical pathway to control the electrical power applied to the patient tissue.

Example 19

The surgical dissector of Examples 15, 16, 17, or 18, wherein the control system comprises a current control circuit configured to control the electrical power applied to the patient tissue.

Example 20

A surgical dissector for manipulating the tissue of a patient comprising a shaft comprising an electrical pathway, a first jaw pivotably coupled to the shaft, wherein the first jaw comprises an inner surface, an outer surface comprising an opening, an electrically-conductive electrode in electrical communication with the electrical pathway, wherein the electrically-conductive electrode can contact the tissue through the opening, and an electrically-insulative portion. The surgical dissector further comprises a second jaw pivotably coupled to the shaft and means for spreading the first jaw and the second jaw and applying electrical energy to the patient tissue at the same time.

Example Set 3

Example 1

A surgical suturing system comprising a shaft, a firing drive, and an end effector extending distally from the shaft, wherein the end effector comprises a needle driver, wherein the firing drive is configured to apply control motions to the needle driver, a needle track, and a needle comprising suturing material attached thereto, wherein the needle is configured to be guided by the needle track and actuated by the needle driver through a firing stroke to suture tissue. The surgical suturing system further comprises a position sensing circuit comprising a detectable parameter, wherein the needle is configured to vary the detectable parameter of the positioning sensing circuit as the needle is advanced through the firing stroke, wherein the surgical suturing system is configured to monitor the detectable parameter of the position sensing circuit and automatically adjust the control motions applied to the needle driver based on the detected parameter.

Example 2

The surgical suturing system of Example 1, wherein the position sensing system comprises an infrared LED emitter and a photodetector configured to detect infrared light emitted by the infrared LED emitter, wherein the needle is configured to interrupt the infrared light emitted by the infrared LED emitter as the needle is moved through the firing stroke to indicate the position of the needle.

Example 3

The surgical suturing system of Example 2, wherein the needle track comprises an exit location where the needle exits the needle track and an entry location where the needle reenters the needle track, and wherein the infrared LED emitter is positioned at the exit location.

Example 4

The surgical suturing system of Examples 1, 2, or 3, wherein the detectable parameter comprises a load experienced by the needle during the firing stroke.

Example 5

The surgical suturing system of Example 4, wherein the surgical suturing system is configured to adjust the control motions when the load exceeds a predetermined threshold.

Example 6

The surgical suturing system of Examples 1, 2, 3, 4, or 5, wherein the position sensing system comprises a plurality of proximity sensors configured to detect the position of the needle as the needle is advanced through the firing stroke.

Example 7

The surgical suturing system of Example 6, wherein the plurality of proximity sensors are positioned such that the needle is configured to trip at least two of the plurality of proximity sensors at all times during the firing stroke, and wherein the surgical suturing system is configured to determine if the needle has diverted from the needle track if less than two of the proximity sensors are tripped at any point during the firing stroke.

Example 8

The surgical suturing system of Examples 1, 2, 3, 4, 5, 6, or 7, wherein the position sensing system comprises a magnet and a Hall Effect sensor, wherein the needle is configured to interrupt a magnetic field induced by the magnet to change the condition of the Hall Effect sensor to indicate the position of the needle driver to a control program of the surgical suturing system.

Example 9

The surgical suturing system of Examples 1, 2, 3, 4, 5, 6, 7, or 8, wherein the position sensing system comprises a proximity sensor configured to sense movement of the needle driver as the needle driver advances the needle through the firing stroke to indicate the position of the needle driver to a control program of the surgical suturing system.

Example 10

The surgical suturing system of Examples 1, 2, 3, 4, 5, 6, 7, 8, or 9, wherein the needle track comprises a first wall and a second wall, wherein the position sensing system comprises a flex circuit, and wherein the flex circuit comprises a first conductor comprising a first terminal folded over and adhered to the first wall of the needle track and a second conductor comprising a second terminal folded over and adhered to the second wall of the needle track, wherein the needle is configured to move into and out of contact with the first terminal and the second terminal as the needle is moved through the firing stroke to indicate the position of the needle.

Example 11

The surgical suturing system of Example 10, wherein the first terminal and the second terminal comprise electrical brushes.

Example 12

A surgical suturing system comprising a needle movable through a firing stroke, wherein the firing stroke comprises a home position, a partially fired position, and a fully actuated position, wherein the needle moves along a path in a single direction from the home position to the fully actuated position and from the fully actuated position to the home position during a full firing stroke. The surgical suturing system further comprises a sensing circuit comprising a supply conductor comprising a first resistive leg, wherein the first resistive leg terminates at a first terminal and comprises a first resistance and a return conductor comprising a second resistive leg terminating at a second terminal and comprising a second resistance and a third resistive leg terminating at a third terminal and comprising a third resistance, wherein the first resistance, the second resistance, and the third resistance are different, and wherein the first resistive leg and the second resistive leg are wired in parallel with respect to the return conductor. The needle is movable through the firing stroke to contact the first terminal, the second terminal, and the third terminal in the home position of the firing stroke, the second terminal and the third terminal in a partially fired position of the firing stroke, and the first terminal and the third terminal in a fully fired position of the firing stroke. The surgical suturing system further comprises means for monitoring the resistance of the sensing circuit during the firing stroke, wherein the sensing circuit comprises a first circuit resistance when the needle is in the home position, a second circuit resistance when the needle is in the partially fired position, and a third circuit resistance when the needle is in the fully fired position, wherein the first circuit resistance, the second circuit resistance, and the third circuit resistance are different, and wherein the resistance of the sensing circuit indicates the position of the needle during the firing stroke.

Example 13

The surgical suturing system of Example 12, wherein the firing stroke comprises a circular path.

Example 14

The surgical suturing system of Examples 12 or 13, further comprising a power control program configured to determine a rate of advancement of the needle based on the monitored resistance.

Example 15

The surgical suturing cartridge of Examples 12, 13, or 14, further comprising a power control program configured to automatically adjust control motions applied to the needle based on the monitored resistance.

Example 16

A surgical suturing system comprising a firing system and an end effector comprising a needle track, an arcuate needle comprising suturing material attached thereto, wherein the arcuate needle is configured to be guided by the needle track, and wherein the firing system is configured to apply control motions to the needle to advance the arcuate needle through a circular firing stroke to suture tissue with the suturing material, and a needle detection circuit configured to detect a parameter of the arcuate needle during the circular firing stroke, wherein the surgical suturing system is configured to automatically adjust the control motions applied to the arcuate needle based on the detected parameter.

Example 17

The surgical suturing system of Example 16, wherein the needle detection circuit comprises an electrical resistance circuit, wherein the electrical resistance circuit comprises a resistance configured to be altered by the arcuate needle as the arcuate needle is actuated through the circular firing stroke.

Example 18

The surgical suturing system of Examples 16 or 17, wherein the needle detection circuit comprises a plurality of proximity sensors.

Example 19

The surgical suturing system of Examples 16, 17, or 18, wherein the needle detection circuit comprises a plurality of proximity sensors.

Example 20

The surgical suturing system of Examples 16, 17, 18, or 19, wherein the needle detection circuit comprises a Hall Effect sensor and a magnet.

Example Set 4

Example 1

A surgical suturing system comprising a shaft comprising a shaft diameter, a firing drive, and an end effector extending distally from the shaft, wherein the end effector comprises a needle track and a needle comprising suturing material attached thereto, wherein the needle is configured to be guided by the needle track and actuated by the firing drive through a firing stroke, and wherein the needle is movable along a needle path comprising a maximum capture width which is greater than the shaft diameter.

Example 2

The surgical suturing system of Example 1, wherein the needle is non-circular.

Example 3

The surgical suturing system of Examples 1 or 2, wherein the needle comprises a linear segment and an arcuate segment.

Example 4

The surgical suturing system of Examples 1, 2, or 3, wherein the needle comprises a park position relative to the end effector, wherein the firing stroke comprises a firing stroke path, and wherein the park position is not located on the firing stroke path.

Example 5

The surgical suturing system of Example 4, wherein the surgical suturing system is contained with a space defined by the shaft diameter when the needle is in the park position.

Example 6

The surgical suturing system of Examples 1, 2, 3, 4, or 5, wherein the needle comprises a linear segment, a proximal arcuate segment, and a distal arcuate segment, wherein the linear segment is disposed between the proximal arcuate segment and the distal arcuate segment.

Example 7

The surgical suturing system of Examples 1, 2, 3, 4, 5, or 6, wherein the needle track comprises a non-circular path.

Example 8

The surgical suturing system of Examples 1, 2, 3, 4, 5, 6, or 7, wherein the needle is configured to be actuated in a proximal direction, in a distal direction, and about a rotational axis defined by an end of the needle.

Example 9

A surgical suturing system comprising a shaft comprising a shaft diameter, a firing drive, and an end effector extending distally from the shaft, wherein the end effector comprises a needle track comprising a linear section and a needle comprising a linear segment, an arcuate segment extending from the linear segment, and suturing material attached to the needle, wherein the needle is configured to be guided by the needle track and actuated by the firing drive, and wherein the firing drive is configured to rotate the needle and displace the needle linearly to move the needle along a continuous loop stroke.

Example 10

The surgical suturing system of Example 9, wherein the needle track comprises a y-shaped track.

Example 11

A surgical suturing system comprising a shaft comprising a shaft diameter, a firing drive and an end effector comprising a flexible needle comprising suturing material attached thereto, wherein the firing drive is configured to apply control motions to the needle to advance the needle through a firing stroke to suture tissue with the suturing material, and wherein the flexible needle comprises a first end and a second end, and a movable needle guide, wherein the movable needle guide is movable between a collapsed configuration for passing the end effector through a trocar, wherein, in the collapsed configuration, the end effector comprises a collapsed diameter which is less than or equal to the shaft diameter, and wherein the first end of the flexible needle is oriented proximal to the second end in the collapsed configuration, and an expanded configuration for suturing tissue with the flexible needle, wherein, in the expanded configuration, the end effector comprises an expanded diameter which is greater than the shaft diameter, and wherein the flexible is configured to be advanced through its firing stroke when the movable need guide is in the expanded configuration.

Example 12

The surgical suturing system of Example 11, wherein the end effector is hingedly coupled to the shaft such that the end effector can be rotated relative to the shaft.

Example 13

The surgical suturing system of Examples 11 or 12, wherein the end effector further comprises a proximal feed wheel and a distal feed wheel configured to be driven by the firing drive, and wherein the flexible needle is configured to be fed into and out of the end effector by the proximal feed wheel and the distal feed wheel.

Example 14

The surgical suturing system of Examples 11, 12, or 13, wherein the end effector further comprises a proximal feed wheel, a distal feed wheel, and an intermediate feed wheel positioned between the proximal feed wheel and the distal feed wheel, wherein the feed wheels are configured to be driven by the firing drive, wherein the flexible needle is configured to be fed into and out of the end effector by the proximal feed wheel and the distal feed wheel.

Example 15

The surgical suturing system of Examples 11, 12, 13, or 14, wherein the movable needle guide is pivotally coupled to the end effector, and wherein the shaft is coupled to the movable needle guide such that the shaft can pivot the movable needle guide between the collapsed configuration and the expanded configuration.

Example 16

A surgical suturing system comprising a shaft comprising a shaft diameter, a firing drive, and an end effector attached to the shaft, wherein the end effector comprises a needle driver configured to be actuated by the firing drive, a needle track, a needle comprising suturing material attached thereto, wherein the needle is configured to be guided by the needle track and actuated by the needle driver through a firing stroke to suture tissue, and a tissue bite region where the needle is configured to be advanced through the tissue bite region to suture tissue, wherein the tissue bite region comprises a width greater than the shaft diameter, wherein the end effector is movable relative to the shaft such that the tissue bite region can extend beyond the shaft diameter.

Example 17

A surgical suturing system comprising a shaft, a firing drive, and an end effector extending distally from the shaft, wherein the end effector comprises a needle track comprising a linear section and a needle comprising a linear segment, an arcuate segment extending from the linear segment and suturing material attached to the needle, wherein the needle is configured to be guided by the needle track and actuated by the firing drive, wherein the firing drive is configured to rotate the needle and displace the needle linearly to move the needle throughout a needle firing stroke, and wherein the needle firing stroke can be varied from stroke to stroke.

Example 18

The surgical suturing system of Example 17, wherein the needle comprises a canoe-like shape.

Example 19

The surgical suturing system of Examples 17 or 18, wherein the needle comprises a park position relative to the end effector, wherein the firing stroke comprises a firing stroke path, and wherein the park position is not located on the firing stroke path.

Example 20

The surgical suturing system of Example 19, wherein the shaft comprises a shaft diameter, wherein the surgical suturing system is contained with a space defined by the shaft diameter when the needle is in the park position.

Example Set 5

Example 1

A surgical bipolar forceps instrument comprising a shaft comprising a first electrical pathway and a second electrical pathway and a closable jaw assembly comprising a first jaw comprising a first tissue cutting blade and a first electrically-conductive portion in electrical communication with the first electrical pathway, and a second jaw comprising a second tissue cutting blade and a second electrically-conductive portion in electrical communication with the second electrical pathway. The surgical bipolar forceps instrument further comprises a pivot, wherein at least one of the first jaw and the second jaw are rotatable about the pivot, a drive system comprising an electric motor operably engaged with at least one of the first jaw and the second jaw, wherein the drive system is configured to apply a mechanical cutting force to the tissue through the rotation of at least one of the first jaw and the second jaw, a power supply system in electrical communication with the first electrical pathway and the second electrical pathway configured to apply an electrosurgical cutting force to the tissue through at least one of the first electrically-conductive portion and the second electrically-conductive portion, and a control system configured to control when the mechanical cutting force and the electrosurgical cutting force are applied to the tissue.

Example 2

The surgical bipolar forceps instrument of Example 1, wherein the control system is configured to monitor the current drawn by the electric motor and change the speed of the electric motor to control the closing speed of the jaw assembly.

Example 3

The surgical bipolar forceps instrument of Examples 1 or 2, wherein the control system comprises a pulse width modulation motor control circuit to change the speed of the electric motor.

Example 4

The surgical bipolar forceps instrument of Examples 1, 2, or 3, wherein the control system is configured to increase the electrosurgical cutting force when the electrical motor slows down.

Example 5

The surgical bipolar forceps instrument of Examples 1, 2, 3, or 4, wherein the control system is configured to increase the electrosurgical cutting force when the electrical motor is slowed down by the control system.

Example 6

The surgical bipolar forceps instrument of Examples 1, 2, 3, 4, or 5, wherein the control system is configured to decrease the electrosurgical cutting force when the electrical motor speeds up.

Example 7

The surgical bipolar forceps instrument of Examples 1, 2, 3, 4, 5, or 6, wherein the control system is configured to increase the electrosurgical cutting force when the electrical motor is sped up by the control system.

Example 8

The surgical bipolar forceps instrument of Examples 1, 2, 3, 4, 5, 6, or 7, wherein the control system is configured to initiate the electrosurgical cutting force when the electrical motor slows down.

Example 9

The surgical bipolar forceps instrument of Examples 1, 2, 3, 4, 5, 6, 7, or 8, wherein the control system is configured to initiate the electrosurgical cutting force when the electrical motor stops.

Example 10

The surgical bipolar forceps instrument of Examples 1, 2, 3, 4, 5, 6, 7, 8, or 9, wherein the control system is configured to monitor the current drawn by the electric motor and change at least one of the current and the voltage applied to the tissue through the first and the electrically-conductive portions.

Example 11

The surgical bipolar forceps instrument of Examples 1, 2, 3, 4, 5, 6, 7, 8, 9, or 10, wherein the control system comprises at least one of a voltage regulation circuit and a current regulation circuit configured to control the electrical power supplied to the tissue.

Example 12

The surgical bipolar forceps instrument of Examples 1, 2, 3, 4, 5, 6, 7, 8, 9, 10, or 11, wherein the control system comprises an AC voltage control circuit configured to control the voltage potential applied to the first and the electrically-conductive portions.

Example 13

The surgical bipolar forceps instrument of Examples 1, 2, 3, 4, 5, 6, 7, 8, 9, 10, 11, or 12, wherein the control system comprises a DC voltage control circuit configured to control the voltage potential applied to the first and the electrically-conductive portions.

Example 14

The surgical bipolar forceps instrument of Examples 1, 2, 3, 4, 5, 6, 7, 8, 9, 10, 11, 12, or 13, wherein the control system comprises a current control circuit configured to control the electrical power applied to the patient tissue.

Example 15

The surgical bipolar forceps instrument of Examples 1, 2, 3, 4, 5, 6, 7, 8, 9, 10, 11, 12, 13, or 14, wherein the control system comprises a pulse width modulation motor control circuit to change the speed of the electric motor.

Example 16

The surgical bipolar forceps instrument of Examples 1, 2, 3, 4, 5, 6, 7, 8, 9, 10, 11, 12, 13, 14, or 15, wherein the control system slows the electric motor when the electrosurgical cutting force increases.

Example 17

The surgical bipolar forceps instrument of Examples 1, 2, 3, 4, 5, 6, 7, 8, 9, 10, 11, 12, 13, 14, 15, or 16, wherein the control system slows the electric motor when the control system increases the electrosurgical cutting force.

Example 18

The surgical bipolar forceps instrument of Examples 1, 2, 3, 4, 5, 6, 7, 8, 9, 10, 11, 12, 13, 14, 15, 16, or 17, wherein the control system speeds up the electric motor when the electrosurgical cutting force decreases.

Example 19

The surgical bipolar forceps instrument of Examples 1, 2, 3, 4, 5, 6, 7, 8, 9, 10, 11, 12, 13, 14, 15, 16, 17, or 18, wherein the control system speeds up the electric motor when the control system decreases the electrosurgical cutting force.

Example 20

The surgical bipolar forceps instrument of Examples 1, 2, 3, 4, 5, 6, 7, 8, 9, 10, 11, 12, 13, 14, 15, 16, 17, 18, or 19, wherein the control system stops the electric motor when the electrosurgical cutting force increases.

Example 21

The surgical bipolar forceps instrument of Examples 1, 2, 3, 4, 5, 6, 7, 8, 9, 10, 11, 12, 13, 14, 15, 16, 17, 18, 19, or 20, wherein the control system stops the electric motor when the control system increases the electrosurgical cutting force Example 22

A surgical instrument comprising a shaft comprising an electrical pathway and a closable jaw assembly comprising a first jaw comprising a tissue cutting blade and an electrode in electrical communication with the electrical pathway. The closable jaw assembly further comprises a second jaw. The surgical instrument further comprises a pivot, wherein the first jaw is rotatable about the pivot, a drive system comprising an electric motor operably engaged with the first jaw, wherein the drive system is configured to apply a mechanical cutting force to the tissue through the rotation of the first jaw, a power supply system in electrical communication with the electrical pathway configured to apply an electrosurgical cutting force to the tissue through the electrode, and a control system configured to control when the mechanical cutting force and the electrosurgical cutting force are applied to the tissue.

Example 23

A surgical instrument comprising a shaft comprising an electrical pathway and a closable jaw assembly comprising a first jaw comprising a tissue cutting blade and a second jaw comprising an electrode in electrical communication with the electrical pathway. The surgical instrument further comprises a pivot, wherein at least one of the first jaw is rotatable about the pivot, a drive system comprising an electric motor operably engaged with the closable jaw assembly, wherein the drive system is configured to apply a mechanical cutting force to the tissue through the rotation of at least one of the first jaw and the second jaw, a power supply system in electrical communication with the electrical pathway configured to apply an electrosurgical cutting force to the tissue through the electrode, and a control system configured to control when the mechanical cutting force and the electrosurgical cutting force are applied to the tissue.

Example 24

A surgical bipolar forceps instrument comprising a shaft comprising a first electrical pathway and a second electrical pathway and a first jaw comprising a first tissue cutting blade and a first electrically-conductive portion in electrical communication with the first electrical pathway. The surgical bipolar forceps instrument further comprises a second jaw comprising a second tissue cutting blade and a second electrically-conductive portion in electrical communication with the second electrical pathway. The surgical bipolar forceps instrument further comprises a pivot, wherein at least one of the first jaw and the second jaw are rotatable about the pivot and means for treating the tissue of a patient comprising means for applying a mechanical cutting force to the tissue through the rotation of at least one of the first jaw member and the second jaw member and means for applying electrosurgical force to the tissue through at least one of the first electrically-conductive portion and the second electrically-conductive portion.

Example Set 6

Example 1

A modular surgical instrument comprising a control interface, a shaft extending from said control interface, an end effector extending from said shaft, and a control circuit configured to sense the electrical potential applied to said modular surgical instrument, determine if said sensed electrical potential is above a predetermined threshold, and adjust the operation of said modular surgical instrument when said sensed electrical potential exceeds said predetermined threshold.

Example 2

The modular surgical instrument of Example 1, further comprising an articulation joint, wherein said end effector is configured to be articulated relative to said shaft by said control interface, and wherein said control circuit is configured to unarticulate said end effector when said sensed electrical potential exceeds said predetermined threshold and said end effector is in an articulated state.

Example 3

The modular surgical instrument of Example 2, wherein said control circuit is configured to unarticulate said end effector to an unarticulated state.

Example 4

The modular surgical instrument of Examples 2 or 3, wherein said control circuit is configured to unarticulate said end effector until said sensed electrical potential falls below said predetermined threshold.

Example 5

The modular surgical instrument of Examples 1, 2, 3, or 4, wherein said control circuit is configured to carry out an operation adjustment until said sensed electrical potential falls below said predetermined threshold.

Example 6

The modular surgical instrument of Examples 1, 2, 3, 4, or 5, wherein said control circuit is configured to carry out an operation adjustment until a predetermined period of time passes after said sensed electrical potential falls below said predetermined threshold.

Example 7

A surgical suturing system comprising an actuation interface comprising a motor, an attachment interface, and an output drive configured to be driven by said motor. The surgical suturing system further comprises a modular attachment configured to be attached to and detached from said actuation interface, wherein said modular attachment comprises a shaft, an input drive configured to be coupled with said output drive upon the attachment of said modular attachment and said actuation interface, and an end effector extending distally from said shaft. The surgical suturing system further comprises a load sensor configured to detect the load applied to said input drive and said output drive when said input drive and said output drive are actuated by said motor, wherein said surgical suturing system further comprises a control circuit configured to monitor said detected load from said load sensor, limit current flow through said motor when said detected load reaches a first threshold, and stop power to said motor when said detected load reaches a second threshold.

Example 8

The surgical suturing system of Example 7, wherein said second threshold is less than said first threshold.

Example 9

The surgical suturing system of Example 7, wherein said second threshold is greater than said first threshold.

Example 10

A surgical instrument comprising a motor, a drive system configured to be actuated by said motor, a shaft, an articulation joint, an end effector attached to said shaft by way of said articulation joint, wherein said end effector is configured to be articulated relative to said shaft by said drive system, and a control circuit configured to detect electrical energy applied to said surgical instrument; and alter the actuation of said motor when an unexpected electrical energy is detected.

Example 11

The surgical instrument of Example 10, wherein said control circuit is configured to reverse the actuation of said motor when an unexpected electrical energy is detected.

Example 12

The surgical instrument of Examples 10 or 11, wherein said control circuit is configured to pause the actuation of said motor when an unexpected electrical energy is detected.

Example 13

The surgical instrument of Examples 10, 11, or 12, wherein said control circuit is further configured to indicate to a user the condition of said surgical instrument when an unexpected electrical energy is detected.

Example 14

A surgical suturing system comprising a first motor, a second motor, a shaft, an end effector attached to said shaft, wherein said end effector comprises a longitudinal axis, wherein said second motor is configured to rotate said end effector about said longitudinal axis, a needle configured to be driven through a firing stroke by said first motor and suturing material attached to said needle. The surgical suturing system further comprises a first sensor configured to sense force experienced by said needle as said needle is advanced through said firing stroke, a second sensor configured to sense load torque experienced by said end effector as said end effector is rotated about said longitudinal axis, a third sensor configured to sense bending load experienced by said shaft, and a control program configured to monitor said force experienced by said needle such that, if said force experienced by said needle exceeds a first predetermined threshold, said control program limits the current flow through said first motor, monitor said load torque experienced by said end effector such that, if said load torque experienced by said end effector exceeds a second predetermined threshold, said control program limits the current flow through said second motor, and monitor said bending load experienced by said shaft such that, if said load bending load experienced by said shaft exceeds a third predetermined threshold, said control program reduces the current flow through said second motor.

Example 15

The surgical suturing system of Example 14, wherein said first sensor comprises a strain gauge.

Example 16

The surgical suturing system of Examples 14 or 15, wherein said second sensor comprises a strain gauge.

Example 17

The surgical suturing system of Examples 14, 15, or 16, wherein said third sensor comprises a strain gauge.

Example 18

The surgical suturing system of Examples 14, 15, 16, or 17, wherein data measured by said first sensor, said second sensor, and said third sensor are indicated to a user of said surgical suturing system.

Example 19

The surgical suturing system of Examples 14, 15, 16, 17, or 18, further comprising a surgical suturing cartridge.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The devices, systems, and methods disclosed in the Subject Application can be used with the devices, systems, and methods disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein.

The devices, systems, and methods disclosed in the Subject Application can also be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated by reference in their entireties herein.

The devices, systems, and methods disclosed in the Subject Application can also be used with the devices, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment of suture material to seal tissue. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:
- U.S. patent application Ser. No. 11/013,924, entitled TROCAR SEAL ASSEMBLY, now U.S. Pat. No. 7,371,227;
- U.S. patent application Ser. No. 11/162,991, entitled ELECTROACTIVE POLYMER-BASED ARTICULATION MECHANISM FOR GRASPER, now U.S. Pat. No. 7,862,579;
- U.S. patent application Ser. No. 12/364,256, entitled SURGICAL DISSECTOR, now U.S. Patent Application Publication No. 2010/0198248;
- U.S. patent application Ser. No. 13/536,386, entitled EMPTY CLIP CARTRIDGE LOCKOUT, now U.S. Pat. No. 9,282,974;
- U.S. patent application Ser. No. 13/832,786, entitled CIRCULAR NEEDLE APPLIER WITH OFFSET NEEDLE AND CARRIER TRACKS, now U.S. Pat. No. 9,398,905;
- U.S. patent application Ser. No. 12/592,174, entitled APPARATUS AND METHOD FOR MINIMALLY INVASIVE SUTURING, now U.S. Pat. No. 8,123,764;
- U.S. patent application Ser. No. 12/482,049, entitled ENDOSCOPIC STITCHING DEVICES, now U.S. Pat. No. 8,628,545;
- U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
- U.S. patent application Ser. No. 11/343,803, entitled SURGICAL INSTRUMENT HAVING RECORDING CAPABILITIES, now U.S. Pat. No. 7,845,537;
- U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical dissector for manipulating the tissue of a patient, comprising:
 a shaft comprising an electrical pathway;
 a first jaw pivotably coupled to said shaft, wherein said first jaw comprises:
  a first inner surface;
  a first electrically-insulative portion comprising a first outer surface, wherein said first outer surface comprises a first opening, and wherein said first outer surface faces away from said first inner surface; and a first electrically-conductive portion in electrical communication with said electrical pathway, wherein said first electrically-conductive portion can contact the tissue through said first opening; and a second jaw pivotably coupled to said shaft, and wherein said second jaw comprises:

a second inner surface, wherein said second inner surface faces toward said first inner surface;

a second electrically insulative portion comprising a second outer surface, wherein said second outer surface comprises a second opening, and wherein said second outer surface faces away from said second inner surface; and a second electrically conductive portion in electrical communication with said electrical pathway, wherein said second electrically-conductive portion can contact the tissue through said second opening.

2. The surgical dissector of claim 1, further comprising a drive system operably coupled with said first jaw and said second jaw, wherein said drive system comprises an electric motor configured to drive said first jaw and said second jaw from a closed position into an open position.

3. The surgical dissector of claim 2, further comprising a handle comprising a grip, wherein said electric motor is positioned in said handle.

4. The surgical dissector of claim 2, further comprising a housing configured to be attached to a robotic surgical system, wherein said electric motor is positioned in the robotic surgical system.

5. The surgical dissector of claim 2, further comprising a control system in communication with said electric motor and said electrical pathway, wherein said control system is configured to control the electrical power supplied to said electric motor and said electrical pathway.

6. The surgical dissector of claim 5, wherein said control system comprises a pulse width modulation motor control circuit configured to control the speed of said electric motor.

7. The surgical dissector of claim 6, wherein said control system comprises at least one of a voltage regulation circuit and a current regulation circuit configured to control the electrical power supplied to said electrical pathway.

8. The surgical dissector of claim 6, wherein said control system is configured to control the voltage potential applied to said electrical pathway to control the electrical power applied to the patient tissue.

9. The surgical dissector of claim 6, wherein said control system comprises an AC voltage control circuit configured to control the voltage potential applied to said electrical pathway to control the electrical power applied to the patient tissue.

10. The surgical dissector of claim 6, wherein said control system comprises a DC voltage control circuit configured to control the voltage potential applied to said electrical pathway to control the electrical power applied to the patient tissue.

11. The surgical dissector of claim 6, wherein said control system comprises a current control circuit configured to control the electrical power applied to the patient tissue.

12. The surgical dissector of claim 1, further comprising a drive system operably coupled with said first jaw and said second jaw, wherein said drive system comprises an electric motor configured to drive said first jaw and said second jaw from an open position into a closed position.

13. A surgical dissector for manipulating the tissue of a patient, comprising:

a shaft comprising an electrical pathway;

a first jaw pivotably coupled to said shaft, wherein said first jaw comprises:

an inner surface;

an electrically-insulative portion comprising an outer surface, wherein said outer surface comprises an opening; and an electrically-conductive electrode in electrical communication with said electrical pathway, wherein said electrically-conductive electrode can contact the tissue through said opening; and a second jaw pivotably coupled to said shaft, wherein said inner surface faces said second jaw and said outer surface faces away from said second jaw.

14. The surgical dissector of claim 13, further comprising a drive system operably coupled with said first jaw and said second jaw, wherein said drive system comprises an electric motor configured to drive said first jaw and said second jaw from a closed position into an open position.

15. The surgical dissector of claim 14, further comprising a control system in communication with said electric motor and said electrical pathway, wherein said control system is configured to control the electrical power supplied to said electric motor and said electrical pathway.

16. The surgical dissector of claim 15, wherein said control system comprises a pulse width modulation motor control circuit configured to control the speed of said electric motor.

17. The surgical dissector of claim 16, wherein said control system comprises at least one of a voltage regulation circuit and a current regulation circuit configured to control the electrical power supplied to said electrical pathway.

18. The surgical dissector of claim 16, wherein said control system comprises an AC voltage control circuit configured to control the voltage potential applied to said electrical pathway to control the electrical power applied to the patient tissue.

19. The surgical dissector of claim 16, wherein said control system comprises a current control circuit configured to control the electrical power applied to the patient tissue.

20. A surgical dissector for manipulating the tissue of a patient, comprising:

a shaft comprising an electrical pathway;

a first jaw pivotably coupled to said shaft, wherein said first jaw comprises:

an inner surface;

an electrically-insulative portion comprising an outer surface, wherein said outer surface comprises an opening; and an electrically-conductive electrode in electrical communication with said electrical pathway, wherein said electrically-conductive electrode can contact the tissue through said opening;

a second jaw pivotably coupled to said shaft, wherein said inner surface faces said second jaw and said outer surface faces away from said second jaw; and means for spreading said first jaw and said second jaw and applying electrical energy to the patient tissue at the same time.

* * * * *